United States Patent [19]
Honjo et al.

[11] Patent Number: 6,096,878
[45] Date of Patent: Aug. 1, 2000

[54] HUMAN IMMUNOGLOBULIN $V_H$ GENE SEGMENTS AND DNA FRAGMENTS CONTAINING THE SAME

[75] Inventors: Tasuku Honjo; Fumihiko Matsuda, both of Kyoto, Japan

[73] Assignee: Japan Tobacco Inc., Tokyo, Japan

[21] Appl. No.: 08/545,809

[22] PCT Filed: May 10, 1993

[86] PCT No.: PCT/JP93/00603

§ 371 Date: Mar. 27, 1996

§ 102(e) Date: Mar. 27, 1996

[87] PCT Pub. No.: WO94/26895

PCT Pub. Date: Nov. 24, 1994

[51] Int. Cl.[7] .................................................. C07M 21/04
[52] U.S. Cl. .................. 536/23.53; 536/23.1; 536/23.51; 435/91.1
[58] Field of Search .............................. 536/23.1, 23.53, 536/23.51; 435/91.1

[56] References Cited

FOREIGN PATENT DOCUMENTS

| | | |
|---|---|---|
| 4-504365 | 1/1991 | Japan . |
| 5-501062 | 3/1993 | Japan . |
| WO 91/10741 | 7/1991 | WIPO . |
| WO 91/18983 | 12/1991 | WIPO . |

OTHER PUBLICATIONS

The Journal of Immunology, vol. 149, No. 4, (1992) E.H. Sasso et al.; "$V_H$ genes in tandem array comprise related germline motif"; pp. 1230–1236.
The Journal of Immunology, vol. 148, No. 9, (1992) K.W. van Dijk et al., "Mapping of human H chain V region genes ($V_H$4) using deletional analysis and pulsed field gel electrophoresis"; pp. 2923–2931.
European Journal of Immunology, vol. 23, No. 4, (1993) X. Mariette et al., "Nucleotide sequence analysis of four human monoclonal IgM with an antibody activity to myelin–associated glycoprotein"; pp. 846–851.
Blood, vol. 76, No. 10 (1990) O.G. Jonsson et al., "Detection of minimal residual disease in acute lympho–blastic leukemia using immunoglobulin hypervariable region specific oligo–nucleotide probes", pp. 2072–2079.
Article; "Structure and Physical Map of 64 Variable Segments . . . Heavy–Chain Locus"; Nature Genetics; vol. 3; Jan. 1993; pp. 88–94.
"The Repertoire of Human Germline $V_H$ Sequences . . . Hypervariable Loops"; 1992 Academic Press Limited; J. Mol. Biol. 227; pp. 776–798.
"Immunoglobulin Heavy and Light Chain . . . Germline Genes"; Immunology Letters 34 (1992); pp. 57–62; Elsevier Science Publishers B.V.
"Nucleotide Sequences of the cDNAs . . . HIV–1—gp41"; Nucleic Acids Research; vol. 18, No. 16; 1990 Oxford University Press; p. 4927.
"Expression of Members of the Immunoglobulin . . . Leukemia"; International Immunology; vol. 4, No. 3; pp. 313–320 1989.

"Content and Organization of the Human Ig . . . Locus"; The EMBO Journal; vol. 7, No. 3; pp. 737–738; 1988.
"The Human Cord Blood Antibody . . . Family"; Eur. J. Immunol. 22 (1992) pp. 241–245.
"Early Restriction of the Human Antibody Repertoire"; Science vol. 238 (1987); pp. 791–793.
"Preferential Utilization of Conserved Immunoglobulin . . . Life"; Proc. Natl. Acad. Sci. U.S.A. vol. 87 (1990) pp. 6146–6150.
"Restricted Ig H Chain V Gene Usage . . . Polysaccharide"; J. Immunol. vol. 147 (1991); pp. 1667–1674.
"$V_H$ Sequence of a Human Anti–Sm . . . Germline Genes"; J. Immunol. vol. 142 (1989); pp. 883–887.
"The Role of Clonal Selection . . . Lymphoma"; J. Exp. Med. vol. 174 (1991); pp. 525–537.
"Structural Analyses of Human Developmentally Regulated Vh3 Genes"; Scand. J. Immunol. vol. 31 (1990); pp. 257–267.
"Relationship of Human Variable Region . . . Autoantibodies"; J. Immunol. vol. 139 (1987); pp. 2496–2501.
Nucleotide Sequences of the cDNAs . . . Tumor Cells; Nucleic Acids Res.; vol. 17, No. 11 (1989; p. 4385.
"Structure and Multiplicity of Genes . . . Region"; Proc. Natl. Acad. Sci. U.S.A. vol. 77 (1980); pp. 6561–6565.
"Nucleotide Sequences of Eight Human . . . Families"; J. Immunol. vol. 142 (1989); pp. 4054–4061.
"Early Human IgH Gene Assembly . . . Cell Lines", J. Exp. Med. vol. 169 (1989); pp. 1391–1403.
"Presence of Immunoglobulin (Ig) M and IgG . . . Immunodeficiency"; J. Clin. Invest. vol. 85 (1990); pp. 1722–1727.
"Analysis of Variable Region Genes . . . Origin"; J. Immunol. 143 (1989); pp. 685–691.
"Molecular Basis of an Autoantibody–associated Restriction Fragment Length . . . Diseases"; J. Clin. Invest. vol. 88 (1991); pp. 193–203.
"The Complete Nucleotide Sequences . . . Rheumatoid Arthritis"; J. Clin. Invest. vol. 86 (1990); pp. 1320–1328.
"Relationship of Variable Region Geneses . . . Autoantibodies"; J. Exp. Med. vol. 169 (1989); pp. 1631–1643.
"Complete Sequence of the Genes Encoding . . . Arthritis Patient"; Int. Immunol. vol. 3 (1991); pp. 865–875.
"Evolutionary Aspects of Immunoglobulin . . . Subgroups"; Proc. Natl. Acad. Sci. U.S.A. vol. 80 (1983) pp. 855–859.
"Human Heavy–Chain Variable Region . . . Leukemia"; Proc. Natl. Acad. Sci. U.S.A. vol. 84 (1987); pp. 8563–8567.

(List continued on next page.)

*Primary Examiner*—Julie Burke
*Attorney, Agent, or Firm*—Fish & Richardson P.C.

[57] ABSTRACT

Novel human immunoglobulin $V_H$ segments and DNA fragments containing the same are disclosed. The DNA fragment according to the present invention is the fragment having a size of about 800 kbp which is shown in FIG. 1. The human immunoglobulin $V_H$ segments according to the present invention are contained in the fragment of this DNA fragment of about 800 kbp, and there are 50 novel segments. The base sequences of these :segments are shown in the Sequence Listing. The present invention also provides DNA fragments which contain two or more of these $V_H$ segments.

8 Claims, 4 Drawing Sheets

OTHER PUBLICATIONS

"The Smaller Human $V_H$ Gene . . . Polymorphism"; EMBO J. vol. 8 (1989); pp. 3471–3478.

"Organization and Evolution of Immunglobulin $V_H$ Gene Subgroups"; Proc. Natl. Acad. Sci. U.S.A. vol. 79 (1982); pp. 4405–4409.

"A New Human Immunoglobulin . . . B–Cell Tumours"; Nature vol. 331 (1988); pp. 446–449.

"Chromosomal Organization . . . Family"; J. Immunol. vol. 150 (1993.4);pp. 2858–2868.

"The Human Immunoglobulin . . . Locus"; Eur. J. Immunol. vol. 23 (1993); pp. 832–839.

"Rapid Screening of a Human Genomic Library . . . Sequences"; Proc. Natl. Acad. Sci. U.S.A. vol. 86 (1989) pp. 5898–5902.

"Transfer of a Yeast Artificial Chromosome . . . Cells"; Proc. Natl. Acad. Sci. U.S.A. vol. 87 (1990) pp. 5109–5113.

"The Human HPRT Gene on a Yeast Artificial Chromosome . . . Fusion"; Genomics vol. 9 (1991) pp. 742–750.

"Structure of the Human Immunoglobulin . . . D Genes", Cell vol. 27 (1981); pp. 583–591.

"Meiotic Recombination Between Yeast Artificial Chromosomes . . . Protooncogene"; Proc. Natl. Acad. Sci. U.S.A. vol. 87 (1990); pp. 9913–9917.

"Chromosomal Region of the Cystic Fibrosis . . . Mapping"; Science vol. 250 (1990); pp. 94–98.

"Meiotic Recombination and Segregation . . . Cerevisiae"; Proc. Natl. Acad. Sci. U.S.A. vol. 89 (1992); pp. 5296–5300.

"Mitotic Recombination of Yeast Artificial Chromosomes"; Nucleic Acid Research vol. 20, No. 12; pp. 3135–3138.

"Rescue of End Fragments of Yeast . . . in Yeast", Nucleic Acids Res. vol. 19 (1991); pp. 4943–4948.

"Second–Generation Approach to the Construction . . . Libraries"; Genomics vol. 8 (1990); pp. 297–303.

"Guide to Yeast Genetics and Molecular Biology"; (1991); pp. 251–270.

"Sequences of Proteins of Immunological Interest"; 5th Edition (1991).

"Systematic Screening of Yeast Artificial–Chromosome . . . Reaction"; Proc. Natl. Acad. Sci. U.S.A. vol. 87 (1990); pp. 1213–1217.

"Cloning of Human Immunoglobulin . . . Genes"; Proc. Natl. Acad. Sci. U.S.A. vol. 79 (1982); pp. 3833–3837.

"Organization and Evolution of Variable Region . . . Chain"; J. Mol. Biol. vol. 190 (1986); pp. 529–541.

"Rearranged Immunoglobulin Heavy Chain . . . Region"; Proc. Natl. Acad. Sci. U.S.A. vol. 81 (1984); pp. 5194–5198.

"A Novel Family of Variable . . . Chain"; J. Mol. Biol. vol. 195 (1987); pp. 761–768.

"A Novel, Rapid Method for the Isolation . . . Clones"; Nucleic Acids Res. vol. 18 (1990); pp. 2887–2890.

"Recombinant Fragment Assay . . . Reaction"; Nucleic Acids Res. vol. 16 (1988); pp. 8887–8903.

Roitt et al Imunology Secodn Edition 6.3–6.5 1989.

New Riverside University Dictionary "gene" 1984.

Ilustrated Dictionary of Immunology Cruse et al 189 1994.

HUMAN IMMUNOGLOBULIN $V_H$ GENE SEGMENTS AND DNA FRAGMENTS CONTAINING THE SAME

This is a 371 national stage filing of International Application No. PCT/JP93/00603, with an international filing data of May 10, 1993, now abandoned.

TECHNICAL FIELD

This invention relates to novel human immunoglobulin $V_H$ gene segments and DNA fragments containing the same. The segments and DNA fragments according to this present invention are useful for producing human antibodies using a mammalian host by a genetic engineering process.

BACKGROUND ART

Immunoglobulins are composed of the L chains and H chains, each of which consists of a variable region (V region) and a constant region (C region) that has a structure common to immunoglobulin molecules. What determines the antigenic specificity of an antibody is the V region. The V region of the H chain is encoded by V, D (diversity) and J (joining) genes (The gene of the H chain is expressed by placing a suffix "H", like "$V_H$"). One of the important reasons why the V regions of immunoglobulins are highly diverse and can provide antibodies which specifically binds to infinite number of antigens is the rearrangement of V, D and J genes. That is, there are a plurality of V genes, D genes and J genes, respectively and they are randomly combined in somatic cells to form a gene encoding a single mRNA. Since the combination is randomly selected, side variety of immunoglobulin V regions are provided.

On the other hand, antibodies currently employed for therapies of various diseases are those originated from animals other than human, such as mouse. However, if these antibodies are administered to human, since the antibodies are of exogenous origin, an immunological response occurs in the human body to present allergy and to neutralize the antibodies. To overcome this problem, it is desired to use antibodies originated from human for the therapies for human. Further, if a human antibody is industrially produced using human as the host and using a human-originated antigen, a problem of immunological tolerance is brought about, so that this approach employing the known method is very difficult. Thus, the production of human immunoglobulins by a genetic engineering process using an animal as a host is now being developed (for example, Japanese Laid-open PCT Application (Kohyo) No. 4-504365; Proc. Natl. Acad. Sci. USA, Vol. 86, pp.5898–5902, August 1989; Proc. Natl. Acad. Sci. USA, Vol. 87, pp.5109–5113, July 1990; Genomics 8, 742–750 (1991)). However, in the conventional methods in which human immunoglobulin genes are expressed in host animals other than human, there is a problem that the number of human $V_H$ segments provided for the genetic recombination is very small, so that the diversity of the expressed human immunoglobulins is limited. Even if only one $V_H$ segment is recombined, the diversity of the immunoglobulin is assured to some degree because of the combination with D and J genes. However, as mentioned above, since the diversity of immunoglobulins is determined by the rearrangement (random combination) of V gene segments, the more the human $V_H$ segments recombined, the higher the diversity of the immunoglobulins expressed. If the diversity of immunoglobulins is increased, not only antibodies against a number of antigens can be formed, but also the possibility of forming an antibody having a high specificity to a given antigen is promoted. Therefore, it is important for therapies and diagnoses to recombine $V_H$ segments as many as possible.

DISCLOSURE OF THE INVENTION

Accordingly, an object of the present invention is to provide a DNA fragment comprising a plurality of human immunoglobulin $V_H$ segments. Another object of the present invention is to provide a novel human immunoglobulin $V_H$ segments.

The present inventors intensively studied to succeed in determining human immunoglobulin H chain V region gene segments having a size of about 800 kb and in determining DNA sequences of 64 human $V_H$ segments contained therein. This made it possible to provide this DNA fragment of 800 kb and various DNA fragments contained therein, thereby completing the present invention.

That is, the present invention provides a DNA fragment having a size of about 800 kbp and having the structure shown in FIG. 1. It should be noted that in FIG. 1, the 64 human $V_H$ segments are those having DNA sequences shown in Sequence ID Nos. 1, 2, . . . 63, and 64, respectively, in the order from downstream (i.e., from the side near the $J_H$ gene).

The present invention also provides DNA fragments containing at least two consecutive functional human $V_H$ segments which are contained in said DNA fragment of about 800 kb according to the present invention.

The present invention further provides DNA fragments Y20, Y103, Y21, Y6, Y-24, M131, M118, M84 and 3-31, which have been deposited.

The present invention still further provides DNA fragments consisting essentially of at least two optional DNA fragments linked in an optional order, each of which contains at least two consecutive functional human $V_H$ segments contained in the DNA fragment of about 800 kb according to the present invention.

The present invention still further provides DNA fragments consisting essentially of at least two DNA fragments selected from the group consisting of DNA fragments Y20, Y103, Y21, Y6, Y-24, M131, M118, M84 and 3-31 which have been deposited, which are linked in an optional order.

The present invention still further provides novel human immunoglobulin $V_H$ segments having DNA sequences shown in Sequence ID Nos. 6, 7, 8, 9, 10, 11, 12, 13, 14, 15, 16, 17, 18, 19, 20, 21, 22, 23, 24, 25, 26, 27, 29, 30, 31, 32, 33, 34, 35, 36, 37, 38, 40, 41, 42, 43, 44, 45, 46, 47, 48, 49, 50, 51, 52, 53, 54, 55, 63 and 64, respectively.

By the present invention, novel human immunoglobulin $V_H$ segments and DNA fragments containing the same were provided. The DNA fragment of about 800 kb according to the present invention contains as many as 64 human immunoglobulin $V_H$ segments. Thus, by producing human immunoglobulins by a host animal using this DNA fragment, the diversity of the produced human immunoglobulin is largely increased when compared with the conventional methods.

BEST MODE FOR CARRYING OUT THE INVENTION

Figure 1:
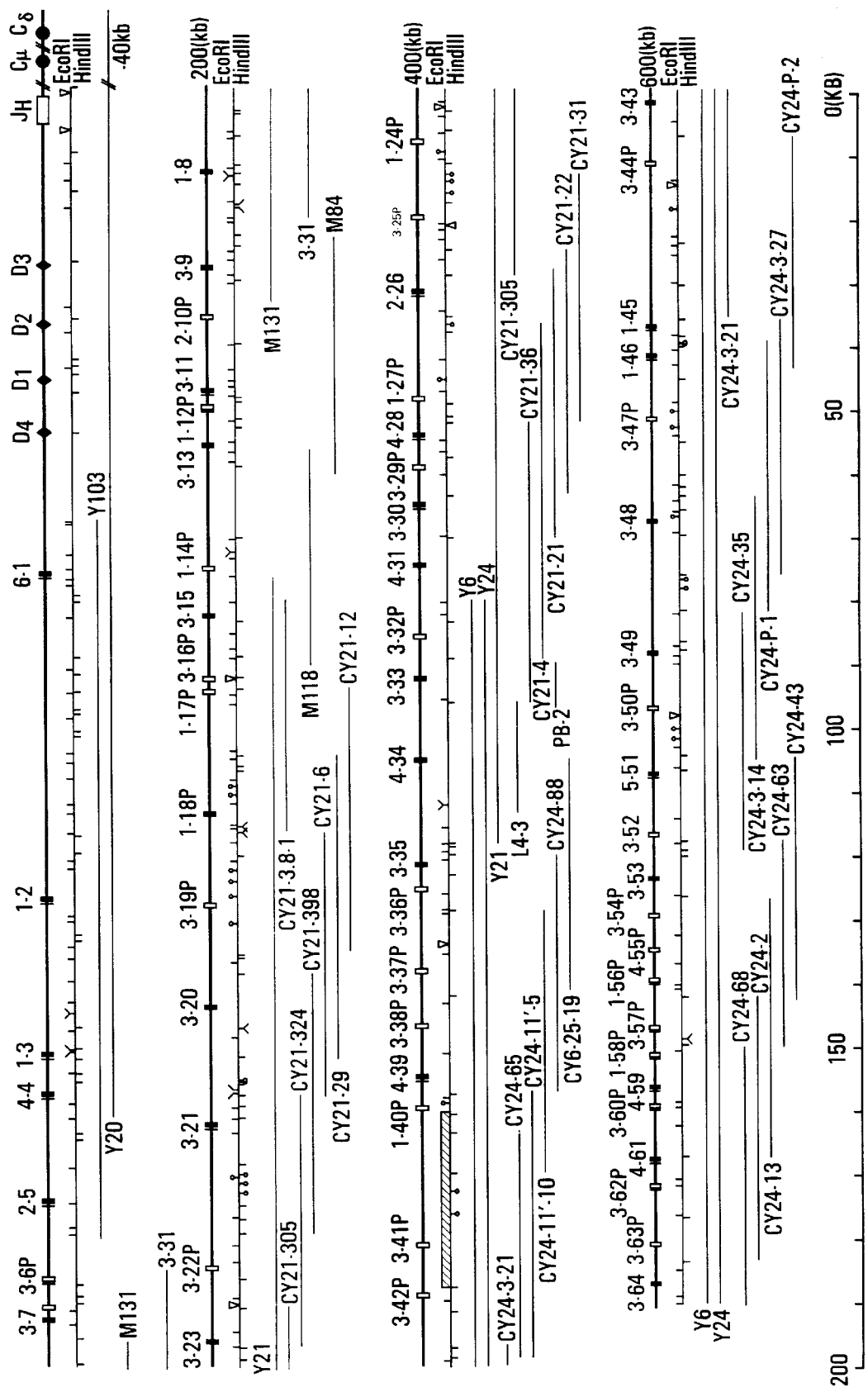
FIG. 1 shows a genetic map of the DNA fragment of about 0.8 Mb according to the present invention.

The present inventors prepared a library by inserting the DNA partially digested with Ecco RI into YAC by the method detailed in the examples hereinbelow described, which DNA was originated from human lymphoblastoid cell line transformed by EB virus, and succeeded in determining the structure of human $V_H$ gene region having a size of about 800 kbp using the above-mentioned library. The structure is shown in FIG. 1. In FIG. 1, the genetic map is shown on the four thick solid lines. The right side of each solid line is the 3' side and the left end of the upper most solid line continues to the right end of the second solid line. In the DNA fragment shown in FIG. 1, there exist C genes, $J_H$ genes and D genes in the order mentioned from the 3' end. Subsequent to the D genes, there are 64 $V_H$ segments. The DNA sequences of all of these 64 $V_H$ segments have been determined as described in the examples below, and Sequence ID Nos. 1, 2, ... 63, 64 were assigned to the 64 $V_H$ segments in the order from downstream. Among these $V_H$ segments, the functional $V_H$ segments which are thought to encode polypeptides are indicated by solid rectangles. On the other hand, those which have the general features of the known $V_H$ segments but do not presently encode polypeptides because of the termination codons; contained therein, that is, pseudo $V_H$ segments are indicated by hollow rectangles. Immediately below the genetic map, restriction maps by Eco RI and Hind III are shown. The restriction sites are indicated by short perpendicular lines. The short lines to which ends circles are attached are those whose order is not determined, and the dotted boxes indicate the regions in which Eco RI sites have not been determined. In FIG. 1, the symbol which looks like "Y" indicates the sites at which two restriction sites are close. In FIG. 1, restriction sites of Mlu I are indicated by hollow triangles and restriction sites of Not I are indicated by solid triangles. The fragments inserted in the clones employed for determining the structure of the DNA fragment are shown thereunder. The structure of the 3' side farther than the 3' end shown in FIG. 1 is known and described in Ravetch, J. V. et al., (1981) Cell, Vol. 27, pp.583–591.

Among the DNA fragments inserted in the clones shown in FIG. 1, the yeasts containing Y20, Y103, Y21, Y6 and Y24 inserted in YAC have been deposited with National Institute of Bioscience and Human-Technology, Agency of Industrial Science and Technology at 1–3, Higashi 1-chrome Tsukuba-shi. Ibaraki, 305 JAPAN on Apr. 22, 1993 under accession numbers FERM BP-4272, FERM BP-4275, FERM BP-4273, FERN4 BP-4271 and FERM BP-4274, respectively. The E. coli cells containing M131, M118, M84 and 3-31, respectively, inserted in cosmids have been deposited with National Institute of Bioscience and Human-Technology, Agency of Industrial Science and Technology at 1–3, Higashi 1-chrome Tsukuba-shi, Ibaraki, 305 JAPAN on Apr. 22, 1993 under accession numbers FERM BP-4279, FERM BP-4278, FERM BP-4277 and FERM BP-4276 respectively.

The DNA fragment having a size of about 800 kbp shown in FIG. 1 can be prepared by linking these deposited DNA fragments by known methods. That is, a DNA fragment A and a DNA fragment B whose DNA sequence at its terminal region overlaps with the DNA sequence of the terminal region of DNA fragment A (i.e., the DNA sequence of the 3' region of DNA fragment A is identical to the DNA sequence of the 5' region of DNA fragment B) can be easily ligated by a method exploiting genetic recombination in the yeast cells. More particularly, DNA fragments A and B are inserted in separate YAC vectors, and the resulting recombinant YAC vectors are introduced in separate mating type yeast cells, respectively. The resulting yeast cells are then fused. By this, genetic recombination occurs in the yeast host to form a YAC having a DNA fragment in which DNA fragment A and DNA fragment B are ligated, which has only one overlapping region located at the terminal regions of DNA fragments A and B. The thus formed recombinant YAC can easily be selected using the auxotrophy encoded in the YAC as a marker. This method is well-known in the art, and is described in, for example, Japanese Laid-open PCT Application (Kohyo) No. 4-504365; Proc. Natl. Acad. Sci. USA, Vol. 87, pp.9913–9917, December 1990; Science Vol. 250, p.94, Proc. Natl. Acad. Sci. USA, Vol. 89, pp.5296–5300, June 1992; and Nucleic Acid Research, Vol. 20, No. 12, pp.3135–3138. Since the terminal regions of each of the deposited 8 DNA fragments overlap the respective terminal regions of the adjacent DNA fragments, they can be ligated sequentially by the method described above. Although DNA fragments 3-31, M84, M118 and M-131 are cloned in cosmid vectors, they can be kept in an artificial chromosome in the yeast cell by cutting the recombinant cosmid with a restriction enzyme having a restriction site only in the cosmid vector, and ligating a YAC vector to the ends of the digested recombinant cosmid vector. Further, by the above-described method, the digested recombinant vector can be ligated to a YAC clone of other regions. It should be noted that even if the above-mentioned 9 deposited fragments are ligated, a gap of about 4 kb still remains. A DNA fragment which fills the gap can be easily prepared by the method described below. That is, as shown in FIG. 1, since the Hind III fragment including the region of the gap is relatively large, this Hind III fragment can be obtained by completely digesting human genome by Hind III, electrophoresing the resultant, selecting DNA fragments having sizes of about 15 kb, detecting the desired fragment with a probe, and recovering the detected desired fragment. The probe used here can be isolated as follows. That is, the DNA fragments located at the both ends of the gap are subcloned using a plasmid and DNA fragments which do not contain a repetitive sequence are prepared therefrom. The thus obtained fragments are then used for screening of the library. Only those detected by the probes which are the DNA fragments at both ends of the gap are isolated.

As described above, the DNA fragment of about 800 kbp shown in FIG. 1 was provided according to the present invention. The fragments consisting of the DNA region included in this DNA fragment can also be used for producing human immunoglobulin by a genetic engineering method. More particularly, to increase the diversity of human immunoglobulin produced by a genetic engineering method, it is preferred to incorporate a fragment containing human $V_H$ segments as many as possible. However, if the fragment contains at least two human $V_H$ segments, the diversity to some degree is given during rearrangement, so that the fragment can be employed. Thus, DNA fragments consisting of a region containing at least two consecutive functional $V_H$ segments, which region is contained in the DNA of about 800 kb shown in FIG. 1 can be employed and are useful. The number of the functional $V_H$ segments contained in such DNA fragments is at least two, and is preferably not less than 6. The more the number of the functional $V_H$ segments, the higher the diversity of the human immunoglobulin produced, so that the more preferred. Thus, the preferableness is increased when the number of the functional $V_H$ segments is 7, 8, 9, 10, 11, 12, 13, 14, 15, 16, 17, 18, 19, 20, 21, 22, 23, 24, 25, 26, 27, 28, 29, 30, 31, 32 and 33, with the order mentioned. Among these fragments, although those having large molecular weights are cloned into YAC vector, small fragments having a size of about not more than 50 kb are not necessarily cloned into YAC vector, but can be cloned into cosmid vectors and plasmid vectors.

Such DNA fragments can be prepared since the information disclosed in FIG. 1 and Sequence ID Nos. 1–64 is available. That is, for example, a DNA fragment containing not less than two functional $V_H$ segments can be obtained by partially digesting human genome with an appropriate restriction enzyme such as Eco RI or Hind III, separating the resulting fragments by electrophoresis, and selecting a DNA fragment containing not less than two desired functional $V_H$ segments using not less than two probes each of which hybridizes with one of the not less than two desired functional $V_H$ segments. Alternatively, amplification by PCR may be employed in place of the detection by the probes. In this case, since the entire DNA sequences of the functional $V_H$ segments are known, the DNA sequences of the primers which should be used are also known, so that the PCR can be carried out easily.

The present invention further provides DNA fragments consisting essentially of optional DNA fragments each of which contains not less than two functional $V_H$ segments which are ligated in optional orders. That is, by ligating a plurality of the DNA fragments each containing not less than two functional $V_H$ segments, the number of $V_H$ segments in the DNA fragment can be increased when compared with the case where only one such DNA fragment containing not less than two $V_H$ segments is used, so that the diversity of the produced immunoglobulin can be increased accordingly. The DNA fragments are not necessarily consecutive, and optional DNA fragments may be ligated in an optional order. In cases where there is no overlapping region between two DNA fragments to be ligated, the above-described method for ligating the DNA fragments having an overlapping region cannot be applied. However, two DNA fragments having no overlapping region can also be ligated by the method as follows.

The left arm vector region and the right arm vector region of a YAC clone containing not less than two functional $V_H$ segments are recovered by the method of Hermanson et al (1991) (Nucleic Acids. Res.,19; 4943–4948). A plasmid (pICL) which has a sequence homologous with the ampicillin-resistant marker (AMP) in the left arm vector region of the YAC, a marker (Lys) which reverse the lysine auxotrophy to the wild type, and a multiple cloning site immediately downstream Lys; and a plasmid (pLUS) which has a sequence homologous with YAC4 region in the right arm vector region of the YAC, the above-mentioned Lys, a kanamycin-resistant marker (KAN), and a multiple cloning site immediately downstream the KAN are linearized and then introduced into yeast cells containing YAC by a conventional method. The plasmids pICL and pLUS cause recombination in the yeast cells at an appropriate frequency, thereby being recombined with the left arm vector region and the right arm vector region of the YAC. The yeast cells carrying such a YAC are selected by using an appropriate selection medium and the YAC in the selected yeast cells is then cut with an appropriate restriction enzyme which has a restriction sites in the multiple cloning sites of the above-mentioned plasmids. By the operation described above, DNA fragments containing the left end or the right end of the DNA fragment originated from human contained in the YAC are recovered as plasmids. After amplifying the thus obtained plasmids in E. coli by a conventional method, the recovered plasmids are digested with a restriction enzyme and then ligated by ligase. The thus ligated DNA fragment is then ligated to the left arm vector region or the right arm vector region of the YAC and introduced into yeast cells carrying the YAC. These YAC vectors causes recombination at a certain frequency between the intrinsic left arm or right arm vector regions and the left end or right end region of the DNA fragment originated from human. By selecting the resulting recombinant vectors, a YAC clone containing a DNA fragment originated from human, which left end is ligated to the right end of another DNA fragment originated from human, and a YAC clone containing a DNA fragment originated from human, which right end is ligated to the left end of another DNA fragment originated from human are recovered. Since these YAC clones have the structure in which the left end or the right end of a DNA originated from human is ligated to the right end or the left end of another DNA originated from human, they can be recombined with a YAC clone having a sequence in the ligated DNA fragments by the method described above.

Further, by optionally ligating the above-described eight actually deposited DNA fragments in an optional order, a large fragment containing a number of $V_H$ segments can be prepared.

By the present invention, the DNA sequencers of the 64 $V_H$ segments contained in the fragment of about 800 kbp shown in FIG. 1 were determined. Amino acid sequences encoded by the DNA of SEQ. ID NOS: 1–13, 15–18, 20–28, 30–31, 33–39, 41, 43–56, and 58–64 are provided respectively in SEQ ID NOS: 89–145. As described in detail in the examples below, among these, 50 $V_H$ segments are novel segments which have DNA sequences that have not hitherto been known. These novel human immunoglobulin $V_H$ segments include pseudo segments which do not encode a polypeptide. Even a pseudo segment has an utility because it may function as a donor of gene conversion in the somatic cell level.

The human immunoglobulin $V_H$ segments and the DNA fragments containing the same according to the present invention can be used for producing human immunoglobulins in a mammalian host as described in, for example, Japanese Laid-open PCT Application (Kohyo) No. 4-504365.

EXAMPLES

The present invention will now be described in more detail by way of examples thereof. It should be noted that the present invention is not limited to the following examples.

Example 1

Determination of Structure of DNA Fragment of About 800 kbp (1) Library Used for Screening The human YAC library screened was constructed from DNA of an Epstein-Barr virus-transformed human lymphoblastoid cell line CGM1 (T. Imai and M. V. Olson, genomics, 8, 297–303 (1990)). Eco RI partial digests of CGM1 DNA were ligated to pYAC4 vector (D. Burkea and M. V. Olson, in "Guide to Yeast Genetics and Molecular Biology" (C. Guthrie and G. R. Fink, eds), p.253, Academic Press, Orlando, 1991), and introduced into AB1380 yeast host strain (D. Burke and M. V. Olson, in "Guide to Yeast Genetics and Molecular Biology" (C. Guthrie and G. R. Fink, eds), p.253, Academic Press, Orlando, 1991). The library consisted of 15,000 independent clones with mean YAC size of about 360 kb. The library thus contained the equivalent of approximately 1.8 haploid human genomes. DNA rearrangement in immunoglobulin H chain (IgH) locus was first checked by Southern hybridization using the human D and $J_H$ probes. The result showed that an allele kept germline configuration while the other was VDJ rearranged.

(2) Primers Used for PCR-Based Screening

For PCR-based screening of human $V_H$ YAC clones, oligonucleotide primers for $V_{H-III}$ and $V_{H-I}$ families, the first and the second largest $V_H$ families, were synthesized. $V_H$ region segments of immunoglobulins contain two hypervariable regions (CDR1 and CDR2) and three framework regions (FR1, FR2 and FR3) (E. A. Kabat et al., Sequences of Proteins of Immunological Interest, Fifth edition, NIH publications, Washington D.C. (1991)). Nucleotide sequences of the framework regions are highly conserved within the same family, suggesting the possibility of oligonucleotide synthesis is for consensus primers corresponding to the framework regions. For this purpose, nucleotide sequences of FR1, FR2 and FR3 regions in all the known $V_H$ sequences were aligned for comparison. Nucleotide sequences corresponding to the first 8 amino acid residues of the FR1 region had extremely high conservation not only within the same family but also between $V_{H-I}$ and $V_{H-III}$ families, which enabled the synthesis of a forward primer F-univ common for the two families as shown in Table 1. Sequences for family-specific reverse primers were independently chosen from conserved sequences in the FR2 region so that 3'-half of the primer sequence has 100% identity to known $V_H$ segments and, in particular, 3'-most nucleotide corresponds to the first letter of the highly conserved/invariant amino acid residues. More particularly, F-univ and I-R, and F-univ and III-R were used as primers for the screening. The DNA sequences of the primers are shown in Table 1.

(3) Optimal PCR Condition Check

Analytical experiments were carried out to determine the optimal condition for specific amplification. A reaction mixture (5 μl) was prepared in accordance with the protocol recommended by Perkin-Elmer/Cetus. Thermal cycling was performed using a DNA Thermal Cycler (Perkin-Elmer/Cetus). Reactions were carried cut using 25 ng of template human DNA under various annealing temperatures (55° C., 58° C., 60° C. and 62° C.) and cyrcles (25, 30, and 35 cycles). As a result, it was found that the reaction under high annealing temperature, namely 94° C., 1 minute—62° C., 2 minutes —72° C., 2 minutes, regardless of cycles, produced specific amplification in human DNA sample but not in yeast strain AB1380 DNA. PCR under low annealing temperature sometimes gave false positive signals in negative control and therefore could not be used. Thus, the PCR was carried out under the above-described conditions.

(4) Polymerase Chain Reaction (PCR)

PCR-based first screening was performed Using synthesized oligonucleotide primers described above against seven multi-filter DNA pools each of which represents the DNA from 1920 colonies (20×96-well) as described (E. D. Green and M. V. Olson, Proc. Natl. Acad. Sci. USA, 87, 1213–1217 (1990)). Positive multi-filter pools were divided into five pools each of which consists of 384 colonies (4×96-well), and further screened by the same procedure. 25 ng each of YAC pool DNAs were used for reaction. DNA of CGM1 whose DNA was used to construct the YAC library, and of the yeast strain AB1380 were included during the PCR analysis as positive and negative controls, respectively. After the amplification, the entire sample was analyzed by electrophoresis in 10% polyacrylamide gels containing 15% glycerol and visualized by ethidium bromide staining.

(5) Colony Hybridization

After PCR-based first and second screening, the location of the positive clone within the 384-clone array was established by conventional colony hybridization. The nylon filters consisting of 384 YAC clones were prepared by a known method (D. Burke and M. V. Olson, in "Guide to Yeast Genetics and Molecular Biology" (C. Guthrie and G. R. Fink, eds), p.253, Academic Press, Orlando, 1991). $V_{266BL}$ (Y. Nishida, et al., Proc. Natl. Acad. Sci. USA, 79, 3833–3837 (1992)) and $V_{HBV}$ (M. Kodaira et al., J. Mol. Biol., 190, 529–541 (1986)) were used for probes representative for human $V_{H-I}$ and $V_{H-III}$ families, respectively. These probes were labeled ($5\times10^5$ cpm) with $^{32}$P-dCTP using Oligolabeling Kit. (Pharmacia) and subjected to colony hybridization according to standard procedure (D. Burke, et al., supra). After the hybridization for 12 hours at 65° C., filters were washed twice with 2×SSC (1×SSC is 0.15 M NaCl-15 mM sodium citrate) for 10 minutes at room temperature, then twice with 0.2×SSC–0.1% SDS for 30 minutes at 65° C. Filters were exposed overnight and corresponding positive YAC clones were picked up for further characterization.

(6) Insert Check by Colony PCR

To test the presence of specific DNA sequence in isolated YACs, simple and rapid rescreening of colony-purified clones was carried out by using PCR without DNA purification (E. D. Green and M. V. Olson, Proc. Natl. Acad. Sci. USA, 87, 1213–1217 (1990)). That is, the positive yeast clones were streaked onto AHC plates and grown. Four each of single colonies from each clone were transferred by toothpick into 5 μl of PCR mixture described above. PCR and following gel electrophoresis were performed for identification of the amplified bands under the same condition as that used for screening. In most of the clones, all of the four colonies gave rise to specific amplification of DNA fragments.

(7) Sizing of YAC Clones Using PFGE

Figure 2:
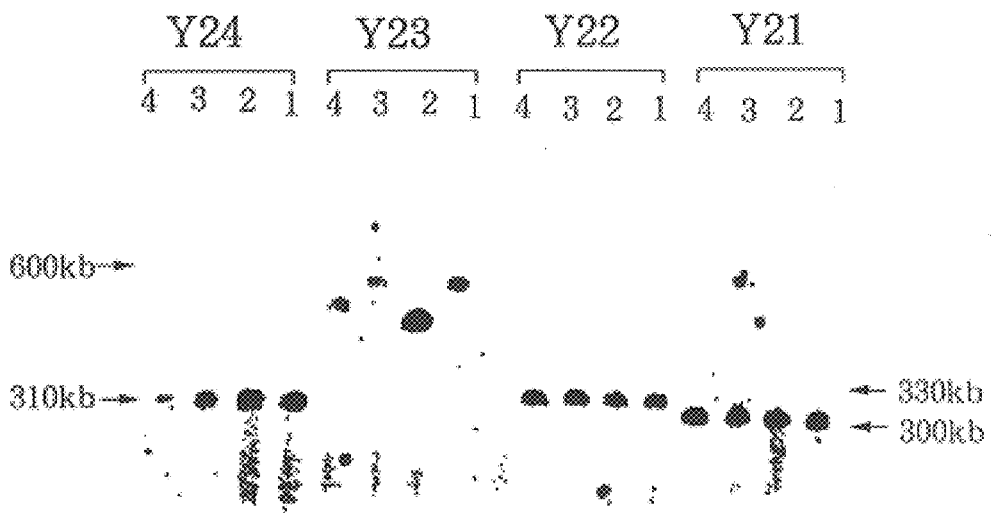
FIG. 2 shows the results of Southern hybridization of a representative DNA inserted in YAC.

Many researchers claimed that some YACs are clonally unstable due to intrachromosomal rearrangement during the growth in culture resulting in size variation of the human DNA insert. This artifact is considered to be often mediated by repetitive sequences or tandem repeat of homologous DNA sequences in the insert DNA. Since $V_H$ locus contains a number of homologous DNA fragments consisting of $V_H$ gene segments and their flanking regions, such kind of rearrangement can take place at considerable frequency. An additional problem is the presence of single yeast containing more than one insert YACs. In order to exclude the artifact clones for subsequent analysis and to identify YAC clones with multiple insert, the sizes of the YAC clones were first determined by pulse field gel electrophoresis (PFGE). The same four $V_H$-positive single colonies checked by PCR were selected from 17 colonies originating from a single well, and miniprepared from 5 ml culture in AHC medium to give low-gelling temperature agarose blocks by a known method (D. Burke et al., supra). Appropriate sized piece of agarose block was used for sizing the YACs by PFGE with a Pulsaphor (Pharmacia) or a Crossfield (ATTO, Tokyo, Japan) gel electrophoresis apparatus at 60 second pulse time. Concatamerized lambda DNA was also loaded as a size standard. After the electrophoresis, DNAs were transferred to nitrocellulose filter and subjected to Southern hybridization using pBR322 plasmid as a probe. Typical result is shown in FIG. 2. All of the four colonies selected from each of clones Y21, Y22 and Y24 having DNA inserts with a size of 300 kb, 330 kb and 310 kb, respectively exhibited the same size, so that they seemed to have no recombination. On the other hand, since four colonies selected from clone Y23 held DNA inserts with different sizes, the insert of the clone Y23 looked rather unstable due to frequent recombination. Therefore, the colony which did not cause recombination was selected for the subsequent analysis. All but 3 clones including clone Y23 of 17 $V_H$-carrying YAC clones including the analyzed $V_H$ displayed instability of human inserts. Subsequent analysis revealed that such recombination took place regardless of the number of $V_H$ segments in the insert DNA, indicating some other factors might be involved in homologous recombination. From 14 stable YAC clones among the 17 YAC clones containing $V_H$, Y20, Y103, Y21, Y6 and Y24 were selected and used for the subsequent physical mapping.

(8) Physical Mapping of YAC Clones with Rare Site Endonucleases

Gel blocks were prepared from the YAC clones after sizing and were used for physical map construction by PFGE. In general, detailed physical map using several enzymes might be required for long-range YAC analysis. In this example, however, only two rare-site restriction enzymes (i.e., restriction enzymes whose restriction sites occur relatively rarely), namely Not I and Mlu I, were used for overlapping analysis of the YAC clones mainly by the following two reasons: 1) $V_H$-carrying YAC clones can be arrayed with several other information such as comparison of the size or the pattern of the fragments hybridized with $V_H$ probes or non-repetitive probes isolated from $V_H$-carrying cosmid clones, 2) it is necessary to subclone the YACs into cosmids for detailed structural analysis including construction of physical maps using ordinary restriction enzymes.

Gel blocks digested in completion with Not I or Mlu I were electrophoresed with a PFGE apparatus using a pulse time of 30 to 60 seconds depending on the length of YAC. Mixtures of lambda phage DNA, its Xho I digests and Hind III digests were also used as low molecular weight size markers. Southern filters were first hybridized with total human large molecular DNAs for detection of all restricted fragments. The sizes of detected bands were summed up to fit the length of undigested YAC insert. Filters were hybridized consecutively with pBR322 DNA probes corresponding to each of the pYAC4 arms. A Pvu II and Bam HI double digest of pER322 results in a 2.67-kb and 1.69-kb fragments which hybridize specifically to the left (trp) and the right (ura) end of YACs, respectively. Filters were also hybridized with six $V_H$ family-specific probes for the presence of $V_H$ segments in digested DNA fragments. Origin of $V_H$ family-specific probes for $V_{H-II}$, $V_{H-IV}$, $V_{H-V}$ and $V_{H-VI}$ families, respectively, are; $V_{CE-1}$ (N. Takahashi et al., Proc. Natl. Acad. Sci. USA, 81, 5194–5198 (1984)), $V_{71-2}$ (K.H. Lee et al., J. Mol. Biol., 195, 761–768 (1987)), 5-1R1 (J. E. Berman et al., EMBO J. 7, 727–1051 (1988) and 6-1R1 (J. E. Berman et al., EMBO J. 7, 727–1051 (1988)).

In order to array Not I and Mlu I fragments detected by the complete digestion experiments, hybridization experiments using partially digested YAC DNA were carried out. Analytical experiment was necessary to determine the optimal condition for partial digestion since the efficiency of the restriction enzyme reaction is highly dependent on the purity of DNA. In the DNA preparation in this example, 6-hour incubation with 1 unit of restriction enzyme was, in most cases, sufficient for complete digestion of a gel block (about 500 ng of DNA). Partial cleavage of DNA was achieved by varying the time of digestion as follows:

1. Dialyze three gel blocks (about 50 μl each volume containing about 1 μg of DNA, stored in 0.5 M EDTA (pH 8.0)) for 1 hour against 50 ml of distilled water at room temperature with gentle agitation. Repeat this step for complete removal of EDTA.
2. Equilibrate the blocks with 10 ml appropriate digestion buffer at 37° C. for 30 minutes.
3. Transfer each block to 250-μl reaction mixture containing 1 unit each of restriction enzyme in 1× digestion buffer.
4. Incubate all three tubes for 10 minutes, 30 minutes and 1 hour at 37° C.
5. Stop the reaction by adding 100 μl of 0.5 M EDTA (pH 8.0).
6. Equilibrate the blocks with appropriate gel electrophoresis buffer 2–3 times over a 1 hour period and immediately perform PFGE using an appropriate pulse time.

Figure 3A:
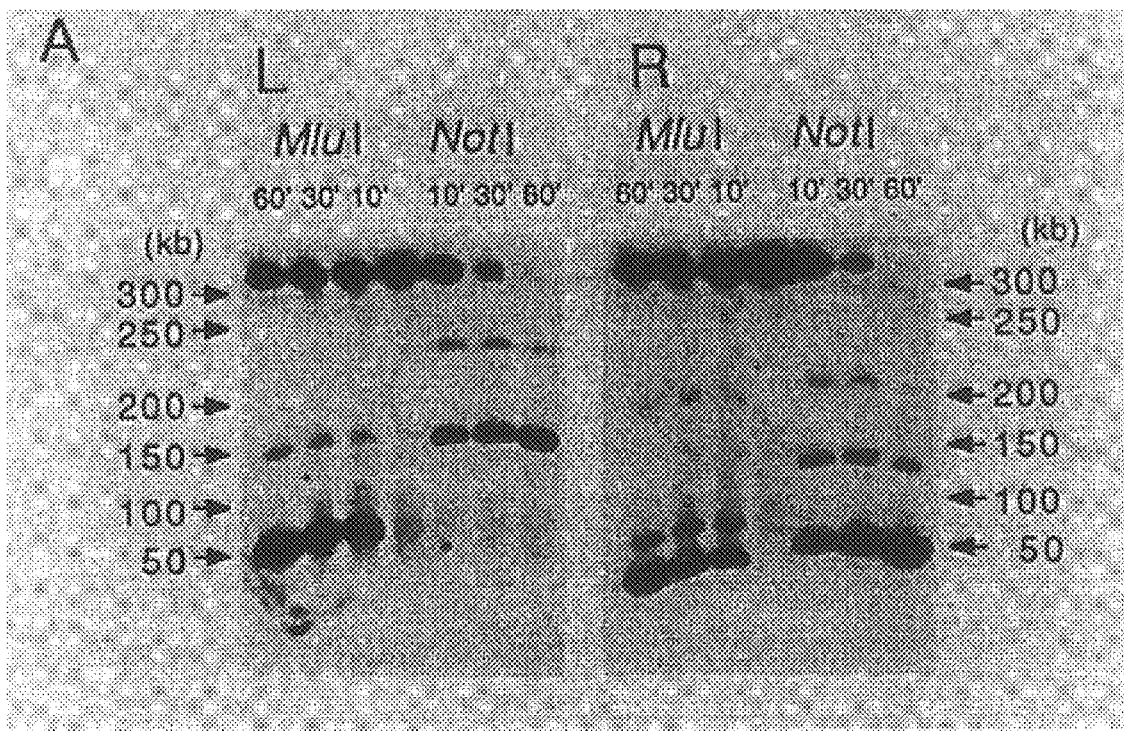
FIG. 3A shows the results of Southern hybridization of the fragment digested with restriction enzymes Mlu I and Not I.
Figure 3B:
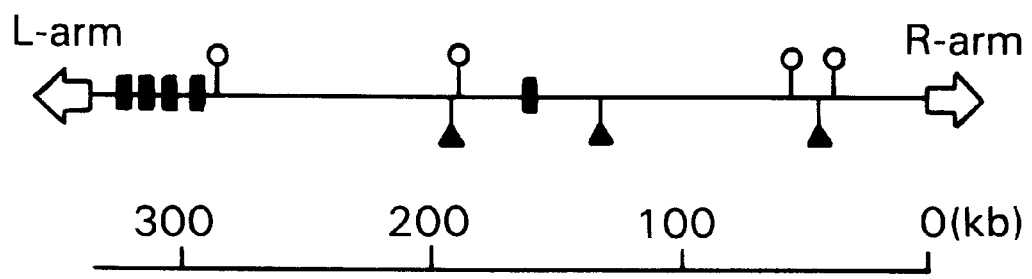
FIG. 3B shows a physical map of a YAC clone constructed based on the results shown in FIG. 3A.

Filters were hybridized with the above-described right- or left-end probe of YAC vector and the size of the hybridized restriction fragments was determined by comparison with size standards (FIG. 3A). Results from complete and partial digestion experiments were combined to construct a physical map of YAC clones shown in FIG. 3B. Mapped clones were thus linked and classified into several contigs.

(9) Isolation of Insert-terminal Sequences from YACs

After isolated YAC clones were classified into several contigs based on their restriction maps, insert-terminal DNA segments were isolated from both ends of each contigs to synthesize oligonucleotide primers. As is often pointed out, considerable percentage (up to 30%) of YAC clones in libraries contain noncontiguous DNA segments spliced together resulting in "chimeric clone". Since no good strategies have been developed to exclude coligation artifact during the construction of the library, it is necessary to check this possibility with appropriate method after isolation of YAC clones. In this example, the strategy to investigate the possibility by using PCR with synthesized insert-terminal primers was taken. The reason is that the synthesized primers would be useful not only to investigate chimeric clones but also to register resulting sequences as sequence tagged sites (STS) for rescreening the YAC library by PCR. In addition, they could be used to look for overlaps between contigs which could not be found by comparison of their restriction maps.

For isolation of insert-terminal YAC segments, several different methods can be employed including more sophisticated and rapid method by inverse PCR and the Vectorette system (J. H. Riley et al., Nucleic Acids Res., 18, 2887–2890 (1990)). However, in this example, a rather classical way, that is, to subclone the fragments with plasmid or lambda phage vectors was taken. High molecular weight DNA from YAC clones was digested with restriction enzymes which have recognition sites both in right- and left-arm sequences. Gel electrophoresis was performed in a 0.7% agarose gel and Southern filter was hybridized with a 0.62-kb Hind III—Sal I fragment of pBR322 DNA ($Tet^R$) which specifically hybridizes with insert-vector boundary sequence of pYAC4 vector. The DNA fractions of interest were recovered from the gel using DE81 paper and ligated to either EMBL4 or pUC19 vector depending on the insert size. Isolated fragments with EMBL4 vector were subcloned into pUC19 vector for subsequent sequencing. The chain termination method with M13 forward or reverse primer was used for sequencing these plasmid clones. Sequences for insert-terminal primers were provided from the non-repetitive portion in the resulting sequence.

PCR experiments were achieved to investigate the above-mentioned artifact using primers at the both ends of YAC-DNA against the DNA from a human mouse somatic cell hybrid GM10479 line (Colier Institute) which carries human chromosome 14 alone in which the human IgH locus exists. DNA from CGM1 cells (source of YAC library) and Rag cells (mouse cell) were also used as positive and negative controls, respectively. PCR was carried out in 25-µl reactions according to a known method (H. S. Kim and O. Smithies, Nucleic Acids Res., 16, 8870–8903 (1988)). 200 ng each of DNA was used for the reaction. Incubations containing DNAs from GM10479, CGM1 and Rag, respectively were subjected to 35 to 40 cycles at 95° C., 1 minute—55 to 62° C., 2 minutes—72° C., 2 minutes according to the condition optimized by analytical experiment using CGM1 DNA. The YAC clones of which either of the two insert-terminal primers gave no specific amplification against GM10479 were concluded to be chimeric clones. Only one contig neither of which primers gave amplified bands was turned out to cover orphan $V_H$ locus on chromosome 16.

(10) Cosmid Subcloning and Construction of Physical Maps

Isolation of large chromosomal region using YAC system is advantageous for the initial step of physical mapping. However, subsequent step to analyze large DNA fragments in YAC can be problematic since exogenous DNA inserts cannot be easily separated from yeast chromosomal DNA and fragments up to several hundred kb are difficult to handle without mechanical shearing. In order to map $V_H$ segments of a large DNA fragment containing $V_H$ segments, detailed restriction map using common 6bp-site restriction enzyme is necessary. For this purpose, YAC clones were subcloned into cosmids. Cosmid libraries were constructed from whole YAC DNA without previous separation of cloned DNA from host chromosome. There are two major reasons for this: 1) separation of intact insert DNA and their manipulation are difficult, 2) 4000 independent colonies are sufficient for complete coverage of YAC insert since the genome size of yeast is about $1.5 \times 10^4$ bp, 1/200 of that of human.

In general, there are two major difficulties in the construction of cosmid libraries. The first is self-ligation of vector DNAs, resulting in generation of clones carrying no inserts of foreign DNA, and the second is insertion of more than one DNA fragments in a single vector, namely co-ligation artifact. To overcome these problems, great efforts have been made including construction of better-designed vectors with two cos sites and modified method for ligation such as partial filling of vector and insert DNAs (J. Sambrook et al., A Laboratory Manual, Cold Spring Harbor Laboratory Press, Cold Spring Harbor, N.Y. (1989)). Size fractionated insert DNA usually contains smaller DNA molecules trapped among larger molecules especially when excess amount of DNA was loaded in the preparative gel. Alkaline phosphatase treatment of insert DNA is effective in order to exclude the co-ligation between inserts but gives rise to polymerized vector DNA during the ligation step, which causes high background of empty colonies under the antibiotic selection. In this example, however, less than 5 µg of YAC DNA was sufficient for insert preparation and thus preparative gel electrophoresis was successful without contamination of smaller DNA fragments. Most of the cosmid libraries were thus constructed with minimal steps in combination with alkaline phosphatase-treated cosmid vector and partially digested DNA of exact size range for cosmid insert (from 35 kb to 45 kb).

① Preparation of Yeast DNA Containing YAC

Since large DNA fragments are required as starting material for preparing the DNA, extraction of ENA from yeast cells with minimal shear damage is one of the most critical steps. Obviously, the best way is to manipulate DNA in-gel because DNA is fully protected from shear damage. The present inventors found, however, that gentle extraction of DNA in liquid from yeast cells gives sufficient length of DNA (>200 kb) for partial digestion and subsequent size fractionation. In addition, liquid DNA is easier to control the condition for partial digestion than gel block DNA. With a simple and rapid (6 hours for total procedure) method described below, about 50 µg of large size DNA (>200 kb) can be routinely purified from 100-ml yeast culture.

(i) Spin down yeast cells and wash them with TE (10 mM Tris HCl (pH 8.0)—1 mM EDTA) twice.

(ii) Resuspend the cells in 20 ml of 0.1 M EDTA (pH 7.5), 1 M sorbitol, 0.2 mg/ml of Zymolyase 100T (ICN Cat#152270), 15 mM 2-mercaptoethanol. Incubate at 37° C. for 1 hour to form spheroplasts.

(iii) Spin down the spheroplasts and resuspend in 9 ml of 0.1 M Tris HCl (pH 7.5), 50 mM EDTA (pH 7.5).

(iv) Add 1 ml (1/10 final volume) of 10% SDS and mix gently. Incubate at 60° C. for 10 to 20 minutes.

(v) Add ⅓ volume of 4 M potassium acetate and mix gently. Leave on ice for 30 minutes.

(vi) Centrifuge at 2000×g for 30 minutes and transfer the supernatant to a new tube. Add 3 volumes of isopropanol and mix gently. Leave at room temperature for 10 to 20 minutes for precipitation of DNA.

(vii) Centrifuge again at 2000×g for 30 minutes and discard supernatant. Dissolve the pellet in 10 ml of water.

From-this step onwards, care should be taken not to give shear damage to the DNA.

(viii) Extract with phenol twice and with CIAA (chloroform:isoamyl alcohol=24:1) twice followed by ethanol precipitation at room temperature for 10 to 20 minutes.

(ix) Centrifuge at 2000×g for 30 minutes. Rinse the pellet with 70% ethanol and dry up the pellet.

(x) Dissolve with 1 ml of TE.

② Vector DNA Preparation

Lorist 2 DNA was linearized by digestion with Hind III or Bam HI. Linearized DNA was dephosphorylated by treatment with bacterial alkaline phosphatase. Small aliquots of DNA before and after phosphatase treatment were used for test ligation for phosphatase treatment according to a known method (J. Sambrook et al., supra).

③ Insert DNA Preparation

Analytical experiment of partial digestion of yeast DNA was performed according to standard procedure (J. Sambrook et al., supra) to determine the optimal enzyme concentration and reaction time. Preparation of size-fractionated DNA from the gel was achieved with LGT agarose and β agarase I. This very gentle method resulted in high recovery (>90%) of fractionated DNA without degradation. Scaled up cleavage reaction was done using 5 µg of DNA with optimal enzyme concentration. Digested samples were loaded in a preparative gel of 0.5% LGT agarose (Bio Rad Preparative grade) at about 1 V/cm overnight. Linearized lambda DNA and its Xho I-digests which give 35-kb and 15-kb bands were also loaded as size markers. After visualizing the DNA under ultraviolet transilluminater, a small slice of agarose containing the fraction ranging from 35 kb to 45 kb was cut out. Recovery of the DNA from the gel slice was achieved using β agarase I (NEB) as follows:

(i) Equilibrate the gel block with water for complete removal of gel electrophoresis buffer.
(ii) Transfer the block to a new tube and add 1/9 volume of 10×β agarase I buffer.
(iii) Melt the gel at 68° C. for 10 minutes. Cool to 40° C. and incubate the molten agarose at 40° C. for 1 hour with optimal number of units of β agarase I.
(iv) Adjust the salt concentration of the solution to 0.5 M NaCl for ethanol precipitation. Chill on ice for 10 minutes.
(v) Centrifuge at 15,000×g for 15 minutes to pellet any remaining undigested carbohydrates.
(vi) Transfer the DNA-containing supernatant to a new tube. Precipitate the DNA with 3 volumes of ethanol at −80° C. for 10 minutes.
(vii) Centrifuge at 15,000×g for 15 minutes and remove the supernatant. Rinse the pellet with 70% ethanol and dry up the pellet.
(viii) Resuspend the pellet in appropriate volume of water for subsequent manipulation.

With this method, in average 100 to 300 ng of size-fractionated DNA can be recovered.

④ Ligation, in vitro Packaging and Infection to *E. coli*

This process was performed according to standard procedure (J. Sambrook et al., supra). By using lambda inn packaging kit (Nippon Gene) and ED8768 host strain, about 10,000 colonies were obtained from 25 ng of ligated DNA.

⑤ Screening of Cosmid Libraries

Initial screening was carried out using Hind III-partial cosmid libraries. About 10,000 colonies (500 colonies per φ10 cm plate×20) were plated on LB plates containing 50 μg/ml of kanamycin so that single colonies can be picked up after first screening. Colonies were then lifted from the plates with φ8.2 cm detergent-free nitrocellulose membranes (Advantec Toyo Membrane) and subjected to colony hybridization. Three different kinds of probes were used for screening, namely mixture of six $V_H$-family specific probes to isolate $V_H$-containing cosmid clones, YAC vector probes ($Tet^R$ gene segment of pBR322, described above) for isolation of insert-terminal cosmid clones, and total human DNA for any remaining cosmid clones. In average, 50 to 100 clones from a YAC clone with approximately 300-kb insert were isolated with the probes.

⑥ Construction of Cosmid Contigs

DNA from cosmid clones was isolated by the alkaline lysis method by a conventional method (J. Sambrook et al., supra). Purified cosmid DNAs were digested with Eco RI or Hind III and subjected to agarose gel electrophoresis for restriction mapping. Overlaps between clones were easily found by comparing restriction patterns among cosmid clones. Ordered cosmid clones were then cleaved with Eco RI or Hind III and loaded in a 0.7% agarose gel. Southern filters were hybridized with six $V_H$-family specific probes for identification of location and number of $V_H$ segments in cosmid clones. Filters were washed three times for 30 minutes under standard conditions (at 50° C. in 1×SSC, 0.1% SDS) followed by stringent conditions (at 65° C. in 0.1×SSC, 0.1% SDS). Location of $V_H$ segments were determined by comparison between hybridization pattern of cosmids and their physical maps.

Figure 4:
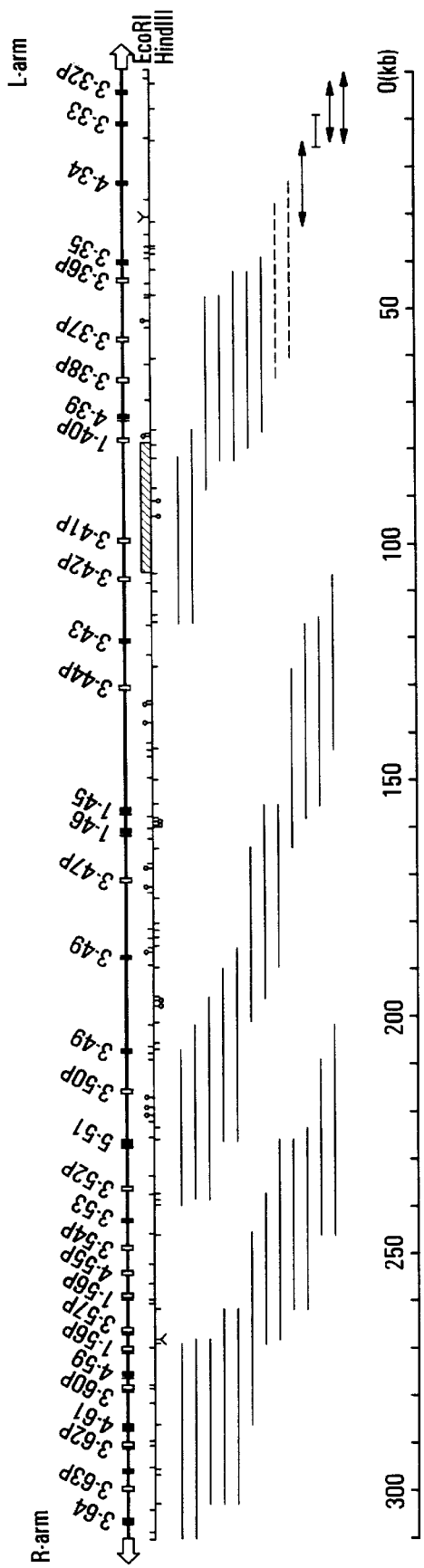
FIG. 4 shows a genetic map of YAC clone Y6.

Theoretically, approximately 50 independent cosmid clones (about 7 fold of the whole YAC insert) would be sufficient to cover the whole YAC insert of 300 kb in length. However, the distribution of cosmid clones were uneven and there still remained a few gaps. The clones corresponding to the gaps could not be isolated even after screening of Sau 3AI partial library or chromosomal walking by using the probes isolated from the edge of each contig. Regions not present in the cosmid libraries were subcloned with phage or plasmid vectors by isolation of DNA fragments of required size from YAC DNA as shown in FIG. 4. After the complete physical map was constructed, the present inventors found out that this was not due to the nonrandom distribution of restriction sites within the YAC insert. The presence of some classes of sequences such as palindromic or tandem repeat DNA might make these regions unclonable or under-represented by using cosmid system. The complete physical map of the 0.8-Mb region constructed in this example is shown in FIG. 1 as mentioned above. The distance from $J_H$ of each $V_H$ segment shown in FIG. 1 and the sizes of Eco RI and Hind III fragments are shown in Table 3.

Example 2

Construction of Cosmid Clones

A cosmid library was constructed from human high molecular DNAs as follows:

3-31: High molecular DNAs obtained from human placenta were partially digested with Taq I and the resultant was subjected to electrophoresis on 0.5% agarose gel. The 35–45-kb bands were recovered by using DEAE paper. The recovered DNAs were treated with alkaline phosphatase and the resultant was ligated to cosmid vector pJB8 which had been completely digested with a restriction enzyme Cla I. The ligation product was subjected to in vitro packaging and the resultant was infected to host *E. coli* 490A, followed by the screening by the conventional colony hybridization to obtain the clone.

M131, M84 and M118: These fragments were obtained by the same method as for 3-31 except that the DNA used was human pro B cell line FLEB14-14, the vector and the host *E. coli* used were Lorist 2 and ED8767, respectively, the combination of restriction enzymes employed was Xba I and Hind III, and the edges of the fragments were modified by the partial repairing. The partial repairing was carried out according to a known method (J. Sambrook, E. F. Fritsch and T. Maniatis, 1989, Molecular Cloning; a Laboratory Manual, Cold Spring Harbor Laboratory Press, Cold Spring Harbor, N.Y.).

Example 3

Sequencing Analysis of $V_H$ Segments

Instead of sequencing subcloned $V_H$-containing DNA fragments using vector primers, $V_H$ family-specific oligonucleotide primers were synthesized. As mentioned above, nucleotide sequences of FR regions of $V_H$ segments are highly conserved within the same family, so the present inventors selected consensus sequences from the conserved portions and synthesized family-specific oligonucleotide primers for sequence analysis. For this purpose, automated fluorescence-based sequencing system Model 373A developed by Applied Biosystems was employed. Dye-Deoxy terminator sequencing kit supplied from the same company using fluorescent-dye labeled dideoxy nucleotides was suitable for our purpose since synthesized $V_H$-specific primers could be directly used without fluorescence-label.

(1) Subcloning of $V_H$-containing Restriction Fragments

In order to use $V_H$-family specific primers for sequencing, it is essential to subclone $V_H$-containing DNA fragments so that each plasmid contains only one $V_H$ segment. Several other 6bp-site enzymes than Eco RI and Hind III were used to isolate single $V_H$-carrying DNA fragments. Plasmid DNA of the subcloned fragments was isolated by alkaline lysis method followed by ultracentrifugation twice to obtain high quality DNA samples for accurate sequences.

(2) Oligonucleotide Synthesis for Sequencing

To select consensus sequences for $V_H$ family-specific oligonucleotide primer synthesis, nucleotide sequences of framework regions and exon-intron boundaries of the known $V_H$ segments were aligned by family. Attention was paid so that 3'-half of them have 100% identities to reference sequences and 3'-most nucleotide corresponds to the first or the second letter of highly conserved/invariant amino acid residues. Nineteen additional primers were designed for five $V_H$ families as shown in Table 1 (described below).

(3) Sequencing Reaction and Gel Electrophoresis

The sequencing reaction was performed by PCR using Dye-Deoxy terminator sequencing kit (ABI) according to manufacturer's instruction. Gel electrophoresis and detection of signals were done in the sequencing apparatus according to the users manual of the system. In average, sequences of over 350 bases were obtained from each reaction.

(4) Evaluation of Synthesized $V_H$ Family-Specific Primers

The primers F-univ and I-R were first chosen to sequence $V_{H-I}$ segments. As shown in Table 2, they annealed 11 of 12 $V_{H-I}$ segments analyzed. It is to be noted that all of 6 functional $V_{H-I}$ segments could be sequenced with these two primers. Two more primers, I-NF1 and I-NR1 were designed for V1-14P and V1-27P segments. These two primers were also used for some other $V_H$ segments to verify their sequences obtained by first two primers (Table 2).

Eight primers were designed and used for sequencing $V_{H-III}$ family segments. The first sequencing reaction of each $V_H$ segment was performed with F-univ and III-R primers. They annealed more-than 80% of the $V_{H-III}$ segments analyzed (25/30 for F-univ and 24/30 for III-R) (Table 2). Importantly, again, all the functional $V_{H-III}$ segments with one exception could be sequenced with this combination of primers, suggesting that they would be good for most of $V_{H-III}$ cDNA. Based on the nucleotide sequences obtained from first experiment, six additional primers (III-F3, III-R3, III-F4, III-R4, III-NF1 and III-F2) were designed and appropriate combination among them were used for further analysis. Among these, III-R3 and III-F4 were used to determine the sequence of 5' regulatory region and 3' flanking region, respectively. V3-29P and V3-32P were pseudogenes with extensive divergence in their sequences and thus all but. III-NF1 failed to anneal these two $V_H$ segments. Sequences of V3-25P, V3-44P and V3-63P were determined using M13 vector primers from their internal restriction sites.

Five each of synthesized primers were used to determine the sequences of $V_H$ segments belonging to $V_{H-II}$, $V_{H-IV}$ and $V_{H-V}$ families. Since $V_H$ segments belonging to each of these three families are highly homologous with each other, it was thought that four each of the primers are enough for most of the $V_H$ segments belonging to these smaller $V_H$ families. In fact, all four $V_{H-II}$ family-specific primers annealed three $V_{H-II}$ segments (V2-5, V2-10P and V2-26). In brief, in total 11 primers (F-univ and I-R for $V_{H-I}$; II-R1, II-F2 and II-R:2 for $V_{H-II}$; F-univ and III-R for $V_{H-III}$; IV-R1, IV-F2 and IV-R2 for $V_{H-IV}$; V-R2 and V-R3 for $V_{H-V}$) would be sufficient for sequencing most of the $V_H$ segments belonging to five $V_H$ families. The II-F1, III-NF2 and IV-F1 primers contain intron sequences and thus cannot be used for cDNA sequencing.

By this procedure, the DNA sequences of the 64 $V_H$ segments were determined and they are shown in Sequence ID Nos. 1–64 as mentioned above. The distance of each $V_H$ segment from $J_H$ and the sizes of Eco RI and Hind III fragments are summarized in Table 3.

(5) Transcriptional Polarities of $V_H$ Segments

The strategy for sequencing $V_H$ segments with family-specific primers was not suitable for determination of transcriptional polarities of the $V_H$ segments because it did not require restriction map of single $V_H$-containing subcloned fragments. The present inventors could not determine orientations of all the $V_H$ segments within this region for that reason. The present inventors found, however, that 8 regions containing 21 $V_H$ segments were already isolated in cosmid or phage clones since sequences between corresponding $V_H$ segments as well as their restriction maps were identical with each other. As the relative orders of these 21 $V_H$ segments within these clones are identical to those in the 0.8-Mb region, it was concluded that the orientation of these 21 $V_H$ segments are the same as those of the $J_H$ segments.

TABLE 1

VH family-specific primers used for screening and sequencing

| FAMILY | NAME | SEQUENCE (5' to 3') | *LOCATION | DIRECTION | SEQ ID NOS |
|---|---|---|---|---|---|
| I, III, V | F - univ | AGGTGCAGCTGGTGCAGTCTG | 1–8 | forward | 65 |
| I | I - R | CCAGGGGCCTGTCGCACCCA | 36–42 | reverse | 66 |
|  | I - N F 1 | TGGGGCCTCAGTGAAGGTCTCCTG | 14–22 | forward | 67 |
|  | I - N R 1 | GATCC(A/G)TCCCATCCACTCAAG | 45–51 | reverse | 68/69 |
| II | II - F 1 | TGTCTTCTCCACAGGGGTCTT | intron-(-2) | forward | 70 |
|  | II - F 2 | GGGAAGGCCCTGGAGTGGCT | 42–48 | forward | 71 |
|  | II - R 1 | GTGCAGGTCAGCGTGAGGGT | 17–23 | reverse | 72 |
|  | II - R 2 | TGGTTTTTGGAGGTGTCCTTGG | 70–77 | reverse | 73 |
| III | III - R | CACTCCAGCCCCTTCCCTGGAGC | 40–47 | reverse | 74 |
|  | III - F 3 | GTGAGGTTCAGCTGGTGGAGT | (-I)–7 | forward | 75 |
|  | III - R 3 | AGCTGAACCTCACACTGGAC | (-3)–4 | reverse | 76 |

TABLE 1-continued

VH family-specific primers used for screening and sequencing

| FAMILY | NAME | SEQUENCE (5' to 3') | *LOCATION | DIRECTION | SEQ ID NOS |
|---|---|---|---|---|---|
| | III - F 4 | AAGGGCCGATTCACCATCT | 64—70 | Forward | 77 |
| | III - R 4 | TTGTCTCTGGAGATGGTGAA | 68—73 | reverse | 78 |
| | III - N F 1 | TGAGACTCTCCTGTGCAGCCTCTG | 18—26 | forward | 79 |
| | III - N F 2 | TCT(T/C)TGTGTTTGCAGGTGT | intron-(-3) | forward | 80/81 |
| IV | IV - F 1 | TCTGTTCACAGGGGTCCTGTC | intron-(-I) | forward | 82 |
| | IV - F 2 | TCCGGCAGCCCCCAGGGAA | 37—43 | forward | 83 |
| | IV - R 1 | GCAGGTGAGGGACAGGGT | 17—22 | reverse | 84 |
| | IV - R 2 | CAGGGAGAACTGGTTCTTGGA | 74—80 | reverse | 85 |
| V | V - R 1 | CCCGGGCATCTGGCGCACCCA | 36—42 | reverse | 86 |
| | V - R 2 | GCTGCTCCACTGCAGGTAGGC | 78—82R | reverse | 87 |
| | V - R 3 | CTTCAGGCTGCTCCACTGCAG | 74—83 | reverse | 88 |

*Locations of the primers are indicated as amino acid residue number according to Kabat et al. Bases with redundancy are shown in the parentheses. Directions relative to coding sequence are also shown.

TABLE 2

List of useful primers for sequencing V$_H$ clones

| V$_H$ segments | V$_{H-I}$ primers | | | | V$_{H-III}$ primers | | | | | | | | V$_{H-IV}$ primers | | | |
|---|---|---|---|---|---|---|---|---|---|---|---|---|---|---|---|---|
| | univ | R | NF1 | NR1 | univ | R | F3 | R3 | F4 | R4 | NF1 | NF2 | F1 | R1 | F2 | R2 |
| V$_H$ I | | | | | | | | | | | | | | | | |
| 1-2 | + | + | | | | | | | | | | | | | | |
| 1-3 | + | + | | | | | | | | | | | | | | |
| 1-8 | + | + | | | | | | | | | | | | | | |
| 1-12P | + | + | | | | | | | | | | | | | | |
| 1-14P | − | + | + | | | | | | | | | | | | | |
| 1-17P | + | + | + | + | | | | | | | | | | | | |
| 1-18 | + | + | | + | | | | | | | | | | | | |
| 1-24P | + | + | + | + | | | | | | | | | | | | |
| 1-27P | + | − | + | + | | | | | | | | | | | | |
| 1-40P | + | + | | | | | | | | | | | | | | |
| 1-45 | + | + | | | | | | | | | | | | | | |
| 1-46 | + | + | | | | | | | | | | | | | | |
| V$_H$ III | | | | | | | | | | | | | | | | |
| 3-6P | | | | | − | + | − | + | − | + | + | + | | | | |
| 3-7 | | | | | + | + | | + | + | | | | | | | |
| 3-9 | | | | | + | + | | + | | | | | | | | |
| 3-11 | | | | | + | + | | + | | | + | + | | | | |
| 3-13 | | | | | + | − | + | + | + | + | | | | | | |
| 3-15 | | | | | + | + | | + | + | | | | | | | |
| 3-16P | | | | | + | + | | + | | | + | | | | | |
| 3-19P | | | | | + | + | | | | | + | | | | | |
| 3-20 | | | | | + | + | | + | + | + | | | | | | |
| 3-21 | | | | | + | + | + | + | | | + | + | | | | |
| 3-22P | | | | | + | + | | + | | | | | | | | |
| 3-23 | | | | | + | + | | + | + | + | | | | | | |
| 3-29P | | | | | − | − | − | − | − | − | + | − | | | | |
| 3-30 | | | | | + | + | | + | + | + | | | | | | |
| 3-32P | | | | | − | − | − | − | − | − | + | − | | | | |
| 3-33 | | | | | + | + | | | + | + | | + | | | | |
| 3-35 | | | | | + | + | | | | | | | | | | |
| 3-36P | | | | | − | + | + | | | | | | | | | |
| 3-37P | | | | | + | − | | | | | + | | | | | |
| 3-38P | | | | | + | + | | | | | | | | | | |
| 3-41P | | | | | + | + | | | | | | | | | | |
| 3-42P | | | | | + | − | | + | | | + | | | | | |
| 3-43 | | | | | + | + | | | | | | | | | | |
| 3-47P | | | | | + | + | | | | | | | | | | |
| 3-48 | | | | | + | + | | | | | | | | | | |
| 3-49 | | | | | + | + | | | | | | | | | | |
| 3-50P | | | | | − | + | | | | | | + | | | | |
| 3-52P | | | | | + | + | | | | | | | | | | |
| 3-53 | | | | | + | + | | | | | | | | | | |
| 3-54P | | | | | + | + | | + | | | | | | | | |
| 3-64 | | | | | + | + | | | | | | | | | | |
| V$_H$ IV | | | | | | | | | | | | | | | | |
| 4-4 | | | | | | | | | | | | | + | + | + | + |
| 4-31 | | | | | | | | | | | | | + | + | − | + |
| 4-34 | | | | | | | | | | | | | + | + | + | + |
| 4-39 | | | | | | | | | | | | | + | + | | |
| 4-55P | | | | | | | | | | | | | + | + | | |

TABLE 3

| V$_H$ | kb from J$_H$ | Fragment size(kb) | |
|---|---|---|---|
| | | EcoRI | Hind III |
| 6-1 | 75 | 0.9 | 25 |
| 1-2 | 125 | 7.2 | 12.5 |
| 1-3 | 150 | 3.4 | 1.7 |
| 4-4 | 160 | 5.1 | 8.0 |
| 2-5 | 175 | 5.4 | 16.0 |
| 3-6P | 185 | 11.8 | 16.0 |
| 3-7 | 190 | 2.2 | 5.0 |
| 1-8 | 215 | 3.8 | 2.0 |
| 3-9 | 230 | 2.6 | 5.4 |
| 2-10P | 235 | 13.5 | 18.5 |
| 3-11 | 245 | 1.6 | 18.5 |
| 1-12P | 250 | 4.5 | 2.8 |
| 3-13 | 260 | 1.7 | 5.8 |
| 1-14P | 275 | 2.9 | 13.0 |
| 3-15 | 280 | 4.8 | 13.0 |
| 3-16P | 290 | 5.4 | 1.8 |

TABLE 3-continued

| $V_H$ | kb from $J_H$ | Fragment size(kb) EcoRI | Hind III |
|---|---|---|---|
| 1-17P | 295 | 5.4 + 1.6 | 10.2 |
| 1-18 | 315 | 3.4 | 8.8 |
| 3-19P | 330 | 4.3 | 14.7 |
| 3-20 | 345 | 11.8 | 12.8 |
| 3-21 | 360 | 2.2 | 6.8 |
| 3-22P | 385 | 5.7 | 7.0 |
| 3-23 | 395 | 2.0 | 5.7 |
| 1-24P | 410 | 3.0 | 5.2 |
| 3-25P | 420 | 10.0 | 7.3 |
| 2-26 | 430 | 8.1 | 6.6 |
| 1-27P | 450 | 8.3 | 11.3 |
| 4-28 | 455 | 8.3 | 5.4 |
| 3-29P | 460 | 3.5 | 5.8 |
| 3-30 | 470 | 9.8 | 6.8 |
| 4-31 | 475 | 10.3 | 13.0 |
| 3-32P | 485 | 13.3 | 5.6 |
| 3-33 | 490 | 13.3 | 6.8 |
| 4-34 | 505 | 11.5 | 16.2 |
| 3-35 | 520 | 5.3 | 3.2 |
| 3-36P | 525 | 5.3 | 5.7 |
| 3-37P | 540 | 7.5 | 13.2 |
| 3-38P | 545 | 8.0 | 15.4 |
| 4-39 | 555 | 7.0 | 15.4 |
| 1-40P | 560 | 1.4 | 3.2 |
| 3-41P | 580 | 4.4 | 11.9 |
| 3-42P | 590 | 3.0 | 3.8 |
| 3-43 | 600 | 6.5 | 8.1 |
| 3-44P | 610 | 8.8 | 17.0 |
| 1-45 | 635 | 10.7 | 2.7 |
| 1-46 | 640 | 2.0 | 4.6 |
| 3-47P | 650 | 2.7 | 10.5 |
| 3-48 | 670 | 2.7 | 3.9 |
| 3-49 | 690 | 1.6 | 16.5 |
| 3-50P | 695 | 10.0 | 16.5 |
| 5-51 | 710 | 8.0 | 11.0 |
| 3-52P | 715 | 4.0 | 11.0 |
| 3-53 | 725 | 8.3 | 6.3 |
| 3-54P | 730 | 6.4 | 15.4 |
| 4-55P | 735 | 3.9 | 15.4 |
| 1-56P | 740 | 3.4 | 15.4 |
| 3-57P | 745 | 9.7 | 6.6 |
| 1-58P | 750 | 8.3 | 17.5 |
| 4-59 | 755 | 8.3 | 17.5 |
| 3-60P | 760 | 0.8 + 3.0 | 17.5 |
| 4-61 | 770 | 8.1 | 9.0 |
| 3-62P | 775 | 4.6 | 9.0 |
| 3-63P | 780 | 8.9 | 6.2 |
| 3-64 | 790 | 4.4 | >7.4 |

---

We claim:

1. An isolated polynucleotide comprising the following nucleic acid sequences of (a) through (f) in 5' to 3' order:
   (a) a nucleic acid sequence of a portion of a human genome isolable from:
      (i) a yeast artificial chromosome clone Y6 which is isolable from a transformant identified by an international deposit number FERM BP-4271; or
      (ii) a yeast artificial chromosome clone Y24 which is isolable from a transformant identified by an international deposit number FERM BP-4274;
   (b) a nucleic acid sequence of a portion of a human genome isolable from a yeast artificial chromosome clone Y21 which is isolable from a transformant identified by an international deposit number FERM BP-4273, wherein said nucleic acid sequence lacks the 5' terminal sequence of said portion of a human genome so isolable from the clone Y21 that duplicates the 3' terminal sequence of the nucleic acid sequence of (a);
   (c) a nucleic acid sequence of a portion of a human genome isolable from a cosmid vector clone M118 which is isolable from a transformant identified by an international deposit number FERM BP-4278, wherein said nucleic acid sequence lacks the 5' terminal sequence of said portion of a human genome so isolable from the clone M118 that duplicates the 3' terminal sequence of the nucleic acid sequence of (b);
   (d) a nucleic acid sequence of a portion of a human genome isolable from a cosmid vector clone M84 which is isolable from a transformant identified by an international deposit number FERM BP-4277, wherein said nucleic acid sequence lacks the 5' terminal sequence of said portion of a human genome so isolable from the clone M84 that duplicates the 3' terminal sequence of the nucleic acid sequence of (c);
   (e) a nucleic acid sequence of a portion of a human genome isolable from a cosmid vector clone M131 which is isolable from a transformant identified by an international deposit number FERM BP-4279, wherein said nucleic acid sequence lacks the 5' terminal sequence of said portion of a human genome so isolable from the clone M131 that duplicates the 3' terminal sequence of the nucleic acid sequence of (d); and
   (f) a nucleic acid sequence of a portion of a human genome isolable from a cosmid vector clone 3-31 which is isolable from a transformant identified by an international deposit number FERM BP-4276, wherein said nucleic acid sequence lacks the 5' terminal sequence of said portion of a human genome so isolable from the clone 3-31 that duplicates the 3' terminal sequence of the nucleic acid sequence of (e),
   wherein each of said portions of a human genome which is so isolable from the clone Y6, Y24, Y21, M118, M84, M131 and 3-31 respectively is in a relative position in a human genome as shown in FIG. 1.

2. The polynucleotide of claim 1 wherein the polynucleotide has the restriction pattern and organization shown in FIG. 1.

3. The polynucleotide of claim 1 wherein the nucleic acid sequence of a portion of a human genome isolable from the clone Y6 comprises the nucleic acid sequences of SEQ ID NOS: 32 through 64;

the nucleic acid sequence of a portion of a human genome isolable from the clone Y24 comprises the nucleic acid sequences of SEQ ID NOS: 32 through 64;

the nucleic acid sequence of a portion of a human genome isolable from the clone Y21 comprises the nucleic acid sequences of SEQ ID NOS: 15 through 34;

the nucleic acid sequence of a portion of a human genome isolable from the clone M118 comprises the nucleic acid sequences of SEQ ID NOS: 14 and 15;

the nucleic acid sequence of a portion of a human genome isolable from the clone M84 comprises the nucleic acid sequences of SEQ ID NOS: 9 through 13;

the nucleic acid sequence of a portion of a human genome isolable from the clone M131 comprises the nucleic acid sequences of SEQ ID NOS: 8 and 9; and the nucleic acid sequence of a portion of a human genome isolable from the clone 3-31 comprises the nucleic acid sequences of SEQ ID NOS: 6 through 8.

4. An isolated polynucleotide comprising the following nucleic acid sequences of (a) and (b) in 5' to 3' order:

(a) a nucleic acid sequence of a portion of a human genome isolable from a yeast artificial chromosome clone Y103 which is isolable from a transformant identified by an international deposit number FERM BP-4275; and (b) a nucleic acid sequence of a portion of a human genome isolable from a yeast artificial chromosome clone Y20 which is isolable from a transformant identified by an international deposit number FERMBP-4272, wherein said nucleic acid sequence lacks the 5' terminal sequence of said portion of a human genome so isolable from the clone Y20 that duplicates the 3' terminal sequence of the nucleic acid sequence of (a), wherein each of said portions of a human genome which is so isolable from the clone Y103 and Y20 respectively is in a relative position in a human genome as shown in FIG. 1.

5. The polynucleotide of claim 4 wherein the polynucleotide has the restriction pattern and organization shown in FIG. 1.

6. The polynucleotide of claim 4 wherein the nucleic acid sequence of a portion of a human genome isolable from the clone Y103 comprises the nucleic acid sequences of SEQ ID NOS: 1 through 5, and the nucleic acid sequence of a portion of a human genome isolable from the clone Y20 comprises the nucleic acid sequences of SEQ ID NOS: 1 through 4.

7. An isolated polynucleotide of a portion of a human genome comprising the following nucleic acid sequences of (1) through (28) in 5' to 3' order: (1) SEQ ID NO: 64; SEQ ID NO:61; (3) SEQ ID NO:59; (4) SEQ ID NO:53; (5) SEQ ID NO:51; (6) SEQ ID NO:49; (7) SEQ ID NO:48; (8) SEQ ID NO:46; (9) SEQ ID NO:45; (10) SEQ ID NO:43; (11) SEQ ID NO:39; (12) SEQ ID NO:35; (13) SEQ ID NO:34; (14) SEQ ID NO:33; (15) SEQ ID NO:31; (16) SEQ ID NO:30; (17) SEQ ID NO:28; (18) SEQ ID NO:26; (19) SEQ ID NO:23; (20) SEQ ID NO:21; (21) SEQ ID NO:20; (22) SEQ ID NO: 18; (23) SEQ ID NO:15; (24) SEQ ID NO:13; (25) SEQ ID NO: 11; (26) SEQ ID NO:9; and (27) SEQ ID NO:8; and (28) SEQ ID NO:7;

wherein an intervening nucleic acid sequence appears between each of said adjacent nucleic acid sequences of (1) through (28), said intervening nucleic acid sequence being that found in:

a) a yeast artificial chromosome clone which is isolable from a transformant identified by an international deposit number selected from the group consisting of FERM BP-4271, FERM BP-4273, and FERM BP-4274; or b) a cosmid vector clone which is isolable from a transformant identified by an international deposit number selected from the group consisting of FERM BP-4276, FERM BP-4277, FERM BP-4278, and FERM BP-4279.

8. An isolated polynucleotide of a portion of a human genome comprising the following nucleic acid sequences of (1) through to (5) in 5' to 3' order:

(1) SEQ ID NO:5 (2) SEQ ID NO:4; (3) SEQ ID NO:3; (4) SEQ ID NO:2; (5) SEQ ID NO: 1;

wherein an intervening nucleic acid sequence appears between each of said adjacent nucleic acid sequences of (1) through (5), said intervening nucleic acid sequence being that found in a yeast artificial chromosome clone which is isolable from a transformant identified by an international deposit number selected from the group consisting of FERM BP-4272 and FERM BP-4275.

\* \* \* \* \*

UNITED STATES PATENT AND TRADEMARK OFFICE
CERTIFICATE OF CORRECTION

PATENT NO. : 6,096,878
DATED : AUGUST 1, 2000
INVENTOR(S) : HONJO ET AL.

It is certified that error appears in the above-identified patent and that said Letters Patent is hereby corrected as shown below:

One of the Assignees is missing from the Cover Page.

Please add --Tasuku Honjo--.

Signed and Sealed this

Seventeenth Day of April, 2001

*Attest:*

NICHOLAS P. GODICI

*Attesting Officer*      *Acting Director of the United States Patent and Trademark Office*

Disclaimer

6,096,878 — Tasuku Honjo, Kyoto (JP); and Fumihiko Matsuda, Kyoto (JP). HUMAN IMMUNOGLOBULIN VH GENE SEGMENTS AND DNA FRAGMENTS CONTAINING THE SAME. Patent dated August 1, 2000. Disclaimer filed January 11, 2010, by the assignee, Japan Tobacco Inc and Tasuku Honjo.

Hereby enters this disclaimer to claims 1-8 of said patent.

(*Official Gazette, July 5, 2011*)

SEQUENCE LISTING (1) GENERAL INFORMATION:

(iii) NUMBER OF SEQUENCES: 145

(2) INFORMATION FOR SEQ ID NO:1:

(i) SEQUENCE CHARACTERISTICS:
      (A) LENGTH: 1429 base pairs
      (B) TYPE: nucleic acid
      (C) STRANDEDNESS: double
      (D) TOPOLOGY: linear (ii) MOLECULE TYPE: Genomic DNA (vi) ORIGINAL SOURCE:
      (A) ORGANISM: Homo sapiens
      (G) CELL TYPE: human lymphoblast
      (H) CELL LINE: CGM1

(xi) SEQUENCE DESCRIPTION: SEQ ID NO:1:

```
CTGATCTATG AATAAGGGTA TATAGACCAG TTTGGCCTGA TGTAGGGAAC GCCAAAGTGC        60

TGGAATTTCA GAGTCATCAC ACCCAGGGGC CCTGCCTCTG AGCTCCTCTT TGCATCCAAT       120
```

-continued

```
CTGCTGAAGA ACATGGCTCT AGGGAAACCC AGTTGTAGAC CTGAGGGCCC CGGCTCTTCA        180

ATGAGCCATC TCCGTCCCGG GGCCTTATAT CAGCAAGTGA CGCACACAGG CAAATGCCAG        240

GGTGTGGTTT CCTGTTTAAA TGTAGCCTCC CCCGCTGCAG AACTGCAGAG CCTGCTGAAT        300

TCTGGCTGAC CAGGGCAGTC ACCAGAGCTC CAGACAATGT CTGTCTCCTT CCTCATCTTC        360

CTGCCCGTGC TGGGCCTCCC ATGGGGTCAG TGTCAGGGAG ATGCCGTATT CACAGCAGCA        420

TTCACAGACT GAGGGGTGTT TCACTTTGCT GTTTCCTTTT GTCTCCAGGT GTCCTGTCAC        480

AGGTACAGCT GCAGCAGTCA GGTCCAGGAC TGGTGAAGCC CTCGCAGACC CTCTCACTCA        540

CCTGTGCCAT CTCCGGGGAC AGTGTCTCTA GCAACAGTGC TGCTTGGAAC TGGATCAGGC        600

AGTCCCCATC GAGAGGCCTT GAGTGGCTGG GAAGGACATA CTACAGGTCC AAGTGGTATA        660

ATGATTATGC AGTATCTGTG AAAAGTCGAA TAACCATCAA CCCAGACACA TCCAAGAACC        720

AGTTCTCCCT GCAGCTGAAC TCTGTGACTC CCGAGGACAC GGCTGTGTAT TACTGTGCAA        780

GAGACACAGT GAGGGGAAGT CAGTGTGAGC CCAGACACAA ACCTCCCTGC AGGGATGCTC        840

AGGACCCCAG AAGGCACCCA GCACTACCAG CGCAGGGCCC AGACCAGGAG CAGGTGTGGA        900

GTTAAGCCAA AATGGAACTT CTTGCTGTGT CTTAAACTGT TGTTGTTTTT TTTTTTTTTT        960

TGGCTCAGCA ACAGAGATCA TAGAAAACCC TTTTTCATAT TTTTCAAATC TGTTCTTAGT       1020

CTAATGGAGA TTCTCTAATA TGTGACATTG TTTTTCTCTT GCTTGTTTTT GGAATTCTTT       1080

GTCTTTGACT TTTGACAACT TGACTTTTGA CAGTGTGCCT CAAAGAAGTT CTATTTTGGG       1140

TTCTGTGAAC CTCCTGGATC TGGGAAGTTT TCAGCTATGA TTTCATTAAA CGTGTTTTCT       1200

ACACCATTTC CCTACTTCTT TCCAATACCC ATAATGCAAA TATTTGTTCA CTTAATTGTG       1260

TCCCATAAAT GCCTGGGGAT TTTCTTCATT CCTTTTTACT CTTTTTTTCT TTTTATTCAT       1320

CTGCCTGAAT TATTTCAAAA GATCTGTCTT CAACTTCAGA AACTCTTTGG CTTGGCCTAG       1380

TCTAATCTTG AAGGTCTCAA TTGTACTTTT AATTTCATTC ATTGAATTC                   1429
```

(2) INFORMATION FOR SEQ ID NO:2:

(i) SEQUENCE CHARACTERISTICS:
        (A) LENGTH: 512 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:2:

```
TGAGAGCTCC GTTCCTCACC ATGGACTGGA CCTGGAGGAT CCTCTTCTTG GTGGCAGCAG         60

CCACAGGTAA GAGGCTCCCT AGTCCCAGTG ATGAGAAAGA GATTGAGTCC AGTCCAGGGA        120

GATCTCATCC ACTTCTGTGT TCTCTCCACA GGAGCCCACT CCCAGGTGCA GCTGGTGCAG        180

TCTGGGGCTG AGGTGAAGAA GCCTGGGGCC TCAGTGAAGG TCTCCTGCAA GGCTTCTGGA        240

TACACCTTCA CCGGCTACTA TATGCACTGG GTGCGACAGG CCCCTGGACA AGGGCTTGAG        300

TGGATGGGAT GGATCAACCC TAACAGTGGT GGCACAAACT ATGCACAGAA GTTTCAGGGC        360

AGGGTCACCA TGACCAGGGA CACGTCCATC AGCACAGCCT ACATGGAGCT GAGCAGGCTG        420

AGATCTGACG ACACGGCCGT GTATTACTGT GCGAGAGACA CAGTGTGAAA ACCCACATCC        480

TGAGGGTGTC AGAAACCCAA GGGAGGAGGC AG                                     512
```

(2) INFORMATION FOR SEQ ID NO:3:

(i) SEQUENCE CHARACTERISTICS:
        (A) LENGTH: 496 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:3:

```
CACAACTCCT CACCATGGAC TGGACCTGGA GGATCCTCTT TTTGGTGGCA GCAGCCACAG    60

GTAAGGGGCT GCCAAATCCC AGTGAGGAGG AAGGGACTGA AGCCAGTCAA GGGGGCTTCC   120

ATCCACTCCT GTGTCTTCTC TACAGGTGTC CACTCCCAGG TTCAGCTGGT GCAGTCTGGG   180

GCTGAGGTGA AGAAGCCTGG GGCCTCAGTG AAGGTTTCCT GCAAGGCTTC TGGATACACC   240

TTCACTAGCT ATGCTATGCA TTGGGTGCGC CAGGCCCCCG ACAAAGGCT TGAGTGGATG    300

GGATGGAGCA ACGCTGGCAA TGGTAACACA AAATATTCAC AGGAGTTCCA GGGCAGAGTC   360

ACCATTACCA GGGACACATC CGCGAGCACA GCCTACATGG AGCTGAGCAG CCTGAGATCT   420

GAGGACATGG CTGTGTATTA CTGTGCGAGA GACACAGTGT GAAAACCCAC ATCCTGAGAG   480

TGTCAGAAAC CCCAGG                                                   496
```

(2) INFORMATION FOR SEQ ID NO:4:

(i) SEQUENCE CHARACTERISTICS:
        (A) LENGTH: 650 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:4:

```
CACAGGAAAC CACCACACAT TTCCTTAAAT TCAGGGTCCA GCTCACATGG GAAATACTTT    60

CTGAGACTCA TGGACCTCCT GCACAAGAAC ATGAAACACC TGTGGTTCTT CCTCCTGCTG   120

GTGGCAGCTC CCAGATGTGA GTGTCTCAAG GCTGCAGACA TGGGATATGG GAGGTGCCTC   180

TGATCCCAGG GCTCACTGTG GGTCTCTCTG TTCACAGGGG TCCTGTCCCA GGTGCAGCTG   240

CAGGAGTCGG GCCCAGGACT GGTGAAGCCT TCGGAGACCC TGTCCCTCAC CTGCACTGTC   300

TCTGGTGGCT CCATCAGTAG TTACTACTGG AGCTGGATCC GGCAGCCCGC CGGGAAGGGA   360

CTGGAGTGGA TTGGGCGTAT CTATACCAGT GGGAGCACCA ACTACAACCC CTCCCTCAAG   420

AGTCGAGTCA CCATGTCAGT AGACACGTCC AAGAACCAGT TCTCCCTGAA GCTGAGCTCT   480

GTGACCGCCG CGGACACGGC CGTGTATTAC TGTGCGAGAG ACACAGTGAG GGGAGGTGAG   540

TGTGAGCCCA GACACAAACC TCCCTGCAGG GAGGCGGAGG GGACCGGCGC AGGTGCTGCT   600

CAAGACCAGC AGGGGCGCG CGGGGCCCAC AGAGCAAGAG GCCGGGTCAG                650
```

(2) INFORMATION FOR SEQ ID NO:5:

(i) SEQUENCE CHARACTERISTICS:
        (A) LENGTH: 613 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:5:

```
CCAGCTCCAC CCTCCTCTGG GTTGAAAAAG CCGAGCACAG GTACCAGCTC AGTGACTCCT    60

GTGCACCACC ATGGACACAC TTTGCTCCAC GCTCCTGCTG CTGACCATCC CTTCATGTGA   120

GTGCTGTGGT CAGGGACTCC TTCACGGGTG AAACATCAGT TTTCTTGTTT GTGGGCTTCA   180

TCTTCTTATG CTTTCTCCAC AGGGGTCTTG TCCCAGATCA CCTTGAAGGA GTCTGGTCCT   240

ACGCTGGTGA AACCCACACA GACCCTCACG CTGACCTGCA CCTTCTCTGG GTTCTCACTC   300

AGCACTAGTG GAGTGGGTGT GGGCTGGATC CGTCAGCCCC CAGGAAAGGC CCTGGAGTGG   360

CTTGCACTCA TTTATTGGAA TGATGATAAG CGCTACAGCC CATCTCTGAA GAGCAGGCTC   420

ACCATCACCA AGGACACCTC CAAAAACCAG GTGGTCCTTA CAATGACCAA CATGGACCCT   480

GTGGACACAG CCACATATTA CTGTGCACAC AGACCACAAA GACACAGCCC AGGGCACCTC   540

CTGTACAAAA ACCCAGGCTG CTTCTCATTG GTGCTCCCTC CCCACCTCTG CAGAACAGGA   600

AAGTCTGTCT GCT                                                      613
```

(2) INFORMATION FOR SEQ ID NO:6:

(i) SEQUENCE CHARACTERISTICS:
        (A) LENGTH: 594 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:6:

```
ACAGGATTCA CCATGGAGTT GGGGCTGAGG TGGGTTTTCC TTGCTGCTAT TTTAAAAGGT    60

GATTTATGGT TAACTAGAGC TATTGAGTGT GAATGGACAT AAGTGAGCGA AACAGTGGAT   120

ATGTGTGGCA GTTTCTTACC AGGATGTCTC TGTGTTTGCA GGTGTCCAGT GTGAGATGCA   180

GCTGGTAGAG TCTGGAGCAA ACTTGACAAA GCCTGGGTGT CCCTGAGACT CTCCTGTGCA   240

GCCTCTGGAT TCACCTTCAG TAGCCATAGC ACGCACTGGG TCCCCCAGGC TCCAGGGAAG   300

GGTCTGCAGT GGGTCCCAGT TATTAGTGGT AGTGGTAGTA CCATGTACTA CGCAGACTCT   360

GTGAAGGGCC GATTCACCAT TTCCAGAGAC AATACCAAAA ACTCACTGTA TCTGCAAATG   420

AACAGACTGA GGGCAGAGGA TGCAGCTGCA TATGACTCTG TGAGAGATAC GGTAAGGAGA   480

AGTCAGTGTG AGCCCAGACA CAAACCTCCC TTCAGGGTAC CTGGGACAAC CAGGGAAAGC   540

CTGGGACACT GTGCACTGTG CTGACCCCAG GGGCAAGTGC AGGTGCTACA AGGG         594
```

(2) INFORMATION FOR SEQ ID NO:7:

(i) SEQUENCE CHARACTERISTICS:
    (A) LENGTH: 877 base pairs
    (B) TYPE: nucleic acid
    (C) STRANDEDNESS: double
    (D) TOPOLOGY: linear (ii) MOLECULE TYPE: Genomic DNA (vi) ORIGINAL SOURCE:
    (A) ORGANISM: Homo sapiens
    (G) CELL TYPE: human lymphoblast
    (H) CELL LINE: CGM1

(xi) SEQUENCE DESCRIPTION: SEQ ID NO:7:

```
ACAGCCTATT CCTCCAGCAT CCCACTAGAG CTTCTTATAT AGTAGGAGAC ATGCAAATAG      60

GGCCCTCCCT CTACTGATGA AAACCAACCC AACCCTGACC CTGCAGGTCT CAGAGAGGAG     120

CCTTAGCCCT GGACTCCAAG GCCTTTCCAC TTGGTGATCA GCACTGAGCA CAGAGGACTC     180

ACCATGGAAT TGGGGCTGAG CTGGGTTTTC CTTGTTGCTA TTTTAGAAGG TGATTCATGG     240

AAAACTAGGA AGATTGAGTG TGTGTGGATA TGAGTGTGAG AAACAGTGGA TTTGTGTGGC     300

AGTTTCTGAC CTTGGTGTCT CTTTGTTTGC AGGTGTCCAG TGTGAGGTGC AGCTGGTGGA     360

GTCTGGGGGA GGCTTGGTCC AGCCTGGGGG GTCCCTGAGA CTCTCCTGTG CAGCCTCTGG     420

ATTCACCTTT AGTAGCTATT GGATGAGCTG GGTCCGCCAG GCTCCAGGGA AGGGGCTGGA     480

GTGGGTGGCC AACATAAAGC AAGATGGAAG TGAGAAATAC TATGTGGACT CTGTGAAGGG     540

CCGATTCACC ATCTCCAGAG ACAACGCCAA GAACTCACTG TATCTGCAAA TGAACAGCCT     600

GAGAGCCGAG GACACGGCTG TGTATTACTG TGCGAGAGAC ACAGTGAGGG GAAGTCAGTG     660

TGAGCCCAGA CACAAACCTC CCTGCAGGGG TCCCTTGGGA CCACCAGGGG GCGACAGGGC     720

ATTGAGCACT GGGCTGTCTC CAGGGCAGGT GCAGGTGCTG CTGAGGGCTG GCTTCCTGTC     780

GCGGTCTGGG GCTGCCTCGT CGTCAAATTT CCCCAGGAAC TTCTCCAGAT TTACAATTCT     840

GTACTGACAT TTCATGTCTC TAAATGCAAT ACTTTTT                              877
```

(2) INFORMATION FOR SEQ ID NO:8:

(i) SEQUENCE CHARACTERISTICS:
        (A) LENGTH: 564 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:8:

```
CACTCCACCA ACCACATCTG TCCTCTAGAG AAAACCCTGT GAGCACACCT CCTCACCATG      60

GACTGGACCT GGAGGATCCT CTTCTTGGTG GCAGCAGCTA CAAGTAAGGG GCTTCCTAGT     120

CTCAAAGCTG AGGAACGGAT CCTGGTTCAG TCAAAGAGGA TTTTATTCTC TCCTGTGTTC     180

TCTCCACAGG TGCCCACTCC CAGGTGCAGC TGGTGCAGTC TGGGGCTGAG GTGAAGAAGC     240

CTGGGGCCTC AGTGAAGGTC TCCTGCAAGG CTTCTGGATA CACCTTCACC AGTTATGATA     300

TCAACTGGGT GCGACAGGCC ACTGGACAAG GGCTTGAGTG GATGGGATGG ATGAACCCTA     360

ACAGTGGTAA CACAGGCTAT GCACAGAAGT TCCAGGGCAG AGTCACCATG ACCAGGAACA     420

CCTCCATAAG CACAGCCTAC ATGGAGCTGA GCAGCCTGAG ATCTGAGGAC ACGGCCGTGT     480
```

```
ATTACTGTGC GAGAGGCACA GTGTGAAAAA CCACATCCTC AGAGAGTCAG AAACCCCTAG      540

GGGAGAAGGC AGCTTCTGCT GGGC                                            564

(2) INFORMATION FOR SEQ ID NO:9:

(i) SEQUENCE CHARACTERISTICS:
        (A) LENGTH: 640 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:9:

CAAATAGGGC CTCCCTCTG CTGATGAAAA CCAGCCCAGC CCTGACCCTG CAGCTCTGGG       60

AGAGGAGCCC CAGCCCTGAG ATTCCCAGGT GTTTCCATTC AGTGATCAGC ACTGAACACA     120

GAGGACTCAC CATGGAGTTG GGACTGAGCT GGATTTTCCT TTTGGCTATT TTAAAAGGTG     180

ATTCATGGAG AAATAGAGAG ATTGAGTGTG AGTGGACATG AGTGGATTTG TGTGGCAGTT     240

TCTGACCTTG GTGTCTCTGT GTTTGCAGGT GTCCAGTGTG AAGTGCAGCT GGTGGAGTCT     300

GGGGGAGGCT TGGTACAGCC TGGCAGGTCC CTGAGACTCT CCTGTGCAGC CTCTGGATTC     360

ACCTTTGATG ATTATGCCAT GCACTGGGTC CGGCAAGCTC CAGGGAAGGG CCTGGAGTGG     420

GTCTCAGGTA TTAGTTGGAA TAGTGGTAGC ATAGGCTATG CGGACTCTGT GAAGGGCCGA     480

TTCACCATCT CCAGAGACAA CGCCAAGAAC TCCCTGTATC TGCAAATGAA CAGTCTGAGA     540

GCTGAGGACA CGGCCTTGTA TTACTGTGCA AAAGATACAC AGTGAGGGGA AGTCAGCGAG     600

AGCCCAGACA AAAACCTCCT GCAGGAAGAC AGGAGGGGCC                           640

(2) INFORMATION FOR SEQ ID NO:10:

(i) SEQUENCE CHARACTERISTICS:
        (A) LENGTH: 630 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:10:

AGCTCCACCC TTCTCTGTGT TGAAAAGCCG AGCATGGGGA CCTAGTTCAG TGACTCCTGC       60

GCCCCACCAC ATGGAGCTTT ACTCCACGCT TCTCCTGCTG ACTGTCCCTT CCTGTGAGTT     120

CAGTGGTCAG GGAATCCTTC AGGGGTGAAA CACCTGTTCT TTCTTTGTG GGCTTCATCT      180

TCTTATGCTT TCTCCACAGG GGTCTTATCC CAGGTCACCT TGAAGGAGTC TGGTCCTGCA     240

CTGGTGAAAC CCACACAGAC CCTCATGCTG ACCTGCACCT TCTCTGGGTT CTCACTCAGC     300

ACTTCTGGAA TGGGTGTGGG TTAGATCTGT CAGCCCTCAG CAAAGGCCCT GGAGTGGCTT     360

GCACACATTT ATTAGAATGA TAATAAATAC TACAGCCCAT CTCTGAAGAG TAGGCTCATT     420

ATCTCCAAGG ACACCTCCAA GAATGAAGTG GTTCTAACAG TGATCAACAT GGACATTGTG     480

GACACAGCCA CACATTACTG TGCAAGGAGA CCACAGAGAC AGAGCCCAGG GTGCCTCTTG     540
```

| | |
|---|---|
| TACAAGACCC AGGCTGCTTC TCAGTGGCGC TCCCTCCCCA CCTCTGCAGA ACAGGAAAGT | 600 |
| GTGGCTGAGA TGCCATTTCC TGTCAGGGTC | 630 |

(2) INFORMATION FOR SEQ ID NO:11:

(i) SEQUENCE CHARACTERISTICS:
        (A) LENGTH: 715 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:11:

| | |
|---|---|
| CACCCCAGGC TTTACACTTT ATGCTTCCGG CTCGTATGTT GTGTGGAATT GTGAGCGGAT | 60 |
| AACAATTTCA CACAGGAAAC AGCTATGACC ATGATTACGC CAAGCTTGCA TGCCTGCAGG | 120 |
| TCGACTCTAG AGGATCCCCG GGTACCGAGC TCGAATTCCC AGGAGTTTCC ATTCGGTGAT | 180 |
| CAGCACTGAA CACAGAGGAC TCACCATGGA GTTTGGGCTG AGCTGGGTTT TCCTTGTTGC | 240 |
| TATAATAAAA GGTGATTTAT GGAGAACTAG AGACATTGAG TGGACGTGAG TGAGATAAGC | 300 |
| AGTGAATATA TGTGGCAGTT TCTGACTAGG TTGTCTCTGT GTTTGCAGGT GTCCAGTGTC | 360 |
| AGGTGCAGCT GGTGGAGTCT GGGGGAGGCT TGGTCAAGCC TGGAGGGTCC CTGAGACTCT | 420 |
| CCTGTGCAGC CTCTGGATTC ACCTTCAGTG ACTACTACAT GAGCTGGATC CGCCAGGCTC | 480 |
| CAGGGAAGGG GCTGGAGTGG GTTTCATACA TTAGTAGTAG TGGTAGTACC ATATACTACG | 540 |
| CAGACTCTGT GAAGGGCCGA TTCACCATCT CCAGGGACAA CGCCAAGAAC TCACTGTATC | 600 |
| TGCAAATGAA CAGCCTGAGA GCCGAGGACA CGGCCGTGTA TTACTGTGCG AGAGACACAG | 660 |
| TGAGGGGAAG TCAGTGTGAG CCCAGACACA AACCTCCCTG CAGGGGGTCC CTTGG | 715 |

(2) INFORMATION FOR SEQ ID NO:12:

(i) SEQUENCE CHARACTERISTICS:
        (A) LENGTH: 660 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:12:

| | |
|---|---|
| GGATTGGGCT TTGAGCTAAG GANAGGCTTT GTCNNATGAA TATNCGAATA TACTGATATC | 60 |
| CACTGAGNTG AATATGTTCT GTNCCCTGAG AGAATCACCT GAGAGAATCC CCTGAGAGCA | 120 |
| CATCTCCTCA TGGNCTGGAC CTACAAGATC CTCTTCTTGG TGGCAGCAGC CACAGGTAAG | 180 |
| CAGTTCCCAG GTCAAGTAA TGAGGAGGGG ATTGAGTCCA GTCAAGGGGG CTTTCATCCA | 240 |
| CTCCTGTGTC CTCCCCACAG GTGCCCACTC CCAGGTGCAG CTGGTGCAAT CTGGGGCTGA | 300 |
| GGTGAAGAAG CCTGGGGCCT CAGTGAAGGT CTCCTGCAAG GCTTCTGGAT ACACCTTCAC | 360 |
| CTACTGCTAC TTGCACTGGG TATGACAGGC CCCTGGACAA GGGCTTGAAT GGACAGGATT | 420 |

```
TTAGTTATTT GAGAGATTTT TCATACAACA TTTATTCTGT AAGCAAATTT CAGGGATTGT      480

AGAATGAATC ATATTAACAA ATCTGACACA GAACTTCCTC TGAATCAATC TTTGTAAACA      540

TCAATTTCTG AATCAATGTT GTNAATATTT CAGAACACAA GCACAANTTC ACATTTNAAC      600

TCTACTTTNA TCTCTATTTA AAANATATCA AAAANTCTCA TCNNGTGCAT GTAACGTTTG      660

(2) INFORMATION FOR SEQ ID NO:13:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
         (A) ORGANISM: Homo sapiens
         (G) CELL TYPE: human lymphoblast
         (H) CELL LINE: CGM1

(xi) SEQUENCE DESCRIPTION: SEQ ID NO:13:

AATAAAAAAA TGATAGTTGT TAAATGTTTA TCGCAGAACA ATTCCAAATA AGGCAGCATT       60

TTCCCCAAAT ACAATCATTG TCATCCAAAA TCCCCCAGGA CGCTCTCATC TACTCTGCCC      120

CTGCCTTCAC CTCAGATGTC CCACCCCAGA GCTTGCTATA TAGTAACAGA CATGCAAATA      180

GTTGACTCCC TCTCCTGATG AAAACCAGCC CAGCCCTGAC CCTGCAGCTC TGGGAGTGGA      240

GCCCCAGCCT TGGGATTCCC AAGTGTTTGT ATTCAGTGAT CAGGACTGAA CACACAGGAC      300

TCACCATGGA GTTGGGGCTG AGCTGGGTTT TCCTTGTTGC TATATTAGAA GGTGATTCAT      360

GGAGAACTAG AGATATTGAG TGTGAATGGG CATGAATGAG AGAAACAGTG GGTATGTGTG      420

GCAATTTCTG ACTTTTGTGT CTCTGTGCCT TGCAGGTGTC CAGTGTGAGG TGCATCTGGT      480

GGAGTCTGGG GGAGGCTTGG TACAGCCTGG GGGGCCCTG AGACTCTCCT GTGCAGCCTC       540

TGGATTCACC TTCAGTAACT ACGACATGCA CTGGGTCCGC CAAGCTACAG GAAAAGGTCT      600

GGAGTGGGTC TCAGCCAATG GTACTGCTGG TGACACATAC TATCCAGGCT CCGTGAAGGG      660

GCGATTCACC ATCTCCAGAG AAAATGCCAA GAACTCCTTG TATCTTCAAA TGAACAGCCT      720

GAGAGCCGGG GACACGGCTG TGTATTACTG TGCAAGAGAC ACAGTGAGGG GAAGTCAGTA      780

TGAGCCCAGA CACAAACCTC CCTGCAGAAT GCCTGGGGG                             819

(2) INFORMATION FOR SEQ ID NO:14:

(i) SEQUENCE CHARACTERISTICS:
        (A) LENGTH: 816 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
         (A) ORGANISM: Homo sapiens
         (G) CELL TYPE: human lymphoblast
         (H) CELL LINE: CGM1

(xi) SEQUENCE DESCRIPTION: SEQ ID NO:14:

AGNGANGAAG GNAGTGATCA CTGTGATCTT TTCNCCAAGT TCACCATTTC NCTGAAGGTG       60

AGCACAGGTC CTCCTGCATG TGTTCAAACA AAAGNNNNAG AGACTACCTG GTAAGTGAGG      120

TGCTCACCTG GTTCTGGATG TTTGGTCTGT CTCCTCCCCT CTGTTGCCCC ACACAAGGTC      180

AGCCCACTCT TTCCAGGTCC GAAGAAGAGA GCACAGGTTT GTCCTGATTA TATGACTCAC      240
```

```
CCAGCTTCTG ATGACTCTCC TGTTGCCAGC GTCCATGGCC TCAGTGAAGG TCTCCTGCAA    300

AGCTCTGGAT ACACCTTCGC CAGCTACGAC ATTCACTGTG TGTGACAGGC CCCTGGATAA    360

GGGTTTGANT GGATGGTAGG GAGCTACTCT GGCAATGGTA ACACAGGCTA TGCACAGAAG    420

TTTCAGGGCA GAGTCACCAT GACCAGGGAC ACGTCCACGA GCACAGCCTA CATGGAGCTG    480

AGCAGTCAGA GATCTGAGGA CATAGATGTG TACTACTGTG CGANACACAC AGTGTGACAN    540

CCCACATCCT GAGAGAGTCA GAAATCCTGA GGGAGGTGGC AGCAGTGCTA GGCTTGAGAG    600

ATGACAGGGA TTTTATTTGC TTTNNCGGCT TTTTTTNGNN AGCGAGGTTA NTTCATTACA    660

GANNNNNGGA AAATAGAAAT GTGTATGGAC TCTAATTATG TGGGAAATTT CCATACAACT    720

TTGGTTCTCT TNGNNNNTTC AGGGGTNGGA NNCAATCAAT TAATAACCTG ATAAAGATTC    780

GAGTCGTACC CNGGATCCCT GNTTCGCCTG AGNATA                              816

(2) INFORMATION FOR SEQ ID NO:15:

(i) SEQUENCE CHARACTERISTICS:
        (A) LENGTH: 535 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:15:

CACAGAGGAC TCACCATGGA GTTTGGGCTG AGCTGGATTT TCCTTCCTGC TATTTTAAAA     60

GGTGATTTAT GGAGAACTAG AGAGATTAAG TGTGAGTGGA CGTGAGTGAG AGAAACAGTG    120

GATATGTGTG GCAGTTTCTG ATCTTAGTGT CTCTGTGTTT GCAGGTGTCC AGTGTGAGGT    180

GCAGCTGGTG GAGTCTGGGG GAGCCTTGGT AAAGCCTGGG GGGTCCCTTA GACTCTCCTG    240

TGCAGCCTCT GGATTCACTT TCAGTAACGC CTGGATGAGC TGGGTCCGCC AGGCTCCAGG    300

GAAGGGGCTG GAGTGGGTTG GCCGTATTAA AAGCAAAACT GATGGTGGGA CAACAGACTA    360

CGCTGCACCC GTGAAAGGCA GATTCACCAT CTCAAGAGAT GATTCAAAAA ACACGCTGTA    420

TCTGCAAATG AACAGCCTGA AAACCGAGGA CACAGCCGTG TATTACTGTA CCACAGACAC    480

AGTGAGGGA GGTCAGTGTG AGCCCGGACA CAAACCTCCC TGCAGGGGCG CGCGG          535

(2) INFORMATION FOR SEQ ID NO:16:

(i) SEQUENCE CHARACTERISTICS:
        (A) LENGTH: 542 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:16:

ATTGGGTCAA CAGCAATAAA CAAATTACCA TGGAATTTGG GCTGAGCTGG GTTTTTCTTG     60

CTGGTATTTT AAAAGGTGAT TCATGGAGAA CTAAGGATAT TGAGTGAGTG GACATGAGTG    120
```

| | |
|---|---|
| AGAGAAACAG TGGATATGTG TGGCAGTTTC TGACCAGGGT GTCTCTGTGT TTGCAGGTGT | 180 |
| CCAGTGTGAG GTACAACTGG TGGAGTCTGG GGGAGGCTTG GTACAGCCTG GGGGGTCCCT | 240 |
| GAGACTCTCC TGTGCAGCCT CTGGATTCAC CTTCAGTAAC AGTGACATGA ACTGGGCCCG | 300 |
| CAAGGCTCCA GGAAAGGGGC TGGAGTGGGT ATCGGGTGTT AGTTGGAATG CAGTAGGAC | 360 |
| GCACTATGTG GACTCCGTGA AGCGCCGATT CATCATCTCC AGAACAATT CCAGGAACTC | 420 |
| CCTGTATCTG CAAAAGAACA GACGGAGAGC CGAGGACATG GCTGTGTATT ACTGTGTGAG | 480 |
| AAATCCTGTG AGGGGACACA AGTGCGAGCC CAGACACAAA CCTCCTGCAG GAACACTGGG | 540 |
| CG | 542 |

(2) INFORMATION FOR SEQ ID NO:17:

(i) SEQUENCE CHARACTERISTICS:
        (A) LENGTH: 591 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:17:

| | |
|---|---|
| ACATCCCTCC TCTATAGAAG CCCCTGAGAG CACAGCTCCT CACCATGGAC TGTACCTGGG | 60 |
| GGATCCTCTT CTTGGTGGCA TCTNCCACAG GTAAGGGGCT CCCAAGTCCT AGTGATGAGG | 120 |
| AGGGGATTGA GTCCAGTCAA GGGGGCTTTT ATCATCTCCT CCCTTCTCCT CACAGATGTC | 180 |
| CATTCCCAGG TTCAGCTGTT GCAGCCTGGG GCTGAGGTGA AGAAGCCTGC GTCCTCAGTG | 240 |
| AAGGTCTCCT GGCCAGGCTT CCAGATACAC CTTCACCAAA TACTTTACAC AGTGGGTGCG | 300 |
| ACAGGGCCCT GGACAAGGGC ATAGTGGTTG GGATGCATCA ACCCTTACAA TGATAACACA | 360 |
| CACTACGCAC AGAAGTTCCG GGGCAGAGTC ACCATTACCA GTGACAGGTC CGTGAGCACA | 420 |
| GCCTACATGG AGCTGAGCAG TCTGAGATCT GAAGACATGG TCGTGTATTC CTGTGTGAGA | 480 |
| GACACAGTGC GAAAACCCAC ATCCTGAGAG TGTCAGAAAC CCCAGGAAGG AGGCACCTGT | 540 |
| GCTGACACAG AGGGAGATGA CAAAGATTAT TAGATTAACG ATTTTCTTAG A | 591 |

(2) INFORMATION FOR SEQ ID NO:18:

(i) SEQUENCE CHARACTERISTICS:
        (A) LENGTH: 539 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:18:

| | |
|---|---|
| CAAACACCCC TCCTTGGGAG AATCCCCTAG ATCACAGCTC CTCACCATGG ACTGGACCTG | 60 |
| GAGCATCCTT TTCTTGGTGG CAGCACCAAC AGGTAACGGA CTCCCCAGTC CCAGGGCTGA | 120 |
| GAGAGAAACC AGGCCAGTCA TGTGAGACTT CACCCACTCC TGTGTCCTCT CCACAGGTGC | 180 |
| CCACTCCCAG GTTCAGCTGG TGCAGTCTGG AGCTGAGGTG AAGAAGCCTG GGGCCTCAGT | 240 |

```
GAAGGTCTCC TGCAAGGCTT CTGGTTACAC CTTTACCAGC TATGGTATCA GCTGGGTGCG      300

ACAGGCCCCT GGACAAGGGC TTGAGTGGAT GGGATGGATC AGCGCTTACA ATGGTAACAC      360

AAACTATGCA CAGAAGCTCC AGGGCAGAGT CACCATGACC ACAGACACAT CCACGAGCAC      420

AGCCTACATG GAGCTGAGGA GCCTGAGATC TGACGACACG GCCGTGTATT ACTGTGCGAG      480

AGACACAGTG TGAAAACCCA CATCCTGAGG GTTTCAGAAA CCCCAGGGAG GAGGCAGCT      539
```

(2) INFORMATION FOR SEQ ID NO:19:

(i) SEQUENCE CHARACTERISTICS:
        (A) LENGTH: 727 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:19:

```
AGATTTAAGA ACCTTGCACC TGGTACCCGT TGCTCTTCTT GTAACCATTT GTCTTTTAAG       60

TTGTTTATCA CTCTGTAACT ATTTTGATTA TTTTGATTCT TGCATGTTTT TACTTCTGTA      120

AAATTATTAC ATTTGAGTCC CTCTCCCCTT CCTAAACCTA GGTATAAAAT TTACTCGAGC      180

CCCTTCCTCG TGGCCGAGAG AATTTTGAGC ATGAGCTGTC TCTTTGGCAG CCGGCTTAAT      240

AAAGGACTCT TAATTCGTCT CAAAGTGTGG CGTTTTCTTA ACTCACCTGG GTACAACAGT      300

GCAGCTGGTG GAGTCTGGGG GAGGCTTGGT AGAGCCTGGG GGGTCCCTGA GACTCTCCTG      360

TGCAGCCTCT GGATTCACCT TCAGTAACAG TGACATGAAC TGGGTCCGCC AGGCTCCAGG      420

AAAGGGGCTG GAGTGGGTAT CGGGTGTTAG TTGGAATGGC AGTAGGACGC ACTATGCAGA      480

CTCTGTGAAG GGCCGATTCA TCATCTCCAG AGACAATTCC AGGAACTTCC TGTATCAGCA      540

AATGAACAGC CTGAGGCCCG AGGACATGGC TGTGTATTAC TGTGTGAGAA ACACTGTGAG      600

AGGACGGAAG TGTGAGCCCA GACACAAACC TCCTGCAGGA ACGTTGGGGG AAATCAGCTG      660

CAGGGGCGC TCAAGACCCA CTCATCAGAG TCAACCCCAG AGCAGGTGCA CATGGAGGCT      720

GGGTTTT                                                                727
```

(2) INFORMATION FOR SEQ ID NO:20:

(i) SEQUENCE CHARACTERISTICS:
        (A) LENGTH: 514 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:20:

```
GGACTCGCCA TGGAGTTTGG GCTGAGCTGG GTTTTCCTTG TTGCTATTTT AAAAGGTGAT       60

TCATGGATCA ATAGAGATGT TGAGTGTGAG TGAACACGAG TGAGAGAAAC AGTGGATTTG      120

TGTGGCAGTT TCTGACCAGG GTGTCTCTGT GTTTGCAGGT GTCCAGTGTG AGGTGCAGCT      180
```

```
GGTGGAGTCT GGGGGAGGTG TGGTACGGCC TGGGGGGTCC CTGAGACTCT CCTGTGCAGC    240

CTCTGGATTC ACCTTTGATG ATTATGGCAT GAGCTGGGTC CGCCAAGCTC CAGGGAAGGG    300

GCTGGAGTGG GTCTCTGGTA TTAATTGGAA TGGTGGTAGC ACAGGTTATG CAGACTCTGT    360

GAAGGGCCGA TTCACCATCT CCAGAGACAA CGCCAAGAAC TCCCTGTATC TGCAAATGAA    420

CAGTCTGAGA GCCGAGGACA CGGCCTTGTA TCACTGTGCG AGAGACACAG TGAGGGGAAG    480

CCAGTGAGAG CCCAGACACA AACGTCCCTG CAGG                                514

(2) INFORMATION FOR SEQ ID NO:21:

(i) SEQUENCE CHARACTERISTICS:
        (A) LENGTH: 519 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO :21:

AGGATTCACC ATGGAACTGG GGCTCCGCTG GGTTTTCCTT GTTGCTATTT TAGAAGGTGA     60

ATCATGGAAA AGTAGAGAGA TTTAGTGTGT GTGGATATGA GTGAGAGAAA CGGTGGATGT    120

GTGTGACAGT TTCTGACCAA TGTCTCTCTG TTTGCAGGTG TCCAGTGTGA GGTGCAACTG    180

GTGGAGTCTG GGGGAGGCCT GGTCAAGCCT GGGGGGTCCC TGAGACTCTC CTGTGCAGCC    240

TCTGGATTCA CCTTCAGTAG CTATAGCATG AACTGGGTCC GCCAGGCTCC AGGGAAGGGG    300

CTGGAGTGGG TCTCATCCAT TAGTAGTAGT AGTAGTTACA TATACTACGC AGACTCAGTG    360

AAGGGCCGAT TCACCATCTC CAGAGACAAC GCCAAGAACT CACTGTATCT GCAAATGAAC    420

AGCCTGAGAG CCGAGGACAC GGCTGTGTAT TACTGTGCGA GAGACACAGT GAGGGGAAGT    480

CAGTGTGAGC CCAGACACAA ACCTCCCTGC AGGGGTCCC                           519

(2) INFORMATION FOR SEQ ID NO:22:

(i) SEQUENCE CHARACTERISTICS:
        (A) LENGTH: 606 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:22:

CTACAGCTCT GGGAGAGGAC CCCCAGCCCT GGGATTTTCA GATGTTTTCA TTTGGTGATC     60

AGGACTGAAC ACAGAGGACT CACCATGGAG TCATGGCTGA GCTGGGTTTT TCTTGCCGCT    120

ATTTTAAAAG GTAATTCATT GAGAACTATT GAAATTGAGT GTGAGCGGAT AAGAGTGAGA    180

GAAACAGTGG ATACGTGTGG CAGTTTCTGA CCAGGGTTTC TTTTTGTTTG CAGGTGTCCA    240

GTGTGAGGTG CATCTGGTGG AGTCTGGGGG AGCCTTGGTA CAGCCTGGGG GTCCCTGAG     300

ACTCTCCTGT GCAGCCTCTG GATTCACCTT CAGTTACTAC TACATGAGCG GGTCCGCCA     360

GGCTCCCGGG AAGGGGCTGG AATGGGTAGG TTTCATTAGA AACAAAGCTA ATGGTGGGAC    420
```

```
AACAGAATAG ACCACGTCTG TGAAAGGCAG ATTCACAATC TCAAGAGATG ATTCCAAAAG      480

CATCACCTAT CTGCAAATGA AGAGCCTGAA AACCGAGGAC ACGGCCGTGT ATTACTGTTC      540

CAGAGACACA GTGAGGGGAG GTCAGTGTGA GCCCGGACAC AAACCTCCCT GCAGGGGCGC      600

GCGGGG                                                                606

(2) INFORMATION FOR SEQ ID NO:23:

(i) SEQUENCE CHARACTERISTICS:
        (A) LENGTH: 514 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:23:

GAACTCACCA TGGAGTTTGG GCTGAGCTGG CTTTTTCTTG TGGCTAAAAT AAAAGGTAAT       60

TCATGGAGAA ATAGAAAAAT TGAGTGTGAA TGGATAAGAG TGAGAGAAAC AGTGGATACG      120

TGTGGCAGTT TCTGACCAGG GTTTCTTTTT GTTTGCAGGT GTCCAGTGTG AGGTGCAGCT      180

GTTGGAGTCT GGGGGAGGCT TGGTACAGCC TGGGGGGTCC CTGAGACTCT CCTGTGCAGC      240

CTCTGGATTC ACCTTTAGCA GCTATGCCAT GAGCTGGGTC CGCCAGGCTC AGGGAAGGG       300

GCTGGAGTGG GTCTCAGCTA TTAGTGGTAG TGGTGGTAGC ACATACTACG CAGACTCCGT      360

GAAGGGCCGG TTCACCATCT CCAGAGACAA TTCCAAGAAC ACGCTGTATC TGCAAATGAA      420

CAGCCTGAGA GCCGAGGACA CGGCCGTATA TTACTGTGCG AAAGACACAG TGAGGGGAAG      480

TCATTGTGAG CCCAGACACA AACCTCCCTG CAGG                                 514

(2) INFORMATION FOR SEQ ID NO:24:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:24:

CCCAGAGACC ATCACACAAC AGCCACATCC CTCCCCTACA GAAGCCCCCA GAGCGCAGCA       60

CCTCACCATG GACTGCACCT GGAGGATCCT CTTCTTGGTG GCAGCAGCTA CAGGCAAGAG      120

AATCCTGAGT TCCAGGTCTG ATGAGGGGAC TGGGTCCAGT TAAGTGGTGT CTCATCCACT      180

CCTCTGTCCT CTCCACAGGC ACCCACGCCC AGGTCCAGCT GGTACAGTCT GGGGCTGAGG      240

TGAAGAAGCC TGGGGCCTCA GTGAAGGTCT CCTGCAAGGT TTCCGGATAC ACCCTCACTG      300

AATTATCCAT GCACTGGGTG CGACAGGCTC CTGGAAAAGG GCTTGAGTGG ATGGGAGGTT      360

TTGATCCTGA AGATGGTGAA ACAATCTACG CACAGAAGTT CCAGGGCAGA GTCACCATGA      420

CCGAGGACAC ATCTACAGAC ACAGCCTACA TGGAGCTGAG CAGCCTGAGA TCTGAGGACA      480
```

```
CGGCCGTGTA TTACTGTGCA ACAGACACAG TGTGAAAACC CACATCCTGA GAGCGTCAGA        540

AACCCTGAGG AATGAGGCAG CTGTGCTGAG GCTGAGGAGA TGACAGGATT TATGAAGTTT        600

(2) INFORMATION FOR SEQ ID NO:25:

(i) SEQUENCE CHARACTERISTICS:
        (A) LENGTH: 655 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:25:

ATTCACGTTT TCGAGCTCGG TACCCGGGGG ATCCTCTAGA GTCGACCTGC AGCTCTGGGA         60

GAGGAGCCCA GCCCCCGAAT TCCCAGGTGT TTTCATCTGG TGATCAGCAC CGAACACAGA        120

GGACTCACCA TGGAGTTTGT GCTGAGCTGG GTTTTCCTTG TTGCTATTTT AAAACGTGAT        180

CTATAGAGAA CTAGAGATAT TGAGTATGAA TGGATATGAG TGAGAAACAG TGGATACGTG        240

TGGCAGTTTC TGACCGGGGT GTCTCTGTGT TTGCAGGTAT CCAGTGTGAG ATGCAGCTGG        300

TGGAGTCTGG GGGAGGCTTG CAAAAGCCTG CGTGGTCCCC GAGACTCTCC TGTGCAGCCT        360

CTCAATTCAC CTTCAGTAGC TACTACATGA ACTGTGTCCG CCAGGCTCCA GGGAATGGGC        420

TGGAGTTGGT TTGACAAGTT AATCCTAATG GGGGTAGCAC ATACCTCATA GACTCCGGTA        480

AGGACCGATT CAATACCTCC AGAGATAACG CCAAGAACAC ACTTCATCTG CAAATGAACA        540

GCCTGAAAAC CGAGGACACG GCCCTCTATT AGTGTACCAG AGACACAGTG AGGGGAGGTC        600

AGTGTGAGCC CAGACACAAA CCTCCCTGCA GGCATGCAAG CTTGGCACTG ACCGT            655

(2) INFORMATION FOR SEQ ID NO:26:

(i) SEQUENCE CHARACTERISTICS:
        (A) LENGTH: 546 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:26:

AGTGACTCCT GTGCCCCACC ATGGACACAC TTTGCTACAC ACTCCTGCTG CTGACCACCC         60

CTTCCTGTGA GTGCTGTGGT CAGGGACTTC CTCAGAAGTG AAACATCAGT TGTCTCCTTT        120

GTGGGCTTCA TCTTCTTATG TCTTCTCCAC AGGGGTCTTG TCCCAGGTCA CCTTGAAGGA        180

GTCTGGTCCT GTGCTGGTGA AACCCACAGA GACCCTCACG CTGACCTGCA CCGTCTCTGG        240

GTTCTCACTC AGCAATGCTA GAATGGGTGT GAGCTGGATC CGTCAGCCCC CAGGGAAGGC        300

CCTGGAGTGG CTTGCACACA TTTTTTCGAA TGACGAAAAA TCCTACAGCA CATCTCTGAA        360

GAGCAGGCTC ACCATCTCCA AGGACACCTC CAAAAGCCAG GTGGTCCTTA CCATGACCAA        420

CATGGACCCT GTGGACACAG CCACATATTA CTGTGCACGG ATACCACAGA GACACAGCCC        480

AGGATGCCTC CTGTACAAGA ACCTAGCTGC ATCTCAGTGG TGCTCCCTCC CTACCTCTGC        540
```

```
AGAACA                                                                   546

(2) INFORMATION FOR SEQ ID NO:27:

(i) SEQUENCE CHARACTERISTICS:
        (A) LENGTH: 587 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:27:

TGAGAGCATC ATCCAACAAC CACAACTCTC CTCAGAAGAA GCCCCTAGAC CACAGCACCT          60

CAACATGTAC TGGACCTGGA GGATCCTCTT CTTGGTGGCA GCAGCAACAG GTAAGGGACC        120

TCCCAGTCAC CGGGCTGAGA GAGAAACCAG GCCAGTCAAG TGAGACTTCA CGCACTCCTG        180

TCTCCTCTCC ACAGGTGTCC ACTCACAGGT GCAGCTGGTG CAGTCTGGGC CTGAGGTGAA        240

GAAGCCTGGA GCCTCATTGA AGGTTTCCTG CAAGGCTTCT GGATACACCT TCACAAGCTA        300

TGCTATCAGC TGGGTATGAC AGGCCCATGG ACAAGGGCTT GAGGAAATGG GATGGATCAA        360

CACCAACACT GGGAACCTAA CGTATGCCCA GGGCTTCACA GGACGGTTTG TCTTCTCCAT        420

GGACACCTCC GTCAGCATGG CATATCTTCA TATCAGCAGC CTAAAGGCTG AGGACACGTG        480

CAAGAGGCAC AGTGTGGAAA CCCACATCCT GAGAGAACCA GAAATCCTGA GGGAGGAGGC        540

AGCTGTGCTG AGCTGAGGCA GTGACAGGGA CAACGTGGCT GCACCCT                      587

(2) INFORMATION FOR SEQ ID NO:28:

(i) SEQUENCE CHARACTERISTICS:
        (A) LENGTH: 624 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:28:

CATCCCTTTT CACCTCTCCA TACAGAGGCA CCACCCACAT GCAAATCTCA CTTAGGCACC         60

CAAGGGAAAC CATCACACAT TTCCTTAAAT TCAGGGTCCT GCTCACATGG GAAATACTTT        120

CTGAGAGCTC TGGACCTCCT GTGCAAGAAC ATGAAACACC TGTGGTTCTT CCTCCTGCTG        180

GTGGCAGCTC CCAGATGTGA GTGTCTCAAG GCTGCAGACA TGGAGATATG GAGGTGCCT         240

CTGAGCCCAG GGCTCACTGT GGGTCTCTCT GTTCACAGGG GTCCTGTCCC AGGTGCAGCT        300

GCAGGAGTCG GGCCCAGGAC TGGTGAAGCC TTCGACACC  CTGTCCCTCA CCTGCGCTGT        360

CTCTGGTTAC TCCATCAGCA GTAGTAACTG GTGGGGCTGG ATCCGGCAGC CCCCAGGGAA        420

GGGACTGGAG TGGATTGGGT ACATCTATTA TAGTGGGAGC ACCTACTACA ACCCGTCCCT        480

CAAGAGTCGA GTCACCATGT CAGTAGACAC GTCCAAGAAC CAGTTCTCCC TGAAGCTGAG        540

CTCTGTGACC GCCGTGGACA CGGCCGTGTA TTACTGTGCG AGAAACACAG TGAGGGGAGG        600
```

```
TGAGTGTGAG CCCAGACACA AACC                                                 624

(2) INFORMATION FOR SEQ ID NO:29:

(i) SEQUENCE CHARACTERISTICS:
        (A) LENGTH: 304 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:29:

GTCAGATACA CCATGCAGAC TCTGTGAAGG GCAGATTCTC CATCTCCAAA GACAATGCTA            60

AGAACTCTCT GTATCTGCAA ATGAACAGTC AGAGAACTGA GGACATGGCT GTGTATGGCT           120

GTACATAAGG TTCCAAGTGA GGAAACATCG GTGTGAGTCC AGACACAAAA TTTCCTGCAA           180

AAAGAAGAAA GGAGTCTGGG CCAAAGGGGA CACTCAGCAC TCACAAAACA GGTGCAGCCC           240

CACGGCAGGT GCAGATGGAG GGAGGGTAAG GGCTGNTTTC CTTCAGGATC TGTGGGTTTC           300

CTCT                                                                       304

(2) INFORMATION FOR SEQ ID NO:30:

(i) SEQUENCE CHARACTERISTICS:
        (A) LENGTH: 512 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:30:

GGACTCACCA TGGAGTTTGG GCTGAGCTGG GTTTTCCTCG TTGCTCTTTT AAGAGGTGAT            60

TCATGGAGAA ATAGAGAGAC TGAGTGTGAG TGAACATGAG TGAGAAAAAC TGGATTTGTG           120

TGGCATTTTC TGATAACGGT GTCCTTCTGT TTGCAGGTGT CCAGTGTCAG GTGCAGCTGG           180

TGGAGTCTGG GGGAGGCGTG GTCCAGCCTG GGAGGTCCCT GAGACTCTCC TGTGCAGCCT           240

CTGGATTCAC CTTCAGTAGC TATGGCATGC ACTGGGTCCG CCAGGCTCCA GGCAAGGGGC           300

TGGAGTGGGT GGCAGTTATA TCATATGATG GAAGTAATAA ATACTATGCA GACTCCGTGA           360

AGGGCCGATT CACCATCTCC AGAGACAATT CCAAGAACAC GCTGTATCTG CAAATGAACA           420

GCCTGAGAGC TGAGGACACG GCTGTGTATT ACTGTGCGAG AGACACAGTG AGGGGAAGTC           480

ATTGTGCGCC CAGACACAAA CCTCCCTGCA GG                                        512

(2) INFORMATION FOR SEQ ID NO:31:

(i) SEQUENCE CHARACTERISTICS:
        (A) LENGTH: 631 base pairs
        (B) TYPE: nucleic acid
        (C) STRANDEDNESS: double
        (D) TOPOLOGY: linear (ii) MOLECULE TYPE: Genomic DNA
```

(vi) ORIGINAL SOURCE:
    (A) ORGANISM: Homo sapiens
    (G) CELL TYPE: human lymphoblast
    (H) CELL LINE: CGM1

(xi) SEQUENCE DESCRIPTION: SEQ ID NO:31:

```
CATCCCTTTT CACCTGTCCA TAGAGAGGCA CCAGCCACAT GCAAATCTCA CTTAGGCACC      60
CACAGAAAAC CGCCACACAT TTCCTTAAAA TCAGGGTCCT GCTCACATGG GAAATACTTT     120
CTGAGAGTCC TGGACCTCCT GTGCGAGAAC ATGAAACACC TGTGGTTCTT CCTCCTGCTG     180
GTGGCAGCTC CCAGATGTGA GTGTCTCAAG GCTGCAGACA TGGAGATATG GGAGGTGCCT     240
CTGATCCCAG GGCTCACTGT GTGTCTCTCT GTTCACAGGG GTCCTGCCCC AGGTGCAGCT     300
GCAGGAGTCG GGCCCAGGAC TGGTGAAGCC TTCACAGACC CTGTCCCTCA CCTGTACTGT     360
CTCTGGTGGC TCCATCAGCA GTGGTGGTTA CTACTGGAGC TGGATCCGCC AGCACCCAGG     420
GAAGGGCCTG GAGTGGATTG GGTACATCTA TTACAGTGGG AGCACCTACT ACAACCCGTC     480
CCTCAAGAGT CGAGTTACCA TATCAGTAGA CACGTCTAAG AACCAGTTCT CCCTGAAGCT     540
GAGCTCTGTG ACTGCCGCGG ACACGGCCGT GTATTACTGT GCGAGAGACA CAGTGAGGGG     600
AGGTGAGTGT GAGCCCAGAC ACAAACCTCC C                                   631
```

(2) INFORMATION FOR SEQ ID NO:32:

(i) SEQUENCE CHARACTERISTICS:
       (A) LENGTH: 341 base pairs
       (B) TYPE: nucleic acid
       (C) STRANDEDNESS: double
       (D) TOPOLOGY: linear (ii) MOLECULE TYPE: Genomic DNA (vi) ORIGINAL SOURCE:
       (A) ORGANISM: Homo sapiens
       (G) CELL TYPE: human lymphoblast
       (H) CELL LINE: CGM1

(xi) SEQUENCE DESCRIPTION: SEQ ID NO:32:

```
ACCAGTCTCC AGGCAAGGGG CTGGAGTGAG TAATAGATAT AAAAGATGAT GGAAGTCAGA      60
TACACCATGC AGACTCTGTG AAGGGCAGAT TCTCCATCTC CAAAGACAAT GCTAAGAACT     120
CTCTGTATCT GCAAATGAAC ACTCAGAGAG CTGAGGACGT GGCCGTGTAT GGCTATACAT     180
AAGGTCCCAA GTGAGGAAAT ATCGGTGTGA GTCCAGACAC AACATTTCCT GCAAAAAGAA     240
GAAAGGAGTC TGGGCCGAAG GGGACACTCA GCACTCACAA AACAGGTGCA GCCCCACGGC     300
AGGTGCAGAT GGAGGGAGGG TAAGGGCTGC TTTTCCTTCA G                        341
```

(2) INFORMATION FOR SEQ ID NO:33:

(i) SEQUENCE CHARACTERISTICS:
       (A) LENGTH: 583 base pairs
       (B) TYPE: nucleic acid
       (C) STRANDEDNESS: double
       (D) TOPOLOGY: linear (ii) MOLECULE TYPE: Genomic DNA (vi) ORIGINAL SOURCE:
       (A) ORGANISM: Homo sapiens
       (G) CELL TYPE: human lymphoblast
       (H) CELL LINE: CGM1

(xi) SEQUENCE DESCRIPTION: SEQ ID NO:33:

```
TGAACACAGA GGACTCACCA TGGAGTTTGG GCTGAGCTGG GTTTTCCTCG TTGCTCTTTT      60
```

```
AAGAGGTGAT TCATTGGAGA AATAGAGAGA CTGAGTGTGA GTGAACATGA GTGAGAAAAA      120

CTGGATTTGT GTGGCATTTT CTGATAACGG TGTCCTTCTG TTTGCAGGTG TCCAGTGTCA      180

GGTACAGCTG GTGGAGTCTG GGGGAGGCGT GGTCCAGCCT GGGAGGTCCC TGAGACTCTC      240

CTGTGCAGCG TCTGGATTCA CCTTCAGTAG CTATGGCATG CACTGGGTCC GCCAGGCTCC      300

AGGCAAGGGG CTGGAGTGGG TGGCAGTTAT ATGGTATGAT GGAAGTAATA AATACTATGC      360

AGACTCCGCG AAGGGCCGAT TCACCATCTC CAGAGACAAT TCCACGAACA CGCTGTTTCT      420

GCAAATGAAC AGCCTGAGAG CCGAGGACAC GGCTGTGTAT TACTGTGCGA GAGACACAGT      480

GAGGGGAGGT CATTGTGCGC CCAGACACAA ACCTCCCTGC AGGAACGCTG GCGGGAAATC      540

AGCTGCAGGG GGGGCTCAGG AGCCACTGAT CAGAGTCAGC CCT                       583
```

(2) INFORMATION FOR SEQ ID NO:34:

(i) SEQUENCE CHARACTERISTICS:
        (A) LENGTH: 687 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:34:

```
AAAAGACTGG GCCCTCCCTC ATCCCTTTTT ACCTATCCAT ACAAAGGCAC CACCCACATG       60

CAAATCCTCA CTTAGGCACC CACAGGAAAT GACTACACAT TTCCTTAAAT TCAGGGTCCA      120

GCTCACATGG GAAGTGCTTT CTGAGAGTCA TGGACCTCCT GCACAAGAAC ATGAAACACC      180

TGTGGTTCTT CCTCCTCCTG GTGGCAGCTC CCAGATGTGA GTGTCTCAGG AATGCGGATA      240

TGAAGATATG AGATGCTGCC TCTGATCCCA GGGCTCACTG TGGGTTTCTC TGTTCACAGG      300

GGTCCTGTCC CAGGTGCAGC TACAACAGTG GGGCGCAGGA CTGTTGAAGC CTTCGGAGAC      360

CCTGTCCCTC ACCTGCGCTG TCTATGGTGG GTCCTTCAGT GGTTACTACT GGAGCTGGAT      420

CCGCCAGCCC CCAGGGAAGG GGCTGGAGTG GATTGGGGAA ATCAATCATA GTGGAAGCAC      480

CAACTACAAC CCGTCCCTCA AGAGTCGAGT CACCATATCA GTAGACACGT CCAAGAACCA      540

GTTCTCCCTG AAGCTGAGCT CTGTGACCGC CGCGGACACG GCTGTGTATT ACTGTGCGAG      600

AGGCACAGTG AGGGGAGGTG AGTGTGAGCC CAGACAAAAA CCTCCCTGCA GGTAGGCAGA      660

GGGGGCGGGC GCAGGTACTG CTCAAGA                                         687
```

(2) INFORMATION FOR SEQ ID NO:35:

(i) SEQUENCE CHARACTERISTICS:
        (A) LENGTH: 700 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:35:

```
AAATAGGAGA CATNCAAATA GGCCCCCCCC TTTCCTGATA AAAGCAGCC CAGTCCTGAC        60
```

```
CCTGCAGCCC TGGGAGAGAA GCACCAGCCC TGGGATTCTC AGGTGTTTCC ACTTTGTCAT      120

CAGCAACAAA CAAATTACCA TGGAATTTGG CCTGAGCTGG GTTTTCCTTG CTGCTATTTT      180

AAAAGGTGAT TCATGAAGAA CTAAGGATAT TGAGTGAGTG GACATGAGTG AGAGAAACAG      240

TGGATTTGTG TGGCAGTTTC TGACCAGGGT GTCTCTGTGT TTGCAGGTGT CCAGTGTGAG      300

GTGCAGCTGG TGGAGTCTGG GGGAGGCTTG GTACAGCCTG GGGGATCCCT GAGACTCTCC      360

TGTGCAGCCT CTGGATTCAC CTTCAGTAAC AGTGACATGA ACTGGGTCCA TCAGGCTCCA      420

GGAAAGGGGC TGGAGTGGGT ATCGGGTGTT AGTTGGAATG GCAGTAGGAC GCACTATGCA      480

GACTCTGTGA AGGGCCGATT CATCATCTCC AGAGACAATT CCAGGAACAC CCTGTATCTG      540

CAAACGAATA GCCTGAGGGC CGAGGACACG GCTGTGTATT ACTGTGTGAG AAACACTGTG      600

AGAGGTCGGA AGTGTGAGCC CAGACACAAA CCTCCTGCAG GAACGTTGGG GGAAATCAGC      660

TGCAGGGGGC GCTCAGGACC CACTCATCAG AGTCAACCCC                            700

(2) INFORMATION FOR SEQ ID NO:36:

(i) SEQUENCE CHARACTERISTICS:
          (A) LENGTH: 806 base pairs
          (B) TYPE: nucleic acid
          (C) STRANDEDNESS: double
          (D) TOPOLOGY: linear (ii) MOLECULE TYPE: Genomic DNA (vi) ORIGINAL SOURCE:
          (A) ORGANISM: Homo sapiens
          (G) CELL TYPE: human lymphoblast
          (H) CELL LINE: CGM1

(xi) SEQUENCE DESCRIPTION: SEQ ID NO:36:

TGACACTAAC TCCCCCAGGA TCTCACATCT GCTCTGGANA CGGCTCTCCT GTTGTCCCTA       60

CCCCAGAGCT TGCTATAGAG GAGGAGACAT CCACATAGGG CCCTCNCTTG TCCTGATGAA      120

AACCAGCCTT GCCTGCGTCT ACGGGAGAAG AGCCCCAGTC CAGAAGTACC AGGGGTTTCC      180

ATTTGGTGGT CAGGTCTCTG AACACAGAGG ACTCACTATG GAGTTTGGGC TGAGCTGGGG      240

TTTCCATGTT GCTAATGTAA AAGGTGACTC ATGGAGAACT AGAGATATTG AGTGTGAGTG      300

GACACAAGTG AGAGAAACAG TGGATATGTG TGGCAGGTTC TGACCAGGGT GTCTGTGTGT      360

GTTTGCAGGT GTCCAGTGTG AGGTGCACCT GGTGGAGTCT TTGGGAGGCT TGTTATAGCC      420

TGGGGGTCCC TGAGACTTTC TTTTGCAGCC TCTGGATTCA CCTTTAGTAC CTTTATTAGG      480

TACTGGATGA GCTGGGTCCA TCAGGCTCCT GGGAAAGGGC TGGAGTAGGT CTCATTTATG      540

AGTTGTTGTG TAGGTAGCAC AAGCTATGCA GACTCTGTGA AGGGTCGATT CACCCTCTCC      600

AGAGATGATG CCAAGAAATC ACTGTATCTG CAAATGAACA GCGTCAGAGC CGAGGATAGG      660

TCTGTGTATT ACTGTGGTGG CATTGTGTGC ATCCCTTGTT TAGGTACATG CAGAGATGCT      720

GCTTTGGTGT GTTCAGGGGC TCCTGTTTTG GGGACACCAA TTTTGGAGTT TGCAGTATCC      780

TTGAGTCCAG TACGTTCATG GTGGCA                                          806

(2) INFORMATION FOR SEQ ID NO:37:

(i) SEQUENCE CHARACTERISTICS:
          (A) LENGTH: 500 base pairs
          (B) TYPE: nucleic acid
          (C) STRANDEDNESS: double
          (D) TOPOLOGY: linear (ii) MOLECULE TYPE: Genomic DNA
```

(vi) ORIGINAL SOURCE:
              (A) ORGANISM: Homo sapiens
              (G) CELL TYPE: human lymphoblast
              (H) CELL LINE: CGM1

(xi) SEQUENCE DESCRIPTION: SEQ ID NO:37:

```
GGAATCACCA TGTTGTTTGG ACTGAGCTGG CCGTTCCGAT TTACTATTTT AAGGGGTGAC      60

ACGTGAAGCA CTACAGATAT TGCTCGTGAG TGGATATTAG AGAAACAGTG GATATGTGTG     120

GCAGTTTCTG ACCAGGATGT CTCTGTGTTT ACAGGTGTGC AGTATGAGGT GCAGCTGGTA     180

GAGTCTGGGG GAGACTTGGT ACAGCTGTGG TGGGTCCTGA GACTCTCATG TGCAGCCTGT     240

GGATTCATCT TGAGAAGCAA CTGGTCCCAC CGGGCTTCAC GAAAGGGGCT GGCATGGAAT     300

GACATGGTCT CATACATTAG TGCTAGTGGT GGTAGTCTAT ACTATGCAGA CACTGAAGGG     360

TAGATTCACC ATCTCTAGAG ACAATGGCAA GAACATGCTG TTCTTGCAAA TGAACAGTCT     420

GAGAGATGAG GACTCGGTTG TGTTGAGAGA CATGGTGAGG GGAAAATCAG TATGAGCCCA     480

GCCAGAACTC TCCCTGCAGG                                                 500
```

(2) INFORMATION FOR SEQ ID NO:38:

(i) SEQUENCE CHARACTERISTICS:
              (A) LENGTH: 507 base pairs
              (B) TYPE: nucleic acid
              (C) STRANDEDNESS: double
              (D) TOPOLOGY: linear (ii) MOLECULE TYPE: Genomic DNA (vi) ORIGINAL SOURCE:
              (A) ORGANISM: Homo sapiens
              (G) CELL TYPE: human lymphoblast
              (H) CELL LINE: CGM1

(xi) SEQUENCE DESCRIPTION: SEQ ID NO:38:

```
CAACTCATCA TGCAGTTTGT GCTGAGCTGG GTTTTCCTTG TTGGTATTTT AAAAGGTGAT      60

TCATGGAGAA CTACAGATGT TGAGTGTGAG TGGACATGAG TGAGCCAAAC AGTGGGTTTG     120

TGTGGCAGTT TCTGACCTGG TGTCTCTGTG TTTACAGGTG TCCAGTGTGA GGTGCAGCTG     180

GTGGAGTCTG GGGGAGGCTT GGTACAGCCT AGGGGGTCCC TGAGACTCTC CTGTGCAGCC     240

TCTGGATTCA CCGTCAGTAG CAATGAGATG AGCTGGATCC GCCAGGCTCC AGGGAAGGGG     300

CTGGAGTGGG TCTCATCCAT TAGTGGTGGT AGCACATACT ACGCAGACTC CAGGAAGGGC     360

AGATTCACCA TCTCCAGAGA CAATTCCAAG AACACGCTGT ATCTTCAAAT GAACAACCTG     420

AGAGCTGAGG GCACGGCCGC GTATTACTGT GCCAGATATA CACAGAGGGG AAGTCATTGT     480

GCGCCCAGAC ACAAACCTCC CTGTAGG                                         507
```

(2) INFORMATION FOR SEQ ID NO:39:

(i) SEQUENCE CHARACTERISTICS:
              (A) LENGTH: 800 base pairs
              (B) TYPE: nucleic acid
              (C) STRANDEDNESS: double
              (D) TOPOLOGY: linear (ii) MOLECULE TYPE: Genomic DNA (vi) ORIGINAL SOURCE:
              (A) ORGANISM: Homo sapiens
              (G) CELL TYPE: human lymphoblast
              (H) CELL LINE: CGM1

(xi) SEQUENCE DESCRIPTION: SEQ ID NO:39:

```
AGAAGAGGAC TCTGGGCTTG GAGAGGGGAG CCCCCCAAGA AGAGAAACTT GATTCTCCAA      60

AGGGCACAGC CAGCATTCTC CTCCCAGGGT GAGCTCCAAA AGACTGGCGC CTCTCTCATC     120

CCTTTTCACT GCTCCGTACA AACGCACNCA CCCCCATGCA AATCCTCACT TAGGCGCCCA     180

CAGGAAGCCA CCACACATTT CCTTAAATTC AGGTCCAACT CATAAGGGAA ATGCTTTCTG     240

AGAGTCATGG ATCTCATGTG CAAGAAAATG AAGCACCTGT GGTTCTTCCT CCTGCTGGTG     300

GCGGCTCCCA GATGTGAGTG TTTCTAGGAT GCAGACATGG AGATATGGGA GGCTGCCTCT     360

GATCCCAGGG CTCACTGTGG GTTTTTCTGT TCACAGGGGT CCTGTCCCAG CTGCAGCTGC     420

AGGAGTCGGG CCCAGGACTG GTGAAGCCTT CGGAGACCCT GTCCCTCACC TGCACTGTCT     480

CTGGTGGCTC CATCAGCAGT AGTAGTTACT ACTGGGGCTG GATCCGCCAG CCCCCAGGGA     540

AGGGGCTGGA GTGGATTGGG AGTATCTATT ATAGTGGGAG CACCTACTAC AACCCGTCCC     600

TCAAGAGTCG AGTCACCATA TCCGTAGACA CGTCCAAGAA CCAGTTCTCC CTGAAGCTGA     660

GCTCTGTGAC CGCCGCAGAC ACGGCTGTGT ATTACTGTGC GAGACACACA GTGAGGGGAG     720

GTGAGTGTGA GCCCAGACAA AAACCTCCCT GCAGGGAGGC TGAGGGGCG GTCGCAGGTG      780

CAGCTCAGNG CCAGCAGGGG                                                 800

(2) INFORMATION FOR SEQ ID NO:40:

(i) SEQUENCE CHARACTERISTICS:
        (A) LENGTH: 970 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
         (A) ORGANISM: Homo sapiens
         (G) CELL TYPE: human lymphoblast
         (H) CELL LINE: CGM1

(xi) SEQUENCE DESCRIPTION: SEQ ID NO:40:

CACAACCTCC ATGAAAAACA ACATAGAAAT TTCTCAAAGA ACTAAAATTA GAATTACCAT      60

TTCTTCCAGT AAGCTGTCCC AGTAGGCATG TTCCTCCCAA ACTTTTATNT CAGAGAATGT     120

TGCCTGCACT CATATGTTTA TTTCAACACC ATTTTCAATA GAAAAGTCAA ATAATCTAAG     180

TGTCAATCAG TGGATGATTA GATAAAAATAT GATATNNATG TAAATCATNG GAATACTATG    240

CAGCCAGTAT GGTATGAATT CAGTNGTGAN NCCNAGCCCC TGGACAAGNN GGCTTGAGTG     300

GATGGGATGG ATCATCACCT ACACTGGGAA CCCAACATAT ACCAACGGCT TCACAGGACG     360

GGTTTCTATT CTCCATGGGA CACCTCTGTC AGCATGGCGT ATCTGAAGAT CAGCAGCCTA     420

AAGGCTGAGG ACACGGCCGC GTATGACTGT ATGAGAGACA CAGGGTGGAA ACCCACATCC     480

CGAGGGAGTC AGAAACCCCG GGGGAGGAGC CACCTGTTCT GACCTGAGNC AGTGGTCCAA     540

NCAGTNTCTT TAACNTCCAT ATGATCTCAT TTTTGCATCA TCTTCTACTT TTATATTAGC     600

TAAGAACTTG GGGTAGACAG GTGCTCCTAA GAGATCCTTA ACTTGCCCAT TTTGATGGGT     660

TTTCCAGAAG ACGTGAGAAG CCACTTTGTT ANCAAAGCAT CCCAAATCCA TGCCCTGTTN     720

CTAGATACAT GTGAGCCCAT TTCCTGGTCT TTGCTTAACT GACAAGCTCT CATCAGTGCA     780

CCTGGGCTAA TTTCACATCA GGTAGAGGAA CGCGTTATAA AGGAAAGCTA ATGTTGTAAT     840

AGCAATTCCT GCTTAAAAAC CTTCAGCTTC ATTGTTTTTG TGTAATCCAT CANCAAATTA    900

TGTTAGTTCA AGGTTCTCAA TGGGAGTTTC TAATAAATAG AAAGGATGTA TAAAGCTTGN    960
```

(2) INFORMATION FOR SEQ ID NO:41:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:41:

```
CCCCACTCTC TCCTCAGNCG TCCCATCCCA GAGCTTGGCA TTGTAGTAGG AGACATCCAA      60

ATAGAGCCCT CCCTCTGCTT ATGAAAACCA GCCCAGCCCT GACCCTGCAG CTGTGGGAGA     120

GGAGCCCCAG CCCTGGGATT TTCAGGTGCT TCATTTTGT GATCAGGACT GAACACAGAG      180

GATTCACCAT GGAGTCATGG CTGAGCTGGG TTTTTCTTGC CGCTATTTTA AAAGGTAATT     240

CATTGAGAAC TATTGAAATT GAGTGTGAGT GGATAAGAGT GAGATAAACA GTGGATACGT     300

GTGGCAGTTT CTGACCAGGG TTTCTTTGTG TTTGCAGGTG TCCAGTGTGA GGTGCAGCTG     360

GTGGAGTCTG GGGGAGGCTT GGTCCAGCCT GGGGGGTCCC TGAGACTCTC CTGTGCAGCC     420

TCAGGATTCT CCTTTAGTAG CTATGGCATG AGCTGGGTCC GCCAGGCTCC AGGGAAGGGG     480

CTGGAGTGAG TGGCACATAT CTGGAATGAT GGAAGTCAGA AATACTATGC AGACTCTGTG     540

AAGGGCCGAT TCACAATCTC CGAGACAATT CTAAGAGCAT GCTCTATCTG CAAATGGACA     600

GTCTGAAAGC TAAGGACACG GCCATGTATT ACTGTACCAG ACACAGTGAG AGGAAGTCCG     660

TGTGAGCCCA GACACAAACC TCCCTGCAGG GGCACGCGGG GCCACCAGAG GGTGCCCAGG     720

ATCCCCTGAA GACAGGGACA GNCCAAAGGC AGGTGCAGAT GGNTGTCAAG AGGGTCTTGT     780

GGCTTCGTCT ACATCTAACT GGTTTCCTGG GTGAGCCTC                           819
```

(2) INFORMATION FOR SEQ ID NO:42:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:42:

```
TTGTAGGTGA TTTATGGAGA ATGAGAGATG TTGAGTGCGA GTGGACATGA GTGAGAGAAA      60

CAGTAGATAT GTGTGCCCGT TTCTGACCAG GGTGTCTCTG TGTTTGCAGG CGTCCAGCGT     120

GAGGCGCAGC TGGTGGAGTC TGGGGGAGAC TTGGTACAAC CTGGGTGGGT CCCCGAGACT     180

CTCATTTGCA GCTTCTAGAT TCACCTTCAG TGACTTCTGA ATGCACTGGA TCCGCCAGGC     240

TTCTGGGAAA GGGCTGGAGT GGGTTGGCCG TATTAGAACC AAACGTAACA GTTACACGAC     300

AGAATGCGCT GCATCTGTGA AAGGCAGGTT CACCATCTCA AGAGATGATT CAAAGAACAC     360

ACTGTATCTG CAAGTGAATA CCCTGAAAAC CGAGTACACG GCCATCTATT ACTGTACTAG     420
```

```
AGACAGTGAG GGGGAGGTTA ACGTAGGCCC ATACACAAAT CTCCCTGCAG G            471
```

(2) INFORMATION FOR SEQ ID NO:43:

(i) SEQUENCE CHARACTERISTICS:
        (A) LENGTH: 870 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:43:

```
CATCTGTTAC AGAACTCATT ATATAGTAGG AGACATCCAA ATNGGGTCCC TCCCTCTGCT    60
GATGAAAACC AGCCCAGCCC TGACCCTGCA GCTCTGGGAG AGGAGCCCCA GCCCTGAGAT   120
TCCCAGGTGT TTCCATTCGG TGATCAGCAC TGAACACAGA GAACGCACCA TGGAGTTTGG   180
ACTGAGCTGG GTTTTCCTTG TTGCTATTTT AAAAGGTGAT TCATGGATAA ATAGAGATGT   240
TGAGTGTGAG TGAACATGAG TGAGAGAAAC AGTGGATATG TGTGGCAGTG TCTGACCAGG   300
GTGTCTCTGT GTTTGCAGGT GTCCAGTGTG AAGTGCAGCT GGTGGAGTCT GGGGGAGTCG   360
TGGTACAGCC TGGGGGGTCC CTGAGACTCT CCTGTGCAGC CTCTGGATTC ACCTTTGATG   420
ATTATACCAT GCACTGGGTC CGTCAAGCTC CGGGGAAGGG TCTGGAGTGG GTCTCTCTTA   480
TTAGTTGGGA TGGTGGTAGC ACATACTATG CAGACTCTGT GAAGGGCCGA TTCACCATCT   540
CCAGAGACAA CAGCAAAAAC TCCCTGTATC TGCAAATGAA CAGTCTGAGA ACTGAGGACA   600
CCGCCTTGTA TTACTGTGCA AAAGATACAC AGTGAGGGGA AGTCAGCGAG AGCCCAGACA   660
AAAACCTCGC TGCAGGAAGA CAGGAGGGGC CTGGGCTGCA GAGGCCACTC AAGACACACT   720
GAGCATAGGG TTAACTCTGG GACAAGTTGC TCAGGAAGGT TAAGAGCTGG TTTCCTTTCA   780
GAGTCTTCAC AAATTTCTCC ATCTAACAGT TTCCCCAGGA ACCNGTCTAG ATCTGTGATC   840
TTGGATCTGC TGAAACTGCC TGTGTCACCT                                   870
```

(2) INFORMATION FOR SEQ ID NO:44:

(i) SEQUENCE CHARACTERISTICS:
        (A) LENGTH: 529 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:44:

```
TCCCCGGGTA CCGAGCTCAA GTGCCAGGAT TCCCAGGTGT TTCACTTGG TGATCAGAAC    60
TTAACACAGA GGACTCACCA TGTTGTTTGG GCTGAGCTGG GCTTTCCTTG TTACTATTTT   120
AAGAGGTGAT TCATGAAGAA CTACAGATAT TGTTTGTGAG TGGATATTAG AGAAACAGTG   180
GATATGTGTG GCAGTTGCTG ACCAGGATTT CTCTGTGTTT GCAGGTGTGC AGTATGAGGT   240
GCAGCTGGTA GAGTCTTTTT TTTTTTTTTT TTTTCACTTT TTAGCGAACA TCCATGGGTT   300
```

```
ACAAAATAAT GGGTTGGCTT TTCTTCCAAC ACTTTACAGA CACCATCAAT TTTCCCCTTG      360

CTTATAAGGT TTTTAACCAG AAGAATGCTG TCATCATCTT TCCTGTTCTT TTAGGAAGAA      420

TGCCCCCTCA ACTCATCTCC ACTTGTCTGC ATGTATTTCT ATTTGTCTTG GACGTTCCCA      480

ACAGCCTCNC GAACACTCAC CTCACCCTAC AATGCTGCTC GAGGGGGTC                  529
```

(2) INFORMATION FOR SEQ ID NO:45:

(i) SEQUENCE CHARACTERISTICS:
        (A) LENGTH: 748 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:45:

```
CAGGATCAGG GCTTGAGTCA TCAGCATCTC ACTCTTGCAA AGNCTGATGT GTCGTTTGTC       60

TTCCCTTTCT TATCATCGAC CAGGCTTTGA GCTATGAAAT GCCCTGTCTC ATCAATATNC      120

AAATAACCTG AGATCGACTG AGGTAAATAT GGATATGTCT GTGCCCTGAG AGCATCACCC      180

AACAAACCAC ATCCCTCCTC TAGAGAATCC CCTGAAAGCA CAGCTCCTCA CCATGGACTG      240

GACCTGGAGA ATCCTCTTCT TGGTGGCAGC AGCCACAGGT AAGGGGCTCC CAAGTCCCAG      300

TGATGAGGAG GGGATTGAGT CCAGTCAAGG TGGCTTTTAT CCACTCCTGT GTCCCCTCCA      360

CAGATGCCTA CTCCCAGATG CAGCTGGTGC AGTCTGGGGC TGAGGTGAAG AAGACTGGGT      420

CCTCAGTGAA GGTTTCCTGC AAGGCTTCCG GATACACCTT CACCTACCGC TACCTGCACT      480

GGGTGCGACA GGCCCCCGGA CAAGCGCTTG AGTGGATGGG ATGGATCACA CCTTTCAATG      540

GTAACACCAA CTACGCACAG AAATTCCAGG ACAGAGTCAC CATTACCAGG GACAGGTCTA      600

TGAGCACAGC CTACATGGAG CTGAGCAGCC TGAGATCTGA GGACACAGCC ATGTATTACT      660

GTGCAAGATA CACAGTGTGA AAACCCACAT CCTGAGACCG TCAGAAACCC CAAGGAGGAG      720

GCAGCTTCAC TGAATGAGGA GGTTACAG                                         748
```

(2) INFORMATION FOR SEQ ID NO:46:

(i) SEQUENCE CHARACTERISTICS:
        (A) LENGTH: 799 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:46:

```
CATTTCTTCA AAGCAGGATT AGGGCTTGGA CCATCAGCAT CCCACTCCTG TGTGGCAGAT       60

GGGACATCTA TCTTCTTTCT CCAACCTCGA TCAGGCTTTT GAGGTATGAA ATAATCTGTC      120

TCATGAATAT GCAAATAACC TTAGATCTAC TGAGGTAAAT ATGGATACAT CTGGGCCCTG      180

AAAGCATCAT CCAACAACCA CATCCCTTCT CTACAGAAGC CTCTGAGAGG AAAGTTCTTC      240

ACCATGGACT GGACCTGGAG GGTCTTCTGC TTGCTGGCTG TAGCTCCAGG TAAAGGGCCA      300
```

```
ACTGGTTCCA GGGCTGAGGA AGGGATTTTT TCCAGTTTAG AGGACTGTCA TTCTCTACTG      360

TGTCCTCTCC GCAGGTGCTC ACTCCCAGGT GCAGCTGGTG CAGTCTGGGG CTGAGGTGAA      420

GAAGCCTGGG GCCTCAGTGA AGGTTTCCTG CAAGGCATCT GGATACACCT TCACCAGCTA      480

CTATATGCAC TGGGTGCGAC AGGCCCCTGG ACAAGGGCTT GAGTGGATGG GAATAATCAA      540

CCCTAGTGGT GGTAGCACAA GCTACGCACA GAAGTTCCAG GGCAGAGTCA CCATGACCAG      600

GGACACGTCC ACGAGCACAG TCTACATGGA GCTGAGCAGC CTGAGATCTG AGGACACGGC      660

CGTGTATTAC TGTGCGAGAG ACACAGTGTG AGAAACCACA TCCTCAGAGT GTCAGAAACC      720

CTGAGGGAGG AGTCAGCTGT GCTGAGCTGA GAAAATGACA GGGGTTATTC AGTTTAAGAC      780

TGTTTAGAAA ACGGGTTAT                                                   799

(2) INFORMATION FOR SEQ ID NO:47:

(i) SEQUENCE CHARACTERISTICS:
        (A) LENGTH: 627 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:47:

CCAAATAAAC ACATTAAATG TCAAGATACG CCCAAAAACT TATCTGCCTG ACCCCCTAGT       60

TGTCTCCGTA ATTTTTGGAT GAAAACCAGC CCACCCCTGA CCCTGCTGCT CTGGGAGAGG      120

AGCCCCAGCC TTGGGATTCC CAAGTGTTTG CATTCAGTGA TCAGGACTGA ACACACAGGA     180

CTCACCAGGG AGTTTGTGCT AAGCTGGGTT TTCCTTGTTG CTATATTAAA ATGTGATTCA      240

TGGAGAACTA GAGAGATTGA GTGTGAGTTA CATGAGTGAG AGAAACAGTG GATATGTTTG      300

GCAATTTCTG ACTTTTGTGT CTCTGTGTTT GCAGGTGTCC AGTGTGAGGA TCAGCTGGTG      360

GAGTCTGGGG GAGGCTTGGT ACAGCCTGGG GGGTCCCTGA GACCCTCCTG TGCAGCCTCT      420

GGATTCGCCT TCAGTAGCTA TGTTCTGCAC TGGGTTCGCC GGGCTCCAGG GAAGGGTCCG      480

GAGTGGGTAT CAGCTATTGG TACTGGTGGT GATACATACT ATGCAGACTC CGTGATGGGC      540

CGATTCACCA TCTCCAGAGA CAACGCCAAG AAGTCCTTGT ATCTCAAATG AACAGCCTGA      600

TAGCTGAGGA CATGGCTGTG TATTATG                                         627

(2) INFORMATION FOR SEQ ID NO:48:

(i) SEQUENCE CHARACTERISTICS:
        (A) LENGTH: 743 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:48:

AAGGGTCCCC ACCCTAGAGC TTGCTATATA GTAGGAGATA TCCAAATAGG NCCCTCCCTC       60
```

| TACTGATGAA | AACCCAACCC | AACCCTGACC | CTGCAGCTCT | CAGAGAGGTG | CCTTAGCCCT | 120 |
| GGATTCCAAG | GCATTTCCAC | TTGGTGATCA | GCACTGAACA | CAGAGGACTC | ACCATGGAGT | 180 |
| TGGGGCTGTG | CTGGGTTTTC | CTTGTTGCTA | TTTTAGAAGG | TGATTCATGG | AAAACTAGAG | 240 |
| AGATTTAGTG | TGTGTGGATA | TGAGTGAGAG | AAACAGTGGA | TATGTGTGGC | AGTTTCTGAC | 300 |
| CTTGGTGTCT | CTTTGTTTGC | AGGTGTCCAG | TGTGAGGTGC | AGCTGGTGGA | GTCTGGGGGA | 360 |
| GGCTTGGTAC | AGCCTGGGGG | GTCCCTGAGA | CTCTCCTGTG | CAGCCTCTGG | ATTCACCTTC | 420 |
| AGTAGCTATA | GCATGAACTG | GGTCCGCCAG | GCTCCAGGGA | AGGGGCTGGA | GTGGGTTTCA | 480 |
| TACATTAGTA | GTAGTAGTAG | TACCATATAC | TACGCAGACT | CTGTGAAGGG | CCGATTCACC | 540 |
| ATCTCCAGAG | ACAATGCCAA | GAACTCACTG | TATCTGCAAA | TGAACAGCCT | GAGAGCCGAG | 600 |
| GACACGGCTG | TGTATTACTG | TGCGAGAGAC | ACAGTGAGGG | GAGGTCAGTG | TGACACCAGA | 660 |
| CACAAACCTC | CCTGCAGGGG | TCCGCAGGAC | CACCAGGGGG | CGACAGGACA | CTGAGCACGG | 720 |
| GGCTGTCTCC | AGGGCAGGTG | CAG | | | | 743 |

(2) INFORMATION FOR SEQ ID NO:49:

(i) SEQUENCE CHARACTERISTICS:
        (A) LENGTH: 763 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:49:

| TCACCCAACT | CCTCCAGGCA | CAGTCATCTT | ATCTGGCCCC | GTCCTCTCCT | CAGNTGTCCC | 60 |
| ACCCCAGAGC | TTGGTATATA | GTAGGAGACA | TNCAAATAAG | GCCCTCCCTC | TGCTGATGAA | 120 |
| AATGAGCCCA | GCCCTGACCC | TGCAGCTCTG | GGAGAGGAGC | CCCANCCGTG | AGATTCCCAG | 180 |
| GAGTTTCCAC | TTGGTGATCA | GCACTGAACA | CAGACCACCA | ACCATGGAGT | TTGGGCTTAG | 240 |
| CTGGGTTTTC | CTTGTTGCTA | TTTTAAAAGG | TAATTCATGG | TGTACTAGAG | ATACTGAGTG | 300 |
| TGAGGGACA | TGAGTGGTAG | AAACAGTGGA | TATGTGTGGC | AGTTTCTGAC | CTTGGTGTTT | 360 |
| CTGTGTTTGC | AGGTGTCCAA | TGTGAGGTGC | AGCTGGTGGA | GTCTGGGGGA | GGCTTGGTAC | 420 |
| AGCCAGGGCG | GTCCCTGAGA | CTCTCCTGTA | CAGCTTCTGG | ATTCACCTTT | GGTGATTATG | 480 |
| CTATGAGCTG | GTTCCGCCAG | GCTCCAGGGA | AGGGGCTGGA | GTGGGTAGGT | TTCATTAGAA | 540 |
| GCAAAGCTTA | TGGTGGGACA | ACAGAATACA | CCGCGTCTGT | GAAAGGCAGA | TTCACCATCT | 600 |
| CAAGAGATGG | TTCCAAAAGC | ATCGCCTATC | TGCAAATGAA | CAGCCTGAAA | CCGAGGACA | 660 |
| CAGCCGTGTA | TTACTGTACT | AGAGACACAG | TGNGGGAGG | TCAATGTGAG | CCCAGACACA | 720 |
| GACCTCCCTG | CAGGCCCGCA | CAGAGCCACC | AGGGGGCGCT | AGG | | 763 |

(2) INFORMATION FOR SEQ ID NO:50:

(i) SEQUENCE CHARACTERISTICS:
        (A) LENGTH: 283 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
    (A) ORGANISM: Homo sapiens
    (G) CELL TYPE: human lymphoblast
    (H) CELL LINE: CGM1

(xi) SEQUENCE DESCRIPTION: SEQ ID NO:50:

| | | | | |
|---|---|---|---|---|
| TGGCTCACCA TGGAGTTAGG GCTGAGCTGG GTTTCCCTTG TCATTATATT AAAAGGCGAA | 60 |
| TAATGGAGAA CTTGAGATAT GGAGTGTGAG TGGATATGAG TGAAGAAACA GTGATTCTGT | 120 |
| GTGGCAGGTT CTGACTCAGA TGTCCTCTGT GCTTGTAGGT GTCTAGTGTG GGGTGCAGAT | 180 |
| GGTGGAGTCT TGGGGAGAGT TGGCACAANC TGAATGTGCC TGAGACTCTG CCGTGCATCC | 240 |
| TCTGAATCCA CCTTCTGTAG CTACTAGATC AGCTGAATCT GCC | 283 |

(2) INFORMATION FOR SEQ ID NO:51:

(i) SEQUENCE CHARACTERISTICS:
        (A) LENGTH: 700 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:51:

| | |
|---|---|
| AGGTTCTGGG TTATAAACNC TGTAGACTCC TCCCTTCAGG GCAGGNTGAC CAACTATGCA | 60 |
| AATGCAAGTG GGGGCCTCCC CACTTAAACC CAGGGCTCCC CTCCACAGTG AGTCTCCCTC | 120 |
| ACTGCCCAGC TGGGATCTCA GGGCTTCATT TTCTGTCCTC CACCATCATG GGGTCAACCG | 180 |
| CCATCCTCGC CCTCCTCCTG GCTGTTCTCC AAGGTCAGTC CTGCCGAGGG CTTGAGGTCA | 240 |
| CAGAGGAGAA CGGGTGGAAA GGAGCCCCTG ATTCAAATTT TGTGTCTCCC CCACAGGAGT | 300 |
| CTGTTCCGAG GTGCAGCTGG TGCAGTCTGG AGCAGAGGTG AAAAAGCCCG GGGAGTCTCT | 360 |
| GAAGATCTCC TGTAAGGGTT CTGGATACAG CTTTACCAGC TACTGGATCG GCTGGGTGCG | 420 |
| CCAGATGCCC GGGAAAGGCC TGGAGTGGAT GGGGATCATC TATCCTGGTG ACTCTGATAC | 480 |
| CAGATACAGC CCGTCCTTCC AAGGCCAGGT CACCATCTCA GCCGACAAGT CCATCAGCAC | 540 |
| CGCCTACCTG CAGTGGAGCA GCCTGAAGGC CTCGGACACC GCCATGTATT ACTGTGCGAG | 600 |
| ACACACAGTG AGAGAAACCA GCCCCGAGCC CGTCTAAAAC CCTCCACACC GCAGGTGCAG | 660 |
| AATGAGCTGC TAGAGACTCA CTCCCCAGGG GCCTCTCTAT | 700 |

(2) INFORMATION FOR SEQ ID NO:52:

(i) SEQUENCE CHARACTERISTICS:
        (A) LENGTH: 767 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:52:

| | |
|---|---|
| ACACTCACCT GCTCTGGGCT CCTCCAAACT CTCCTCAGGA TTCCCCACCC CAGAGCTTGC | 60 |

```
TATATAGTAG GAGACATCCA AACAAGAGCC NAAACCTCTG CTGATGAAAA GCAGCCCAGC        120

CCTGACCCTG CAGCTCTGGG AGAGGAGCCC CAGCTCCAGG ATTCCCAGGT CTTTCCATTT        180

AGTCTTCAGG GCTGAGCACA GAGGACTCAC CATGGAGTCT GGGCTGAGCT GGGTTTTCCT        240

TGTTGCTATT TTGAAAGGTG ATTCATGGGG AATGAGTTGA ATGTAAGTGA ATATGAGTGA        300

GAGAAACAGT GGATGTGTGC GGCAGTTTCT GACCAGGGTG TCTCTGTGTT TGCAGGTGTC        360

CAGTGTGAGG TGCAGCTGGT GGAGTCTGGG TGAGGCTTGG TACAGCCTGG AGGGTCCCTG        420

AGACTCTCCT GTGCAGCCTC TGGATTCACC TTCAGTAGCT CCTGGATGCA CTGGGTCTGC        480

CAGGCTCCGG AGAAGGGGCT GGAGTGGGTG GCCGACATAA AGTGTGACGG AAGTGAGAAA        540

TACTATGTAG ACTCTGTGAA GGGCCGATTG ACCATCTCCA GAGACAATGC CAAGAACTCC        600

CTCTATCTGC AAGTGAACAG CCTGAGAGCT GAGGACATGA CCGTGTATTA CTGTGTGAGA        660

GGCACAGTGA GGGAGGTCA GTGTGAGCCC AGACACAAAC CTCCTGCAGG GGCATCTGGA        720

GCCACAAGGG GGCGCTCAGG ATACACAGAG GGACAGGGGC AGCCCCA                     767

(2) INFORMATION FOR SEQ ID NO:53:

(i) SEQUENCE CHARACTERISTICS:
        (A) LENGTH: 724 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:53:

CCATTCGGTG ATCAGCACTG AACACAGAGG ACTCACCATG GAGTTTTGGC TGAGCTGGGT         60

TTTCCTTGTT GCTATTTTAA AAGGTGATTC ATGGAGAACT AGAGATATTG AGTGTGAGTG        120

AACACGAGTG AGAGAAACAG TGGATATGTG TGGCAGTTTC TAACCAATGT CTCTGTGTTT        180

GCAGGTGTCC AGTGTGAGGT GCAGCTGGTG GAGTCTGGAG GAGGCTTGAT CCAGCCTGGG        240

GGGTCCCTGA GACTCTCCTG TGCAGCCTCT GGGTTCACCG TCAGTAGCAA CTACATGAGC        300

TGGGTCCGCC AGGCTCCAGG GAAGGGGCTG GAGTGGGTCT CAGTTATTTA TAGCGGTGGT        360

AGCACATACT ACGCAGACTC CGTGAAGGGC CGATTCACCA TCTCCAGAGA CAATTCCAAG        420

AACACGCTGT ATCTTCAAAT GAACAGCCTG AGAGCCGAGG ACACGGCCGT GTATTACTGT        480

GCGAGAGACA CAGTGAGGGG AAGTCATTGT GCGCCCAGAC ACAAACCTCC CTGCAGGAAC        540

GCTGGGGGGA AATCAGCGGN AGGGGCGCT CAGGAGCCAC TGATCAGAGT CAGCCCCGGA         600

GGCAGGTGCA GATGGAGGCT GATTTCCTTG TCAGGATGTG GGGACTTTTG TCTTCTTCTG        660

ACGGGTTCCC CAGGGGAACC TCTCTAAGTT TAGCATTCTG TGCCTATGAA CGTCTTCTCT        720

AAGT                                                                    724

(2) INFORMATION FOR SEQ ID NO:54:

(i) SEQUENCE CHARACTERISTICS:
        (A) LENGTH: 706 base pairs
        (B) TYPE: nucleic acid
        (C) STRANDEDNESS: double
        (D) TOPOLOGY: linear (ii) MOLECULE TYPE: Genomic DNA
```

-continued (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:54:

```
CTTGCTATAC AGTAGGAGAC ATGCNAATAG GTTTCTCCCT CTGCTGATGA CCAGTCCTGA        60

CCCCATAGCT CTGGGAGAGA AGCGCCAGCC CTGGGATTCC CAGGGGTTTC CATTTGGTGA       120

TCAGGACTAA AGACAGAGGA CCCACCATGG AGCTTGGGCT GAGCTGGGTT TTCACTGTTA       180

CTGTTTTAAA AGGTGAACTA GAGAGATTGA GTGTGAATGG ATACACTTGA GAGAAACAGT       240

GGATATGTCT GGAACTTTCT GACCAGGACA CCTACAAGTT TGCAGGTGTC CAGTGTGAGG       300

TACAGCTGGT GGAGTCTGAA GAAAACCAAA GACAACTTGG GGGATCCCTG AGACTCTCCT       360

GTGCAGACTC TGGATTAACC TTCAGTAGCT ACTGAATGAG CTCAGATTCC CAAGCTCCAG       420

GGAAGGGGCT GGAGTGAGTA GTAGATATAT AGTAGGATAG AAGTCAGCTA TGTTATGCAC       480

AATCTGTGAA GAGCAGATTC ACCATCTCCA AGAAAATGC CAAGAACTCA CTCTGTTTGC        540

AAATGAACAG TCTGAGAGCA GAGGGCACGG CCGTGTATTA CTGTATGTGA GTCACCAGGT       600

AAGAAGACAT CAGTGTGATC ACAGACACAG AATTTCCTGA ATAAGGGAG GAGTCTGGGC        660

TAAAAGGGCA CTCAGGACCC ACAGAAAACA GCGGAAGCTC TAGGGC                     706
```

(2) INFORMATION FOR SEQ ID NO:55:

(i) SEQUENCE CHARACTERISTICS:
        (A) LENGTH: 800 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:55:

```
GGAAGAGANC TTGATTCTCA AGAGGGCACA GCCAGCTTCC TACTCCCAGG GCAAGCCCCA        60

AAAGACTGGG NCCTCCCTCC TCCCTTTTCA CCTGTCCATA CAAAGTCACC GCCCACATGC       120

AAATCCTCAC TTAGGCACCT ACAGGAAACC AGCACACATT TCCTTAAATT TGGGATCCAG       180

CTCACATGGG AAATACTTTC TGAGACTCAT GGGCCTCCTG CACAAGAACA TGAAACACCT       240

GTGGTTCTTC CTCCTGCTGG TGGCAGCTCC CAGATGTGAG TGCCTCAGGG ATCCAGACCT       300

GAAGATATGA GATGCTGCCT CTCATCCCAG GGCTCACCGT GGTTCTCTCT GTTCACAGGG       360

GTCCTGTCCC AGGTGCAGCT GCAGGAGTCG GGCCCAGGAC TGGTGAAGCC TTCGGAGACC       420

CTGTCCCTCA TCTGCGCTGT CTCTGGTGAC TCCATCAGCA GTGGTAACTG GTGAATCTGG       480

GTCCGCCAGC CCCCAGGGAA GGGGCTGGAG TGGATTGGGG AAATCCATCA TAGTGGGAGC       540

ACCTACTACA ACCCGTCCCT CAAGAGTCGA ATCACCATGT CCGTAGACAC GTCCAAGAAC       600

CAGTTCTACC TGAAGCTGAG CTCTGTGACC GCCGCGGACA CGGCCGTGTA TTACTGTGCG       660

AGATACACAG TGAGGGGAGG TGAGTGTGAG CCCAGACACA AACCTCCCTA CAGATAGGCA       720

GAGGGGGNGG GCACAGGTGC TGCTCAGGAN CAACAGGGGG CGCGCGANGN CACAGAGCCC       780

GAGGNCCGGG TCANGAGCAG                                                  800
```

(2) INFORMATION FOR SEQ ID NO:56:

(i) SEQUENCE CHARACTERISTICS:
        (A) LENGTH: 429 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:56:

```
AGGAATTGGG CTATTCAATG CATCCTTCGT GAATATGCAA ATCACTAAGG TTAATACAGA      60

TATCTCTGTG CCGTGAGAGC ATCACCCAAC AACCACACCC CTCCTTGGAG AATCCCTAGA     120

TCACAGCTCC TCACCATGGA CTGGACCTGG AGCATCCTCT TCTTGGTGGC AGCAGCAACA     180

GGTAAGGACT CCCCAGTCCC AGGGCTGAGG GAGAAACCAG GCCAGTCATG TGAGACTTCA     240

CCCACTGCTG TCTCCTCTCC ACAGGTGCCC ACTCCCGAGT GCAGCTGGTG CAGTCTGGGC     300

CTGAGGTGAA GCAGCCTGGG GCCTCGGCGA AGGTCTCCTG CAAGGTGTCT GGTTAAACTG     360

TCATCACCTA TGGTATGAAT TGGATACGAC AGACCCCAGG ACAGGGCTT GAGTGGATGG      420

GATGGATCC                                                            429
```

(2) INFORMATION FOR SEQ ID NO:57:

(i) SEQUENCE CHARACTERISTICS:
        (A) LENGTH: 462 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:57:

```
CATCAGTTGC GCTCAGGAGT TTTAGAACAG CCTGGCAACA CATTTAGATC TGGGCTTCCC      60

TTCTCATCAC CCTCAATATT AGTGTCCCTT GTGAATCAGG TCCAGCTGCG GCTGTTCCAC     120

ATGGGGCCGT TCTTCCATTT CCTCAGTGTT TGCAGAAGTC CTGTGTGAAG TTTATTGATG     180

GAGTCAGAGG CAGAAAATTG TACAGCCCAG TGGTTCACTG AGACTCTCCT GCAAAGGCTC     240

TGATTTCACC TTTACTGGCT ACAGCATGAG CTTGGTCCAG CAGGCTTCAT GACAGGGATT     300

GGTGTGGGTG GAAACAGTGA GTAGTCAAGT GGGAGTTCTC AGAGTTACTC TCCATGAGTA     360

CAAATAAATT AACAGTCCCA AGCGACACCT TTTCATGTGC AGTCTACCTT ACAATGACCA     420

ACCTGAAAGT CCAAGGACAA GGCTGTGTAT TACTGTGAGG GA                       462
```

(2) INFORMATION FOR SEQ ID NO:58:

(i) SEQUENCE CHARACTERISTICS:
        (A) LENGTH: 629 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens (G) CELL TYPE: human lymphoblast
        (H) CELL LINE: CGM1

(xi) SEQUENCE DESCRIPTION: SEQ ID NO:58:

AGGGTCTTCA GCTATGAAAT GCTCTGACTC ATGAATATGC AAATAACCTG AGATGCACTG     60

AGGTAAATAT GGATATTTGT CAGCCCTGAG AGCATCATCC AGAAACCACA TCCCTCCGCT    120

AGAGAAGCCC TGACGGCACA GTTCCTCACT ATGGACTGGA TTTGGAGGAT CCTCTTCTTG    180

GTGGGAGCAG CGACAGGCAA GGAGATGCCA AGTCCCAGTG ATGAGGAGGG GATTGAGTCC    240

AGTCAAGGTG GCTTTCATCC ACTCCTGTGT TCTCTCCACA GGTGCCCACT CCCAAATGCA    300

GCTGGTGCAG TCTGGGCCTG AGGTGAAGAA GCCTGGGACC TCAGTGAAGG TCTCCTGCAA    360

GGCTTCTGGA TTCACCTTTA CTAGCTCTGC TGTGCAGTGG GTGCGACAGG CTCGTGGACA    420

ACGCCTTGAG TGGATAGGAT GGATCGTCGT TGGCAGTGGT AACACAAACT ACGCACAGAA    480

GTTCCAGGAA AGAGTCACCA TTACCAGGGA CATGTCCACA AGCACAGCCT ACATGGAGCT    540

GAGCAGCCTG AGATCCGAGG ACACGGCCGT GTATTACTGT GCGGCAGACA CAGTGTGAAA    600

ACCCACATCC TGAGAGTGTC AGAAACGCC                                     629

(2) INFORMATION FOR SEQ ID NO:59:

(i) SEQUENCE CHARACTERISTICS:
        (A) LENGTH: 622 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:59:

CCTCCTTTTT CACCTCTCCA TACAAAGGCA CCACCCACAT GCAAATCCTC ACTTAAGCAC     60

CCACAGGAAA CCACCACACA TTTCCTTAAA TTCAGGTTCC AGCTCACATG GGAAATACTT    120

TCTGAGAGCT CTGGACCTCC TGTGCAAGAA CATGAAACAT CTGTGGTTCT TCCTTCTCCT    180

GGTGGCAGCT CCCAGATGTG AGTATCTCAG GGATCCAGAC ATGGGGATAT GGGAGGTGCC    240

TCTGATCCCA GGGCTCACTG TGGGTCTCTC TGTTCACAGG GGTCCTGTCC CAGGTGCAGC    300

TGCAGGAGTC GGGCCCAGGA CTGGTGAAGC CTTCGGAGAC CCTGTCCCTC ACCTGCACTG    360

TCTCTGGTGG CTCCGTCAGT AGTTACTACT GGAGCTGGAT CCGGCAGCCC CCAGGGAAGG    420

GACTGGAGTG GATTGGGTAT ATCTATTACA GTGGGAGCAC CAACTACAAC CCCTCCCTCA    480

AGAGTCGAGT CACCATATCA GTAGACACGT CCAAGAACCA GTTCTCCCTG AAGCTGAGCT    540

CTGTGACCGC TGCGGACACG GCCGTGTATT ACTGTGCGAG AGACACAGTG AGGGGAGGTG    600

AGTGTGAGCC CAGACAAAAA CC                                            622

(2) INFORMATION FOR SEQ ID NO:60:

(i) SEQUENCE CHARACTERISTICS:
        (A) LENGTH: 588 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:

(A) ORGANISM: Homo sapiens
        (G) CELL TYPE: human lymphoblast
        (H) CELL LINE: CGM1

(xi) SEQUENCE DESCRIPTION: SEQ ID NO:60:

CCCGGGATTC CCAGCTGTCT CCACTTGGTC ATGAACACTG AACACAGAAG ACACACCATG         60

GAGTCTGGGC TGAGCTGGAT TTTCCTTGTT GCAGTTTTAA AAGGTGATTT ATGGAGAATA        120

GACACACTGA GTGTGACTGG ACATAAGTGA GAGAAACAGT GGATTTGTGT GGCAGTTTCT        180

GACCAGGGTG TCTCCGTGTT TGCAGGTGTC CAGTGTGAGG TGCAGCTGGT GGAGTCTGGG        240

GGAGGCTTAG TAAAGACTGG GGGGTCTCTG AGACTCTCCT GTGCAGCCTC TGGATTCACC        300

TTCAGTAGCT CTGCTATGCA CTGGGTCCAC CAGGCTCCAG GAAAGGGTTT GGAGTGGGTC        360

TCAGTTATTA GTACAAGTGG TGATACCGTA CTCTACACAG ACTCTGTGAA GGGCTGATTC        420

ACCATCTCTA GAGACAATGC CCAGAATTCA CTGTATCTGC AAATGAACAG CCTGAGAGCC        480

GACGACATGG CTGTGTATTA CTGTGTGAAA GACGCAGTGA GAAGTCAGTG TGAGCCCAGA        540

CACAAACCTC CTGCAGGGTA CCTGGGACAA CCAGGGAAAG CCTGGGAC                    588

(2) INFORMATION FOR SEQ ID NO:61:

(i) SEQUENCE CHARACTERISTICS:
        (A) LENGTH: 1212 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO:61:

CCTCCTTTTT CACCTCTCCG TACAAAGGCA CCACCCACAT GCAAATCCTT ACTTAAGCAC         60

CCACAGGAAA CCACCACACA TTTCCTTAAA TTCAGGTTCC AGCTCACATG GGAAATACTT        120

TCTGAGAGCC TGGACCTCCT GTGCAAGAAC ATGAAACACC TGTGGTTCTT CCTCCTCCTG        180

GTGGCAGCTC CCAGATGTGA GTGTCTCAGG GATCCAGACA TGGGGGTATG GGAGGTGCCT        240

CTGATCCCAG GGCTCACTGT GGGTCTCTCT GTTCACAGGG GTCCTGTCCC AGGTGCAGCT        300

GCAGGAGTCG GGCCCAGGAC TGGTGAAGCC TTCGGAGACC CTGTCCCTCA CCTGCACTGT        360

CTCTGGTGGC TCCGTCAGCA GTGGTAGTTA CTACTGGAGC TGGATCCGGC AGCCCCCAGG        420

GAAGGGACTG GAGTGGATTG GGTATATCTA TTACAGTGGG AGCACCAACT ACAACCCCTC        480

CCTCAAGAGT CGAGTCACCA TATCAGTAGA CACGTCCAAG AACCAGTTCT CCCTGAAGCT        540

GAGCTCTGTG ACCGCTGCGG ACACGGCCGT GTATTACTGT GCGAGAGACA CAGTGAGGGG        600

AGGTGAGTGT GAGCCCAGGA CACAAACCTC CCTCATGGAC GCGGAGGGGA CCGGCGCAGG        660

TGCTGCTCAG GACCAGCAGG TGGCGCGCGG GGCCCCCAGA GCATGAGGCC GGGTCAGGAC        720

AGGTGCAGGG AGGGCTTCCT CATCTGCTCA CTGGTCTCCG TCCTCGCCAG CACCTCGCTG        780

TCACCAGGGC TCCTCTTTCT TTATTATCTG TGGTTCTGCT TCCTCACATT CTTGTGCCAG        840

GAAAGAAACG AGGAAGACGG GTTTTCGTCT ATAGTTGAAG CTTTTACTAG GATCTTGCCT        900

ACAAGTTCCT GCATGACCCA TTATAACTTA TCGATTAAAA AATATATATT CTAATGCTTC        960

TCACCATCTC TTGATTTGTA TCATCAACTG AATTGTACCC TCTTTGAAAT TCATATGATG       1020

AAACCTTAAA TTCAATGGAT CTATATTGGA ATTTTAATGA AATAATTAAG GTTAAATGTG       1080

```
GTCATAATTG TAAGACCCTA ATGCAATAGA CGTGTTGTCT TTATAAGAAG AGGAAGAGAC      1140

ACCAGAGACC TCTCACTTTT CACGTGCAGG CAGAGAAGAG GCCATGTGGA GACATAGTGC      1200

ACTAGAAGGT GG                                                          1212

(2) INFORMATION FOR SEQ ID NO:62:

(i) SEQUENCE CHARACTERISTICS:
         (A) LENGTH: 560 base pairs
         (B) TYPE: nucleic acid
         (C) STRANDEDNESS: double
         (D) TOPOLOGY: linear (ii) MOLECULE TYPE: Genomic DNA (vi) ORIGINAL SOURCE:
         (A) ORGANISM: Homo sapiens
         (G) CELL TYPE: human lymphoblast
         (H) CELL LINE: CGM1

(xi) SEQUENCE DESCRIPTION: SEQ ID NO:62:

GATCAGCACT GAACACAGAG GACTCACCAT GGAGTTTGGG CTGAGCTGGG TTTTCCTTGT        60

TGCTAATTTA AGAGGTGATT CATAGATAAA TAGAGATGTT GAGTGGGAGT GGACATGAGT       120

GAGAGAAACA GTGGATGTGT GTGGCAGTTT CTGACCTTGG TGTCTTTGTG TTTGCAGGTG       180

TCCAGTGTGA GGTGCAGCTG GTGGAGTCTG GGAAGGCTT GGTCCAGCCT GGGGGGTCCC       240

TGAGACTCTC CTGTGCAGCC TCTGGATTCA CCTTCAGTAG CTCTGCTATG CACTGGGTCC      300

GCCAGGCTCC AAGAAAGGGT TTGTAGTGGG TCTCAGTTAT TAGTACAAGT GGTGATACCG      360

TACTCTACAC AGACTCTGTG AAGGGCCGAT TCACCATCTC CAGAGACAAT GCCCAGAATT      420

CACTGTCTCT GCAAATGAAC AGCCTGAGAG CCGAGGGCAC AGTTGTGTAC TACTGTGTGA      480

AAGACGCAGT GAGAAGTCAG TGTGAGCCCA GACACAAACC TCCTGCAGGG TACCTGGGAC      540

AATCAGGGAA AGCCTGGGAC                                                  560

(2) INFORMATION FOR SEQ ID NO:63:

(i) SEQUENCE CHARACTERISTICS:
         (A) LENGTH: 515 base pairs
         (B) TYPE: nucleic acid
         (C) STRANDEDNESS: double
         (D) TOPOLOGY: linear (ii) MOLECULE TYPE: Genomic DNA (vi) ORIGINAL SOURCE:
         (A) ORGANISM: Homo sapiens
         (G) CELL TYPE: human lymphoblast
         (H) CELL LINE: CGM1

(xi) SEQUENCE DESCRIPTION: SEQ ID NO:63:

GAGCTCACTA TGGGGTTTGA GCTAACCAGA ATTTTTCTTG TTGCTATTTT AAAAGGTGAC        60

TCATAGAGAA ATAGAGTGAG TGAGAGTGAG TGGATATAAG TGAGAAAAAC AGTAGATGTG       120

TTTGGCAGTT TCTGACCAGG ACGTTTGTGT ATTTTCAGGT GTTCAGTGTG AGGTGGAGCT       180

GATAGAGTCC ATAGAGGGCC TGAGACAACT TGGGAAGTTC CTGAGACTCT CCTGTGTAGC      240

CTCTGGATTC ACCTTCAGTA GCTACTGAAT GAGCTGGGTC AATGAGACTC TAGGGAAGGG      300

GCTGGAGGGA GTAATAGATG TAAAATATGA TGGAAGTCAG ATATACCATG CAGACTCTGT      360

GAAGGGCAGA TTCACCATCT CCAAAGACAA TGCTAAGAAC TCACCGTATC TCCAAACGAA      420

CAGTCTGAGA GCTGAGGACA TGACCATGCA TGGCTGTACA TAAGGTTCCA AGTGAGGAAA      480
```

```
CATCGGTGTG AGTCCAGACC AAAATTTCCT GCAGG                              515

(2) INFORMATION FOR SEQ ID NO:64:

(i) SEQUENCE CHARACTERISTICS:
        (A) LENGTH: 649 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
         (A) ORGANISM: Homo sapiens
         (G) CELL TYPE: human lymphoblast
         (H) CELL LINE: CGM1

(xi) SEQUENCE DESCRIPTION: SEQ ID NO:64:

AGCTCTGGGA GAGGAGCCCC CCCCCTGGGA TTCCCAGGTG TTTTCATTTG GTGATCAGCA    60

CTGAACACAG AAGAGTCATG ACGGAGTTTG GGCTGAGCTG GGTTTTCCTT GTTGCTATTT   120

TTAAAGGTGA TTCATGAGGA AATAGAGATA TTGAGTGTGA GTGGACATGA GTGAGAGAAA   180

CAGTGGATTT GTGTGGCAGT TTCTGACCTT GGTGTCTCTG TGTTTGCAGG TGTCCAGTGT   240

GAGGTGCAGC TGGTGGAGTC TGGGGGAGGC TTGGTCCAGC CTGGGGGGTC CCTGAGACTC   300

TCCTGTGCAG CCTCTGGATT CACCTTCAGT AGCTATGCTA TGCACTGGGT CCGCCAGGCT   360

CCAGGGAAGG GACTGGAATA TGTTTCAGCT ATTAGTAGTA ATGGGGGTAG CACATATTAT   420

GCAAACTCTG TGAAGGGCAG ATTCACCATC TCCAGAGACA ATTCCAAGAA CACGCTGTAT   480

CTTCAAATGG GCAGCCTGAG AGCTGAGGAC ATGGCTGTGT ATTACTGTGC GAGAGACACA   540

GTGAGGAGAA GTTAATGTGG GACCATGCAG AAACCTCCCT GCGGGAACGC TGGGGAAAGT   600

CATCTGCAGG GGGCGCTCAG GAGCCACTGA TCAGCGTCAA CCGCAGCGG              649

(2) INFORMATION FOR SEQ ID NO:65:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:65:

AGGTGCAGCT GGTGCAGTCT G                                             21

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:66:

CCAGGGGCCT GTCGCACCCA                                               20

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: single
```

```
        (D) TOPOLOGY: linear (ii) MOLECULE TYPE: Genomic DNA (xi) SEQUENCE DESCRIPTION: SEQ ID NO:67:

TGGGGCCTCA GTGAAGGTCT CCTG                                              24

(2) INFORMATION FOR SEQ ID NO:68:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:68:

GATCCATCCC ATCCACTCAA G                                                 21

(2) INFORMATION FOR SEQ ID NO:69:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:69:

GATCCGTCCC ATCCACTCAA G                                                 21

(2) INFORMATION FOR SEQ ID NO:70:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:70:

TGTCTTCTCC ACAGGGGTCT T                                                 21

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:71:

GGGAAGGCCC TGGAGTGGCT                                                   20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA
```

(xi) SEQUENCE DESCRIPTION: SEQ ID NO:72:

GTGCAGGTCA GCGTGAGGGT                                          20

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:73:

TGGTTTTTGG AGGTGTCCTT GG                                       22

(2) INFORMATION FOR SEQ ID NO:74:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:74:

CACTCCAGCC CCTTCCCTGG AGC                                      23

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:75:

GTGAGGTTCA GCTGGTGGAG T                                        21

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:76:

AGCTGAACCT CACACTGGAC                                          20

(2) INFORMATION FOR SEQ ID NO:77:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:77:

AAGGGCCGAT TCACCATCT                                           19

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:78:

TTGTCTCTGG AGATGGTGAA                                      20

(2) INFORMATION FOR SEQ ID NO:79:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:79:

TGAGACTCTC CTGTGCAGCC TCTG                                24

(2) INFORMATION FOR SEQ ID NO:80:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:80:

TCTTTGTGTT TGCAGGTGT                                        19

(2) INFORMATION FOR SEQ ID NO:81:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:81:

TCTCTGTGTT TGCAGGTGT                                        19

(2) INFORMATION FOR SEQ ID NO:82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:82:

TCTGTTCACA GGGGTCCTGT C                                      21

(2) INFORMATION FOR SEQ ID NO:83:

(i) SEQUENCE CHARACTERISTICS:

(A) LENGTH: 19 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:83:

TCCGGCAGCC CCCAGGGAA                                                19

(2) INFORMATION FOR SEQ ID NO:84:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:84:

GCAGGTGAGG GACAGGGT                                                 18

(2) INFORMATION FOR SEQ ID NO:85:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:85:

CAGGGAGAAC TGGTTCTTGG A                                             21

(2) INFORMATION FOR SEQ ID NO:86:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:86:

CCCGGGCATC TGGCGCACCC A                                             21

(2) INFORMATION FOR SEQ ID NO:87:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:87:

GCTGCTCCAC TGCAGGTAGG C                                             21

(2) INFORMATION FOR SEQ ID NO:88:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:88:

CTTCAGGCTG CTCCACTGCA G                                                     21

(2) INFORMATION FOR SEQ ID NO:89:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:89:

Met Ser Val Ser Phe Leu Ile Phe Leu Pro Val Leu Gly Leu Pro Trp
 1               5                  10                  15

Gly Val Leu Ser Gln Val Gln Leu Gln Gln Ser Gly Pro Gly Leu Val
                20                  25                  30

Lys Pro Ser Gln Thr Leu Ser Leu Thr Cys Ala Ile Ser Gly Asp Ser
            35                  40                  45

Val Ser Ser Asn Ser Ala Ala Trp Asn Trp Ile Arg Gln Ser Pro Ser
        50                  55                  60

Arg Gly Leu Glu Trp Leu Gly Arg Thr Tyr Tyr Arg Ser Lys Trp Tyr
 65                  70                  75                  80

Asn Asp Tyr Ala Val Ser Val Lys Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg
        115                 120

(2) INFORMATION FOR SEQ ID NO:90:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:90:

Met Asp Trp Thr Trp Arg Ile Leu Phe Leu Val Ala Ala Ala Thr Gly
 1               5                  10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asn Ser Gly Gly Thr Asn Tyr Ala
 65                  70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg
        115

(2) INFORMATION FOR SEQ ID NO:91:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:91:

Met Asp Trp Thr Trp Arg Ile Leu Phe Leu Val Ala Ala Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Ala Met His Trp Val Arg Gln Ala Pro Gly Gln Arg Leu
    50                  55                  60

Glu Trp Met Gly Trp Ser Asn Ala Gly Asn Gly Asn Thr Lys Tyr Ser
65                  70                  75                  80

Gln Glu Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Met Ala Val
            100                 105                 110

Tyr Tyr Cys Ala Arg
        115

(2) INFORMATION FOR SEQ ID NO:92:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:92:

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Tyr Tyr Trp Ser Trp Ile Arg Gln Pro Ala Gly Lys Gly Leu
    50                  55                  60

Glu Trp Ile Gly Arg Ile Tyr Thr Ser Gly Ser Thr Asn Tyr Asn Pro
65                  70                  75                  80

Ser Leu Lys Ser Arg Val Thr Met Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg
    115

(2) INFORMATION FOR SEQ ID NO:93:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:93:

Met Asp Thr Leu Cys Ser Thr Leu Leu Leu Thr Ile Pro Ser Trp
1               5                   10                  15

Val Leu Ser Gln Ile Thr Leu Lys Glu Ser Gly Pro Thr Leu Val Lys
                20                  25                  30

Pro Thr Gln Thr Leu Thr Leu Thr Cys Thr Phe Ser Gly Phe Ser Leu
            35                  40                  45

Ser Thr Ser Gly Val Gly Val Gly Trp Ile Arg Gln Pro Pro Gly Lys
    50                  55                  60

Ala Leu Glu Trp Leu Ala Leu Ile Tyr Trp Asn Asp Asp Lys Arg Tyr
65                  70                  75                  80

Ser Pro Ser Leu Lys Ser Arg Leu Thr Ile Thr Lys Asp Thr Ser Lys
                85                  90                  95

Asn Gln Val Val Leu Thr Met Thr Asn Met Asp Pro Val Asp Thr Ala
                100                 105                 110

Thr Tyr Tyr Cys Ala His Arg
            115

(2) INFORMATION FOR SEQ ID NO:94:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:94:

Met Glu Leu Gly Leu Arg Trp Val Phe Leu Ala Ala Ile Leu Lys Gly
1               5                   10                  15

Val Gln Cys Glu Met Gln Leu Val Glu Ser Gly Ala Asn Leu Thr Lys
                20                  25                  30

Pro Gly Cys Pro Asp Ser Pro Val Gln Pro Leu Asp Ser Pro Ser Val
            35                  40                  45

Ala Ile Ala Arg Thr Gly Ser Pro Arg Leu Gln Gly Arg Val Cys Ser
    50                  55                  60

Gly Ser Gln Leu Leu Val Val Val Val Pro Cys Thr Thr Gln Thr
65                  70                  75                  80

Leu Arg Ala Asp Ser Pro Phe Pro Glu Thr Ile Pro Lys Thr His Cys
                85                  90                  95

Ile Cys Lys Thr Asp Gly Gln Arg Met Gln Leu His Met Thr Leu Glu
                100                 105                 110

(2) INFORMATION FOR SEQ ID NO:95:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:95:

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
                20                  25                  30

```
Pro Gly Gly Ser Leu Arg Leu Ser Cys Ala Ala Ser Gly Phe Thr Phe
        35                  40                  45

Ser Ser Tyr Trp Met Ser Trp Val Arg Gln Ala Pro Gly Lys Gly Leu
 50                  55                  60

Glu Trp Val Ala Asn Ile Lys Gln Asp Gly Ser Glu Lys Tyr Tyr Val
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg
            115
```

(2) INFORMATION FOR SEQ ID NO:96:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:96:

```
Met Asp Trp Thr Trp Arg Ile Leu Phe Leu Val Ala Ala Ala Thr Ser
 1                   5                  10                  15

Ala His Ser Gln Val Gln Leu Val Gln Ser Gly Ala Glu Val Lys Lys
                 20                  25                  30

Pro Gly Ala Ser Val Lys Val Ser Cys Lys Ala Ser Gly Tyr Thr Phe
            35                  40                  45

Thr Ser Tyr Asp Ile Asn Trp Val Arg Gln Ala Thr Gly Gln Gly Leu
 50                  55                  60

Glu Trp Met Gly Trp Met Asn Pro Asn Ser Gly Asn Thr Gly Tyr Ala
 65                  70                  75                  80

Gln Lys Phe Gln Gly Arg Val Thr Met Thr Arg Asn Thr Ser Ile Ser
                 85                  90                  95

Thr Ala Tyr Met Glu Leu Ser Ser Leu Arg Ser Glu Asp Thr Ala Val
            100                 105                 110

Tyr Tyr Cys Ala Arg
            115
```

(2) INFORMATION FOR SEQ ID NO:97:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:97:

```
Met Glu Leu Gly Leu Ser Trp Ile Phe Leu Leu Ala Ile Leu Lys Gly
 1                   5                  10                  15

Val Gln Cys Glu Val Gln Leu Val Glu Ser Gly Gly Gly Leu Val Gln
                 20                  25                  30

Pro Gly Arg Ser Leu Arg Leu Ser Cys Ala Ala Ser Gly Phe Thr Phe
            35                  40                  45

Asp Asp Tyr Ala Met His Trp Val Arg Gln Ala Pro Gly Lys Gly Leu
 50                  55                  60
```

```
Glu Trp Val Ser Gly Ile Ser Trp Asn Ser Gly Ser Ile Gly Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Leu
            100                 105                 110

Tyr Tyr Cys Ala Lys Asp
            115
```

(2) INFORMATION FOR SEQ ID NO:98:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:98:

```
Met Glu Leu Tyr Ser Thr Leu Leu Leu Thr Val Pro Ser Trp Val
 1               5                  10                  15

Leu Ser Gln Val Thr Leu Lys Glu Ser Gly Pro Ala Leu Val Lys Pro
                 20                  25                  30

Thr Gln Thr Leu Met Leu Thr Cys Thr Phe Ser Gly Phe Ser Leu Ser
            35                  40                  45

Thr Ser Gly Met Gly Val Gly Ile Cys Gln Pro Ser Ala Lys Ala Leu
 50                  55                  60

Glu Trp Leu Ala His Ile Tyr Asn Asp Asn Lys Tyr Tyr Ser Pro Ser
 65                  70                  75                  80

Leu Lys Ser Arg Leu Ile Ile Ser Lys Asp Thr Ser Lys Asn Glu Val
                 85                  90                  95

Val Leu Thr Val Ile Asn Met Asp Ile Val Asp Thr Ala Thr His
            100                 105                 110
```

(2) INFORMATION FOR SEQ ID NO:99:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:99:

```
Met Glu Phe Gly Leu Ser Trp Val Phe Leu Val Ala Ile Ile Lys Gly
 1               5                  10                  15

Val Gln Cys Gln Val Gln Leu Val Glu Ser Gly Gly Gly Leu Val Lys
                 20                  25                  30

Pro Gly Gly Ser Leu Arg Leu Ser Cys Ala Ala Ser Gly Phe Thr Phe
            35                  40                  45

Ser Asp Tyr Tyr Met Ser Trp Ile Arg Gln Ala Pro Gly Lys Gly Leu
 50                  55                  60

Glu Trp Val Ser Tyr Ile Ser Ser Ser Gly Ser Thr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg
```

115

(2) INFORMATION FOR SEQ ID NO:100:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:100:

```
Met Xaa Trp Thr Tyr Lys Ile Leu Phe Leu Val Ala Ala Thr Gly
 1               5                  10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Tyr Cys Tyr Leu His Trp Val Gln Ala Pro Gly Gln Gly Leu Glu
 50                  55                  60

Trp Thr Gly Phe Leu Phe Glu Arg Phe Phe Ile Gln His Leu Phe Cys
 65                  70                  75                  80

Lys Gln Ile Ser Gly Ile Val Glu Ile Ile Leu Thr Asn Leu Thr Gln
                85                  90                  95

Asn Phe Leu Ile Asn Leu Cys Lys His Gln Phe Leu Asn Gln Cys Cys
                100                 105                 110

Xaa Tyr Phe Arg Thr Gln Ala Gln Xaa His Ile Xaa Thr Leu Leu Xaa
            115                 120                 125

Ser Leu Phe Lys Xaa Tyr Gln Lys Xaa Ser Ser Xaa Ala Cys Asn Val
 130                 135                 140
```

(2) INFORMATION FOR SEQ ID NO:101:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:101:

```
Met Glu Leu Gly Leu Ser Trp Val Phe Leu Val Ala Ile Leu Glu Gly
 1               5                  10                  15

Val Gln Cys Glu Val His Leu Val Glu Ser Gly Gly Gly Leu Val Gln
            20                  25                  30

Pro Gly Gly Ala Leu Arg Leu Ser Cys Ala Ala Ser Gly Phe Thr Phe
            35                  40                  45

Ser Asn Tyr Asp Met His Trp Val Arg Gln Ala Thr Gly Lys Gly Leu
 50                  55                  60

Glu Trp Val Ser Ala Asn Gly Thr Ala Gly Asp Thr Tyr Tyr Pro Gly
 65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
                100                 105                 110

Tyr Cys Ala Arg
            115
```

(2) INFORMATION FOR SEQ ID NO:102:

(i) SEQUENCE CHARACTERISTICS:
    (A) LENGTH: 119 amino acids
    (B) TYPE: amino acid
    (D) TOPOLOGY: linear (ii) MOLECULE TYPE: protein (xi) SEQUENCE DESCRIPTION: SEQ ID NO:102:

Met Glu Phe Gly Leu Ser Trp Ile Phe Leu Pro Ala Ile Leu Lys Gly
 1               5                  10                  15

Val Gln Cys Glu Val Gln Leu Val Glu Ser Gly Gly Ala Leu Val Lys
            20                  25                  30

Pro Gly Gly Ser Leu Arg Leu Ser Cys Ala Ala Ser Gly Phe Thr Phe
        35                  40                  45

Ser Asn Ala Trp Met Ser Trp Val Arg Gln Ala Pro Gly Lys Gly Leu
    50                  55                  60

Glu Trp Val Gly Arg Ile Lys Ser Lys Thr Asp Gly Gly Thr Thr Asp
65                  70                  75                  80

Tyr Ala Ala Pro Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Val Tyr Tyr Cys Thr Thr
        115

(2) INFORMATION FOR SEQ ID NO:103:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:103:

Met Glu Phe Gly Leu Ser Trp Val Phe Leu Ala Gly Ile Leu Lys Gly
 1               5                  10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Ser Asp Met Asn Trp Ala Arg Lys Ala Pro Gly Lys Gly Leu
    50                  55                  60

Glu Trp Val Ser Gly Val Ser Trp Asn Gly Ser Arg Thr His Tyr Val
65                  70                  75                  80

Asp Ser Val Lys Arg Arg Phe Ile Ile Ser Arg Asp Asn Ser Arg Asn
                85                  90                  95

Ser Leu Tyr Leu Gln Lys Asn Arg Arg Ala Glu Asp Met Ala Val
            100                 105                 110

Tyr Tyr Cys Val Arg
        115

(2) INFORMATION FOR SEQ ID NO:104:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:104:

Met Asp Cys Thr Trp Gly Ile Leu Phe Leu Val Ala Ser Xaa Thr Asp
1               5                   10                  15

Val His Ser Gln Val Gln Leu Leu Gln Pro Gly Ala Glu Val Lys Lys
                20                  25                  30

Pro Ala Ser Ser Val Lys Val Ser Trp Pro Gly Phe Gln Ile His Leu
            35                  40                  45

His Gln Ile Leu Tyr Thr Val Gly Ala Thr Gly Pro Trp Thr Arg Ala
        50                  55                  60

Trp Leu Gly Cys Ile Asn Pro Tyr Asn Asp Asn Thr His Tyr Ala Gln
65                  70                  75                  80

Lys Phe Arg Gly Arg Val Thr Ile Thr Ser Asp Arg Ser Val Ser Thr
                85                  90                  95

Ala Tyr Met Glu Leu Ser Ser Leu Arg Ser Glu Asp Met Val Val Tyr
            100                 105                 110

Ser Cys Val Arg
        115

(2) INFORMATION FOR SEQ ID NO:105:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:105:

Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Gly Ile Ser Trp Val Arg Gln Ala Pro Gly Gln Gly Leu
        50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg
        115

(2) INFORMATION FOR SEQ ID NO:106:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:106:

Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Val Val Arg

```
                    20                  25                  30

Pro Gly Gly Ser Leu Arg Leu Ser Cys Ala Ala Ser Gly Phe Thr Phe
            35                  40                  45

Asp Asp Tyr Gly Met Ser Trp Val Arg Gln Ala Pro Gly Lys Gly Leu
 50                  55                  60

Glu Trp Val Ser Gly Ile Asn Trp Asn Gly Ser Thr Gly Tyr Ala
 65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr His Cys Ala Arg
            115

(2) INFORMATION FOR SEQ ID NO:107:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:107:

Met Glu Leu Gly Leu Arg Trp Val Phe Leu Val Ala Ile Leu Glu Gly
 1               5                  10                  15

Val Gln Cys Glu Val Gln Leu Val Glu Ser Gly Gly Gly Leu Val Lys
                20                  25                  30

Pro Gly Gly Ser Leu Arg Leu Ser Cys Ala Ala Ser Gly Phe Thr Phe
            35                  40                  45

Ser Ser Tyr Ser Met Asn Trp Val Arg Gln Ala Pro Gly Lys Gly Leu
 50                  55                  60

Glu Trp Val Ser Ser Ile Ser Ser Ser Ser Tyr Ile Tyr Tyr Ala
 65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg
            115

(2) INFORMATION FOR SEQ ID NO:108:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:108:

Met Glu Ser Trp Leu Ser Trp Val Phe Leu Ala Ala Ile Leu Lys Gly
 1               5                  10                  15

Val Gln Cys Glu Val His Leu Val Glu Ser Gly Gly Ala Leu Val Gln
                20                  25                  30

Pro Gly Gly Ser Leu Arg Leu Ser Cys Ala Ala Ser Gly Phe Thr Phe
            35                  40                  45

Ser Tyr Tyr Tyr Met Ser Gly Val Arg Gln Ala Pro Gly Lys Gly Leu
 50                  55                  60
```

```
Glu Trp Val Gly Phe Ile Arg Asn Lys Ala Asn Gly Gly Thr Thr Glu
 65                  70                  75                  80

Thr Thr Ser Val Lys Gly Arg Phe Thr Ile Ser Arg Asp Asp Ser Lys
                 85                  90                  95

Ser Ile Thr Tyr Leu Gln Met Lys Ser Leu Lys Thr Glu Asp Thr Ala
             100                 105                 110

Val Tyr Tyr Cys Ser Arg
            115
```

(2) INFORMATION FOR SEQ ID NO:109:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:109:

```
Met Glu Phe Gly Leu Ser Trp Leu Phe Leu Val Ala Lys Ile Lys Gly
 1               5                  10                  15

Val Gln Cys Glu Val Gln Leu Leu Glu Ser Gly Gly Gly Leu Val Gln
                 20                  25                  30

Pro Gly Gly Ser Leu Arg Leu Ser Cys Ala Ala Ser Gly Phe Thr Phe
             35                  40                  45

Ser Ser Tyr Ala Met Ser Trp Val Arg Gln Ala Pro Gly Lys Gly Leu
         50                  55                  60

Glu Trp Val Ser Ala Ile Ser Gly Ser Gly Gly Ser Thr Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Tyr Cys Ala Lys
            115
```

(2) INFORMATION FOR SEQ ID NO:110:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:110:

```
Met Asp Cys Thr Trp Arg Ile Leu Phe Leu Val Ala Ala Ala Thr Gly
 1               5                  10                  15

Thr His Ala Gln Val Gln Leu Val Gln Ser Gly Ala Glu Val Lys Lys
                 20                  25                  30

Pro Gly Ala Ser Val Lys Val Ser Cys Lys Val Ser Gly Tyr Thr Leu
             35                  40                  45

Thr Glu Leu Ser Met His Trp Val Arg Gln Ala Pro Gly Lys Gly Leu
         50                  55                  60

Glu Trp Met Gly Gly Phe Asp Pro Glu Asp Gly Glu Thr Ile Tyr Ala
 65                  70                  75                  80

Gln Lys Phe Gln Gly Arg Val Thr Met Thr Glu Asp Thr Ser Thr Asp
                 85                  90                  95
```

```
Thr Ala Tyr Met Glu Leu Ser Ser Leu Arg Ser Glu Asp Thr Ala Val
            100                 105                 110

Tyr Tyr Cys Ala Thr
            115

(2) INFORMATION FOR SEQ ID NO:111:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:111:

Trp Ser Leu Cys Ala Gly Phe Ser Leu Leu Phe Asn Val Ser Ser
 1               5                  10                  15

Val Arg Cys Ser Trp Trp Ser Leu Gly Glu Ala Cys Lys Ser Leu Arg
            20                  25                  30

Gly Pro Arg Asp Ser Pro Val Gln Pro Leu Asn Ser Pro Ser Val Ala
            35                  40                  45

Thr Thr Thr Val Ser Ala Arg Leu Gln Gly Met Gly Trp Ser Trp Phe
 50                  55                  60

Asp Lys Leu Ile Leu Met Gly Val Ala His Thr Ser Thr Pro Val Arg
 65                  70                  75                  80

Thr Asp Ser Ile Pro Pro Glu Ile Thr Pro Arg Thr His Phe Ile Cys
            85                  90                  95

Lys Thr Ala Lys Pro Arg Thr Arg Pro Ser Ile Ser Val Pro Glu
            100                 105                 110

(2) INFORMATION FOR SEQ ID NO:112:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:112:

Met Asp Thr Leu Cys Tyr Thr Leu Leu Leu Thr Thr Pro Ser Trp
 1               5                  10                  15

Val Leu Ser Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
            35                  40                  45

Ser Asn Ala Arg Met Gly Val Ser Trp Ile Arg Gln Pro Pro Gly Lys
 50                  55                  60

Ala Leu Glu Trp Leu Ala His Ile Phe Ser Asn Asp Glu Lys Ser Tyr
 65                  70                  75                  80

Ser Thr Ser Leu Lys Ser Arg Leu Thr Ile Ser Lys Asp Thr Ser Lys
            85                  90                  95

Ser Gln Val Val Leu Thr Met Thr Asn Met Asp Pro Val Asp Thr Ala
            100                 105                 110

Thr Tyr Tyr Cys Ala Arg Ile
            115

(2) INFORMATION FOR SEQ ID NO:113:

(i) SEQUENCE CHARACTERISTICS:
```

(A) LENGTH: 112 amino acids
(B) TYPE: amino acid
(D) TOPOLOGY: linear (ii) MOLECULE TYPE: protein (xi) SEQUENCE DESCRIPTION: SEQ ID NO:113:

Met Tyr Trp Thr Trp Arg Ile Leu Phe Leu Val Ala Ala Ala Thr Gly
1               5                   10                  15

Val His Ser Gln Val Gln Leu Val Gln Ser Gly Pro Glu Val Lys Lys
                20                  25                  30

Pro Gly Ala Ser Leu Lys Val Ser Cys Lys Ala Ser Gly Tyr Thr Phe
            35                  40                  45

Thr Ser Tyr Ala Ile Ser Trp Val Gln Ala His Gly Gln Gly Leu Glu
        50                  55                  60

Glu Met Gly Trp Ile Asn Thr Asn Thr Gly Asn Leu Thr Tyr Ala Gln
65                  70                  75                  80

Gly Phe Thr Gly Arg Phe Val Phe Ser Met Asp Thr Ser Val Ser Met
                85                  90                  95

Ala Tyr Leu His Ile Ser Ser Leu Lys Ala Glu Asp Thr Cys Lys Arg
            100                 105                 110

(2) INFORMATION FOR SEQ ID NO:114:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:114:

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
                20                  25                  30

Pro Ser Asp Thr Leu Ser Leu Thr Cys Ala Val Ser Gly Tyr Ser Ile
            35                  40                  45

Ser Ser Ser Asn Trp Trp Gly Trp Ile Arg Gln Pro Pro Gly Lys Gly
        50                  55                  60

Leu Glu Trp Ile Gly Tyr Ile Tyr Tyr Ser Gly Ser Thr Tyr Tyr Asn
65                  70                  75                  80

Pro Ser Leu Lys Ser Arg Val Thr Met Ser Val Asp Thr Ser Lys Asn
                85                  90                  95

Gln Phe Ser Leu Lys Leu Ser Ser Val Thr Ala Val Asp Thr Ala Val
            100                 105                 110

Tyr Tyr Cys Ala Arg
        115

(2) INFORMATION FOR SEQ ID NO:115:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:115:

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Asp Thr Ala Val
            100                 105                 110

Tyr Tyr Cys Ala Arg
        115

(2) INFORMATION FOR SEQ ID NO:116:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:116:

Met Lys His Leu Trp Phe Phe Leu Leu Leu Val Ala Ala Pro Arg Trp
1               5                   10                  15

Val Leu Pro Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Ser Gly Gly Tyr Tyr Trp Ser Trp Ile Arg Gln His Pro Gly Lys
    50                  55                  60

Gly Leu Glu Trp Ile Gly Tyr Ile Tyr Tyr Ser Gly Ser Thr Tyr Tyr
65                  70                  75                  80

Asn Pro Ser Leu Lys Ser Arg Val Thr Ile Ser Val Asp Thr Ser Lys
            85                  90                  95

Asn Gln Phe Ser Leu Lys Leu Ser Ser Val Thr Ala Ala Asp Thr Ala
            100                 105                 110

Val Tyr Tyr Cys Ala Arg
        115

(2) INFORMATION FOR SEQ ID NO:117:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:117:

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

```
Ser Ser Tyr Gly Met His Trp Val Arg Gln Ala Pro Gly Lys Gly Leu
        50                  55                  60

Glu Trp Val Ala Val Ile Trp Tyr Asp Gly Ser Asn Lys Tyr Tyr Ala
 65                  70                  75                  80

Asp Ser Ala Lys Gly Arg Phe Thr Ile Ser Arg Asp Asn Ser Thr Asn
                85                  90                  95

Thr Leu Phe Leu Gln Met Asn Ser Leu Arg Ala Glu Asp Thr Ala Val
            100                 105                 110

Tyr Tyr Cys Ala Arg
        115

(2) INFORMATION FOR SEQ ID NO:118:

(i) SEQUENCE CHARACTERISTICS:
         (A) LENGTH: 116 amino acids
         (B) TYPE: amino acid
         (D) TOPOLOGY: linear (ii) MOLECULE TYPE: protein (xi) SEQUENCE DESCRIPTION: SEQ ID NO:118:

Met Lys His Leu Trp Phe Phe Leu Leu Leu Val Ala Ala Pro Arg Trp
 1               5                  10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Ser Trp Ile Arg Gln Pro Pro Gly Lys Gly Leu
        50                  55                  60

Glu Trp Ile Gly Glu Ile Asn His Ser Gly Ser Thr Asn Tyr Asn Pro
 65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg
        115

(2) INFORMATION FOR SEQ ID NO:119:

(i) SEQUENCE CHARACTERISTICS:
         (A) LENGTH: 117 amino acids
         (B) TYPE: amino acid
         (D) TOPOLOGY: linear (ii) MOLECULE TYPE: protein (xi) SEQUENCE DESCRIPTION: SEQ ID NO:119:

Met Glu Phe Gly Leu Ser Trp Val Phe Leu Ala Ala Ile Leu Lys Gly
 1               5                  10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asn Ser Asp Met Asn Trp Val His Gln Ala Pro Gly Lys Gly Leu
        50                  55                  60

Glu Trp Val Ser Gly Val Ser Trp Asn Gly Ser Arg Thr His Tyr Ala
 65                  70                  75                  80

Asp Ser Val Lys Gly Arg Phe Ile Ile Ser Arg Asp Asn Ser Arg Asn
```

```
                       85                  90                  95
Thr Leu Tyr Leu Gln Thr Asn Ser Leu Arg Ala Glu Asp Thr Ala Val
            100                 105                 110
Tyr Tyr Cys Val Arg
        115
```

(2) INFORMATION FOR SEQ ID NO:120:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:120:

```
Met Glu Phe Gly Leu Ser Trp Gly Phe His Val Ala Asn Val Lys Gly
 1               5                  10                  15
Val Gln Cys Glu Val His Leu Val Glu Ser Leu Gly Gly Leu Leu Pro
            20                  25                  30
Gly Gly Pro Asp Phe Leu Leu Gln Pro Leu Asp Ser Pro Leu Val Pro
        35                  40                  45
Leu Leu Gly Thr Gly Ala Gly Ser Ile Arg Leu Leu Gly Lys Gly Trp
    50                  55                  60
Ser Arg Ser His Leu Val Val Val Ala Gln Ala Met Gln Thr Leu
65                  70                  75                  80
Arg Val Asp Ser Pro Ser Pro Glu Met Met Pro Arg Asn His Cys Ile
                85                  90                  95
Cys Lys Thr Ala Ser Glu Pro Arg Ile Gly Leu Cys Ile Thr Val Val
            100                 105                 110
```

(2) INFORMATION FOR SEQ ID NO:121:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:121:

```
Met Leu Phe Gly Leu Ser Trp Pro Phe Arg Phe Thr Ile Leu Arg Gly
 1               5                  10                  15
Val Gln Tyr Glu Val Gln Leu Val Glu Ser Gly Gly Asp Leu Val Gln
            20                  25                  30
Leu Trp Trp Val Leu Arg Leu Ser Cys Ala Ala Cys Gly Phe Ile Leu
        35                  40                  45
Arg Ser Asn Trp Ser His Arg Ala Ser Arg Lys Gly Leu Ala Trp Asn
    50                  55                  60
Asp Met Val Ser Tyr Ile Ser Ala Ser Gly Gly Ser Leu Tyr Tyr Ala
65                  70                  75                  80
Asp Thr Glu Gly Ile His His Leu Arg Gln Trp Gln Glu His Ala Val
                85                  90                  95
Leu Ala Asn Glu Gln Ser Glu Arg Gly Leu Gly Cys Val Glu Arg
            100                 105                 110
```

(2) INFORMATION FOR SEQ ID NO:122:

(i) SEQUENCE CHARACTERISTICS:
        (A) LENGTH: 115 amino acids (B) TYPE: amino acid
            (D) TOPOLOGY: linear (ii) MOLECULE TYPE: protein (xi) SEQUENCE DESCRIPTION: SEQ ID NO:122:

Met Gln Phe Val Leu Ser Trp Val Phe Leu Val Gly Ile Leu Lys Gly
 1               5                  10                  15

Val Gln Cys Glu Val Gln Leu Val Glu Ser Gly Gly Gly Leu Val Gln
             20                  25                  30

Pro Arg Gly Ser Leu Arg Leu Ser Cys Ala Ala Ser Gly Phe Thr Val
         35                  40                  45

Ser Ser Asn Glu Met Ser Trp Ile Arg Gln Ala Pro Gly Lys Gly Leu
     50                  55                  60

Glu Trp Val Ser Ser Ile Ser Gly Gly Ser Thr Tyr Tyr Ala Asp Ser
 65                  70                  75                  80

Arg Lys Gly Arg Phe Thr Ile Ser Arg Asp Asn Ser Lys Asn Thr Leu
                 85                  90                  95

Tyr Leu Gln Met Asn Asn Leu Arg Ala Glu Gly Thr Ala Ala Tyr Tyr
             100                 105                 110

Cys Ala Arg
         115

(2) INFORMATION FOR SEQ ID NO:123:

(i) SEQUENCE CHARACTERISTICS:
            (A) LENGTH: 118 amino acids
            (B) TYPE: amino acid
            (D) TOPOLOGY: linear (ii) MOLECULE TYPE: protein (xi) SEQUENCE DESCRIPTION: SEQ ID NO:123:

Met Lys His Leu Trp Phe Phe Leu Leu Leu Val Ala Ala Pro Arg Trp
 1               5                  10                  15

Val Leu Ser Gln Leu Gln Leu Gln Glu Ser Gly Pro Gly Leu Val Lys
             20                  25                  30

Pro Ser Glu Thr Leu Ser Leu Thr Cys Thr Val Ser Gly Gly Ser Ile
         35                  40                  45

Ser Ser Ser Ser Tyr Tyr Trp Gly Trp Ile Arg Gln Pro Pro Gly Lys
     50                  55                  60

Gly Leu Glu Trp Ile Gly Ser Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
             100                 105                 110

Val Tyr Tyr Cys Ala Arg
         115

(2) INFORMATION FOR SEQ ID NO:124:

(i) SEQUENCE CHARACTERISTICS:
            (A) LENGTH: 114 amino acids
            (B) TYPE: amino acid
            (D) TOPOLOGY: linear (ii) MOLECULE TYPE: protein (xi) SEQUENCE DESCRIPTION: SEQ ID NO:124:

```
Met Glu Ser Trp Leu Ser Trp Val Phe Leu Ala Ala Ile Leu Lys Gly
  1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Phe Ser Phe
         35                  40                  45

Ser Ser Tyr Gly Met Ser Trp Val Arg Gln Ala Pro Gly Lys Gly Leu
     50                  55                  60

Glu Val Ala His Ile Trp Asn Asp Gly Ser Gln Lys Tyr Tyr Ala Asp
 65                  70                  75                  80

Ser Val Lys Gly Arg Phe Thr Ile Ser Glu Thr Ile Leu Arg Ala Cys
                 85                  90                  95

Ser Ile Cys Lys Trp Thr Val Lys Leu Arg Thr Arg Pro Cys Ile Thr
                100                 105                 110

Val Pro
```

(2) INFORMATION FOR SEQ ID NO:125:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:125:

```
Met Glu Phe Gly Leu Ser Trp Val Phe Leu Val Ala Ile Leu Lys Gly
  1               5                  10                  15

Val Gln Cys Glu Val Gln Leu Val Glu Ser Gly Gly Val Val Val Gln
             20                  25                  30

Pro Gly Gly Ser Leu Arg Leu Ser Cys Ala Ala Ser Gly Phe Thr Phe
         35                  40                  45

Asp Asp Tyr Thr Met His Trp Val Arg Gln Ala Pro Gly Lys Gly Leu
     50                  55                  60

Glu Trp Val Ser Leu Ile Ser Trp Asp Gly Gly Ser Thr Tyr Tyr Ala
 65                  70                  75                  80

Asp Ser Val Lys Gly Arg Phe Thr Ile Ser Arg Asp Asn Ser Lys Asn
                 85                  90                  95

Ser Leu Tyr Leu Gln Met Asn Ser Leu Arg Thr Glu Asp Thr Ala Leu
                100                 105                 110

Tyr Tyr Cys Ala Lys Asp
                115
```

(2) INFORMATION FOR SEQ ID NO:126:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:126:

```
Met Leu Phe Gly Leu Ser Trp Ala Phe Leu Val Thr Ile Leu Arg Gly
  1               5                  10                  15

Val Gln Tyr Glu Val Gln Leu Val Glu Ser Phe Phe Phe Phe Phe Phe
             20                  25                  30

His Phe Leu Ala Asn Ile His Gly Leu Gln Asn Asn Gly Leu Ala Phe
         35                  40                  45
```

```
Leu Pro Thr Leu Tyr Arg His His Gln Phe Ser Pro Cys Leu Gly Phe
    50                  55                  60

Pro Glu Glu Cys Cys His His Leu Ser Cys Ser Phe Arg Lys Asn Ala
65                  70                  75                  80

Pro Ser Thr His Leu His Leu Ser Ala Cys Ile Ser Ile Cys Leu Gly
                85                  90                  95

Arg Ser Gln Gln Pro Xaa Glu His Ser Pro His Pro Thr Met Leu Leu
            100                 105                 110

Glu Gly Val
        115

(2) INFORMATION FOR SEQ ID NO:127:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:127:

Met Asp Trp Thr Trp Arg Ile Leu Phe Leu Val Ala Ala Thr Asp
1               5                   10                  15

Ala Tyr Ser Gln Met Gln Leu Val Gln Ser Gly Ala Glu Val Lys Lys
                20                  25                  30

Thr Gly Ser Ser Val Lys Val Ser Cys Lys Ala Ser Gly Tyr Thr Phe
                35                  40                  45

Thr Tyr Arg Tyr Leu His Trp Val Arg Gln Ala Pro Gly Gln Ala Leu
            50                  55                  60

Glu Trp Met Gly Trp Ile Thr Pro Phe Asn Gly Asn Thr Asn Tyr Ala
65                  70                  75                  80

Gln Lys Phe Gln Asp Arg Val Thr Ile Thr Arg Asp Arg Ser Met Ser
                85                  90                  95

Thr Ala Tyr Met Glu Leu Ser Ser Leu Arg Ser Glu Asp Thr Ala Met
            100                 105                 110

Tyr Tyr Cys Ala Arg
        115

(2) INFORMATION FOR SEQ ID NO:128:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:128:

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Ser Tyr Tyr Met His Trp Val Arg Gln Ala Pro Gly Gln Gly Leu
            50                  55                  60

Glu Trp Met Gly Ile Ile Asn Pro Ser Gly Gly Ser Thr Ser Tyr Ala
65                  70                  75                  80
```

Gln Lys Phe Gln Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg
        115

(2) INFORMATION FOR SEQ ID NO:129:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:129:

Arg Glu Phe Val Leu Ser Trp Val Phe Leu Val Ala Ile Leu Lys Cys
1               5                   10                  15

Val Gln Cys Glu Asp Gln Leu Val Glu Ser Gly Gly Gly Leu Val Gln
                20                  25                  30

Pro Gly Gly Ser Leu Arg Pro Ser Cys Ala Ala Ser Gly Phe Ala Phe
            35                  40                  45

Ser Ser Tyr Val Leu His Trp Val Arg Arg Ala Pro Gly Lys Gly Pro
50                  55                  60

Glu Trp Val Ser Ala Ile Gly Thr Gly Gly Asp Thr Tyr Tyr Ala Asp
65                  70                  75                  80

Ser Val Met Gly Arg Phe Thr Ile Ser Arg Asp Asn Ala Lys Lys Ser
                85                  90                  95

Leu Tyr Leu Lys Thr Ala Leu Arg Thr Trp Leu Cys Ile Met
            100                 105                 110

2) INFORMATION FOR SEQ ID NO:130:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:130:

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Ser Met Asn Trp Val Arg Gln Ala Pro Gly Lys Gly Leu
50                  55                  60

Glu Trp Val Ser Tyr Ile Ser Ser Ser Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg
        115

(2) INFORMATION FOR SEQ ID NO:131:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO:131:

```
Met Glu Phe Gly Leu Ser Trp Val Phe Leu Val Ala Ile Leu Lys Gly
 1               5                  10                  15

Val Gln Cys Glu Val Gln Leu Val Glu Ser Gly Gly Gly Leu Val Gln
            20                  25                  30

Pro Gly Arg Ser Leu Arg Leu Ser Cys Thr Ala Ser Gly Phe Thr Phe
        35                  40                  45

Gly Asp Tyr Ala Met Ser Trp Phe Arg Gln Ala Pro Gly Lys Gly Leu
    50                  55                  60

Glu Trp Val Gly Phe Ile Arg Ser Lys Ala Tyr Gly Gly Thr Thr Glu
65                  70                  75                  80

Tyr Thr Ala Ser Val Lys Gly Arg Phe Thr Ile Ser Arg Asp Gly Ser
                85                  90                  95

Lys Ser Ile Ala Tyr Leu Gln Met Asn Ser Leu Lys Thr Glu Asp Thr
            100                 105                 110

Ala Val Tyr Tyr Cys Thr Arg
        115
```

(2) INFORMATION FOR SEQ ID NO:132:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:132:

```
Met Glu Leu Gly Leu Ser Trp Val Ser Leu Val Ile Ile Leu Lys Gly
 1               5                  10                  15

Val Cys Gly Val Gln Met Val Glu Ser Trp Gly Glu Leu Ala Gln Xaa
            20                  25                  30

Glu Cys Ala Asp Ser Ala Val His Pro Leu Asn Pro Pro Ser Val Ala
        35                  40                  45

Thr Arg Ser Ala Glu Ser Ala
    50                  55
```

2) INFORMATION FOR SEQ ID NO:133:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:133:

```
Met Gly Ser Thr Ala Ile Leu Ala Leu Leu Ala Val Leu Gln Gly
 1               5                  10                  15

Val Cys Ser Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45
```

```
Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
 65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg
        115
```

(2) INFORMATION FOR SEQ ID NO:134:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:134:

```
Met Glu Ser Gly Leu Ser Trp Val Phe Leu Val Ala Ile Leu Lys Gly
 1               5                  10                  15

Val Gln Cys Glu Val Gln Leu Val Glu Ser Gly Gly Leu Val Gln Pro
                20                  25                  30

Gly Gly Ser Leu Arg Leu Ser Cys Ala Ala Ser Gly Phe Thr Phe Ser
            35                  40                  45

Ser Ser Trp Met His Trp Val Cys Gln Ala Pro Glu Lys Gly Leu Glu
    50                  55                  60

Trp Val Ala Asp Ile Lys Cys Asp Gly Ser Glu Lys Tyr Tyr Val Asp
 65                  70                  75                  80

Ser Val Lys Gly Arg Leu Thr Ile Ser Arg Asp Asn Ala Lys Asn Ser
                85                  90                  95

Leu Tyr Leu Gln Val Asn Ser Leu Arg Ala Glu Asp Met Thr Val Tyr
            100                 105                 110

Tyr Cys Val Arg
        115
```

(2) INFORMATION FOR SEQ ID NO:135:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:135:

```
Met Glu Phe Trp Leu Ser Trp Val Phe Leu Val Ala Ile Leu Lys Gly
 1               5                  10                  15

Val Gln Cys Glu Val Gln Leu Val Glu Ser Gly Gly Gly Leu Ile Gln
                20                  25                  30

Pro Gly Gly Ser Leu Arg Leu Ser Cys Ala Ala Ser Gly Phe Thr Val
            35                  40                  45

Ser Ser Asn Tyr Met Ser Trp Val Arg Gln Ala Pro Gly Lys Gly Leu
    50                  55                  60

Glu Trp Val Ser Val Ile Tyr Ser Gly Gly Ser Thr Tyr Tyr Ala Asp
 65                  70                  75                  80
```

```
Ser Val Lys Gly Arg Phe Thr Ile Ser Arg Asp Asn Ser Lys Asn Thr
            85                  90                  95

Leu Tyr Leu Gln Met Asn Ser Leu Arg Ala Glu Asp Thr Ala Val Tyr
            100                 105                 110

Tyr Cys Ala Arg
        115

(2) INFORMATION FOR SEQ ID NO:136:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:136:

Met Glu Leu Gly Leu Ser Trp Val Phe Thr Val Thr Val Leu Lys Gly
 1               5                  10                  15

Val Gln Cys Glu Val Gln Leu Val Glu Ser Glu Glu Asn Gln Arg Gln
            20                  25                  30

Leu Gly Gly Ser Leu Arg Leu Ser Cys Ala Asp Ser Gly Leu Thr Phe
            35                  40                  45

Ser Ser Tyr Met Ser Ser Asp Ser Gln Ala Pro Gly Lys Gly Leu Glu
    50                  55                  60

Val Val Asp Ile Asp Arg Ser Gln Leu Cys Tyr Ala Gln Ser Val Lys
65                  70                  75                  80

Ser Arg Phe Thr Ile Ser Lys Glu Asn Ala Lys Asn Ser Leu Cys Leu
            85                  90                  95

Gln Met Asn Ser Leu Arg Ala Glu Gly Thr Ala Val Tyr Tyr Cys Met
            100                 105                 110

2) INFORMATION FOR SEQ ID NO:137:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:137:

Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
            20                  25                  30

Pro Ser Glu Thr Leu Ser Leu Ile Cys Ala Val Ser Gly Asp Ser Ile
            35                  40                  45

Ser Ser Gly Asn Trp Ile Trp Val Arg Gln Pro Pro Gly Lys Gly Leu
    50                  55                  60

Glu Trp Ile Gly Glu Ile His His Ser Gly Ser Thr Tyr Tyr Asn Pro
65                  70                  75                  80

Ser Leu Lys Ser Arg Ile Thr Met Ser Val Asp Thr Ser Lys Asn Gln
            85                  90                  95

Phe Tyr Leu Lys Leu Ser Ser Val Thr Ala Ala Asp Thr Ala Val Tyr
            100                 105                 110

Tyr Cys Ala Arg Tyr Thr Val Arg
        115                 120
```

(2) INFORMATION FOR SEQ ID NO:138:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:138:

```
Met Asp Trp Thr Trp Ser Ile Leu Phe Leu Val Ala Ala Thr Gly
 1               5                  10                  15

Ala His Ser Arg Val Gln Leu Val Gln Ser Gly Pro Glu Val Lys Gln
                20                  25                  30

Pro Gly Ala Ser Ala Lys Val Ser Cys Lys Val Ser Gly Thr Val Ile
            35                  40                  45

Thr Tyr Gly Met Asn Trp Ile Arg Gln Thr Pro Gly Gln Gly Leu Glu
        50                  55                  60

Trp Met Gly Trp Ile
65
```

(2) INFORMATION FOR SEQ ID NO:139:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:139:

```
Met Asp Trp Ile Trp Arg Ile Leu Phe Leu Val Gly Ala Ala Ile Gly
 1               5                  10                  15

Ala His Ser Gln Met Gln Leu Val Gln Ser Gly Pro Glu Val Lys Lys
                20                  25                  30

Pro Gly Thr Ser Val Lys Val Ser Cys Lys Ala Ser Gly Phe Thr Phe
            35                  40                  45

Thr Ser Ser Ala Val Gln Trp Val Arg Gln Ala Arg Gly Gln Arg Leu
        50                  55                  60

Glu Trp Ile Gly Trp Ile Val Val Gly Ser Gly Asn Thr Asn Tyr Ala
65                  70                  75                  80

Gln Lys Phe Gln Glu Arg Val Thr Ile Thr Arg Asp Met Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Ala
        115
```

(2) INFORMATION FOR SEQ ID NO:140:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:140:

```
Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
                20                  25                  30
```

Pro Ser Glu Thr Leu Ser Leu Thr Cys Thr Val Ser Gly Gly Ser Val
            35                  40                  45

Ser Ser Tyr Tyr Trp Ser Trp Ile Arg Gln Pro Pro Gly Lys Gly Leu
        50                  55                  60

Glu Trp Ile Gly Tyr Ile Tyr Tyr Ser Gly Ser Thr Asn Tyr Asn Pro
 65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg
        115

(2) INFORMATION FOR SEQ ID NO:141:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:141:

Met Glu Ser Gly Leu Ser Trp Ile Phe Leu Val Ala Val Leu Lys Gly
 1               5                  10                  15

Cys Pro Val Gly Ala Ala Gly Gly Val Trp Gly Arg Leu Ser Lys Asp
            20                  25                  30

Trp Gly Val Ser Glu Thr Leu Leu Cys Ser Leu Trp Ile His Leu Gln
        35                  40                  45

Leu Cys Tyr Ala Leu Gly Pro Pro Gly Ser Arg Lys Gly Phe Gly Val
    50                  55                  60

Gly Leu Ser Tyr Tyr Lys Trp Tyr Arg Thr Leu His Arg Leu Cys Glu
 65                  70                  75                  80

Gly Leu Ile His His Leu Arg Gln Cys Pro Glu Phe Thr Val Ser Ala
                85                  90                  95

Asn Glu Gln Pro Glu Ser Arg Arg His Gly Cys Val Leu Leu Cys Glu
            100                 105                 110

Arg (2) INFORMATION FOR SEQ ID NO:142:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:142:

Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
            35                  40                  45

Ser Ser Gly Ser Tyr Tyr Trp Ser Trp Ile Arg Gln Pro Pro Gly Lys
        50                  55                  60

Gly Leu Glu Trp Ile Gly Tyr Ile Tyr Tyr Ser Gly Ser Thr Asn Tyr

```
                65                  70                  75                  80
Asn Pro Ser Leu Lys Ser Arg Val Thr Ile Ser Val Asp Thr Ser Lys
                    85                  90                  95

Asn Gln Phe Ser Leu Lys Leu Ser Val Thr Ala Ala Asp Thr Ala
                100                 105                 110

Val Tyr Tyr Cys Ala Arg
        115

(2) INFORMATION FOR SEQ ID NO:143:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:143:

Met Glu Phe Gly Leu Ser Trp Val Phe Leu Val Ala Asn Leu Arg Gly
  1               5                  10                  15

Val Gln Cys Glu Val Gln Leu Val Glu Ser Gly Glu Gly Leu Val Gln
                 20                  25                  30

Pro Gly Gly Ser Leu Arg Leu Ser Cys Ala Ala Ser Gly Phe Thr Phe
             35                  40                  45

Ser Ser Ser Ala Met His Trp Val Arg Gln Ala Pro Arg Lys Gly Leu
         50                  55                  60

Trp Val Ser Val Ile Ser Thr Ser Gly Asp Thr Val Leu Tyr Thr Asp
 65                  70                  75                  80

Ser Val Lys Gly Arg Phe Thr Ile Ser Arg Asp Asn Ala Gln Asn Ser
                 85                  90                  95

Leu Ser Leu Gln Met Asn Ser Leu Arg Ala Glu Gly Thr Val Val Tyr
                100                 105                 110

Tyr Cys Val Lys
        115

(2) INFORMATION FOR SEQ ID NO:144:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:144:

Met Gly Phe Glu Leu Thr Arg Ile Phe Leu Val Ala Ile Leu Lys Gly
  1               5                  10                  15

Val Gln Cys Glu Val Glu Leu Ile Glu Ser Ile Glu Gly Leu Arg Gln
                 20                  25                  30

Leu Gly Lys Phe Leu Arg Leu Ser Cys Val Ala Ser Gly Phe Thr Phe
             35                  40                  45

Ser Ser Tyr Met Ser Trp Val Asn Glu Thr Leu Gly Lys Gly Leu Glu
         50                  55                  60

Gly Val Ile Asp Val Lys Tyr Asp Gly Ser Gln Ile Tyr His Ala Asp
 65                  70                  75                  80

Ser Val Lys Gly Arg Phe Thr Ile Ser Lys Asp Asn Ala Lys Asn Ser
                 85                  90                  95

Pro Tyr Leu Gln Thr Asn Ser Leu Arg Ala Glu Asp Met Thr Met His
                100                 105                 110
```

```
Gly Cys Thr
        115

(2) INFORMATION FOR SEQ ID NO:145:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:145:

Met Thr Glu Phe Gly Leu Ser Trp Val Phe Leu Val Ala Ile Phe Lys
 1               5                  10                  15

Gly Val Gln Cys Glu Val Gln Leu Val Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Ser Tyr Ala Met His Trp Val Arg Gln Ala Pro Gly Lys Gly
    50                  55                  60

Leu Glu Tyr Val Ser Ala Ile Ser Ser Asn Gly Gly Ser Thr Tyr Tyr
65                  70                  75                  80

Ala Asn Ser Val Lys Gly Arg Phe Thr Ile Ser Arg Asp Asn Ser Lys
                85                  90                  95

Asn Thr Leu Tyr Leu Gln Met Gly Ser Leu Arg Ala Glu Asp Met Ala
            100                 105                 110

Val Tyr Tyr Cys Ala Arg
            115
```